US009279015B2

(12) United States Patent
Wong et al.

(10) Patent No.: US 9,279,015 B2
(45) Date of Patent: Mar. 8, 2016

(54) METHODS FOR TREATMENT OF ANKYLOSING SPONDYLITIS USING TNF ALPHA ANTIBODIES

(76) Inventors: Robert L. Wong, Basking Ridge, NJ (US); Hartmut Kupper, Mutterstadt (DE); Michelle P. Luo, Libertyville, IL (US); Joachim Sieper, Berlin (DE); John C. Davis, San Francisco, CA (US); Walter P. Maksymowych, Edmonton (CA)

(*) Notice: Subject to any disclaimer, the term of this patent is extended or adjusted under 35 U.S.C. 154(b) by 782 days.

(21) Appl. No.: 12/012,787

(22) Filed: Feb. 4, 2008

(65) Prior Publication Data

US 2009/0123378 A1 May 14, 2009

Related U.S. Application Data

(63) Continuation of application No. 11/818,510, filed on Jun. 13, 2007, now abandoned, which is a continuation-in-part of application No. 11/786,461, filed on Apr. 10, 2007, now abandoned.

(60) Provisional application No. 60/858,376, filed on Nov. 10, 2006, provisional application No. 60/790,909, filed on Apr. 10, 2006, provisional application No. 60/809,770, filed on May 30, 2006, provisional application No. 60/815,489, filed on Jun. 20, 2006, provisional application No. 60/909,683, filed on Apr. 2, 2007.

(51) Int. Cl.
*A61K 39/395* (2006.01)
*A61K 39/00* (2006.01)
*C07K 16/24* (2006.01)

(52) U.S. Cl.
CPC ......... *C07K 16/241* (2013.01); *A61K 2039/505* (2013.01); *C07K 2317/21* (2013.01)

(58) Field of Classification Search
None
See application file for complete search history.

(56) References Cited

U.S. PATENT DOCUMENTS

| | | | |
|---|---|---|---|
| 5,656,272 A | 8/1997 | Le et al. | |
| 5,872,215 A * | 2/1999 | Osbourne et al. | 530/387.3 |
| 5,874,060 A * | 2/1999 | Armour et al. | 424/1.49 |
| 6,090,382 A | 7/2000 | Salfeld et al. | |
| 6,258,562 B1 | 7/2001 | Salfeld et al. | |
| 6,448,380 B2 | 9/2002 | Rathjen et al. | |
| 6,451,983 B2 | 9/2002 | Rathjen et al. | |
| 6,498,237 B2 | 12/2002 | Rathjen et al. | |
| 6,509,015 B1 | 1/2003 | Salfeld et al. | |
| 7,070,775 B2 | 7/2006 | Le et al. | |
| 7,078,064 B2 | 7/2006 | Zabrecky | |
| 7,192,584 B2 | 3/2007 | Le et al. | |
| 7,223,394 B2 | 5/2007 | Salfeld et al. | |
| 7,250,165 B2 | 7/2007 | Heavner et al. | |
| 7,276,239 B2 | 10/2007 | Le et al. | |
| 7,521,206 B2 | 4/2009 | Heavner et al. | |
| 7,541,031 B2 | 6/2009 | Salfeld et al. | |
| 7,588,761 B2 | 9/2009 | Salfeld et al. | |
| 7,691,378 B2 | 4/2010 | Heavner et al. | |
| 7,863,426 B2 | 1/2011 | Wan et al. | |
| 7,919,264 B2 | 4/2011 | Maksymowych et al. | |
| 8,034,906 B2 | 10/2011 | Borhani et al. | |
| 8,092,998 B2 | 1/2012 | Stuhlmuller et al. | |
| 8,093,045 B2 | 1/2012 | Pla et al. | |
| 8,187,836 B2 | 5/2012 | Hsieh | |
| 8,197,813 B2 | 6/2012 | Salfeld et al. | |
| 8,206,714 B2 | 6/2012 | Salfeld et al. | |
| 8,216,583 B2 | 7/2012 | Kruase et al. | |
| 8,231,876 B2 | 7/2012 | Wan et al. | |
| 8,372,400 B2 | 2/2013 | Salfeld et al. | |
| 8,372,401 B2 | 2/2013 | Salfeld et al. | |
| 8,414,894 B2 | 4/2013 | Salfeld et al. | |
| 8,420,081 B2 | 4/2013 | Fraunhofer et al. | |
| 8,436,149 B2 | 5/2013 | Borhani et al. | |
| 8,455,219 B2 | 6/2013 | Hsieh | |
| 8,636,704 B2 | 1/2014 | Shang et al. | |
| 8,663,945 B2 | 3/2014 | Pla et al. | |
| 8,679,061 B2 | 3/2014 | Julian et al. | |
| 2003/0012786 A1 | 1/2003 | Teoh et al. | |
| 2003/0161828 A1 | 8/2003 | Abdelghany et al. | |
| 2003/0206898 A1 | 11/2003 | Fischkoff et al. | |
| 2003/0219438 A1 | 11/2003 | Salfeld et al. | |
| 2003/0235585 A1 | 12/2003 | Fischkoff et al. | |
| 2004/0009172 A1 | 1/2004 | Fischkoff et al. | |
| 2004/0033228 A1 | 2/2004 | Krause et al. | |
| 2004/0105858 A1 * | 6/2004 | Kim et al. | 424/144.1 |
| 2004/0120952 A1 | 6/2004 | Knight et al. | |

(Continued)

FOREIGN PATENT DOCUMENTS

WO WO-97/29131 A1 8/1997
WO WO-02/12502 A2 2/2002

OTHER PUBLICATIONS

M. Rudwaleit et al., "How to diagnose axial spondyloarthritis early", Ann. Rheum. Dis. 2004, 63:535-543.*
Wikipedia (http://en.wikipedia.org/wiki/Ankylosing_spondylitis, accessed Jun. 18, 2010).*
Anderson et al., Arthritis & Rheumatism vol. 44, No. 8, Aug. 2001, pp. 1876-1886 (provided by applicants).*
Davis J. et al. 2005. Arthritis and Rheumatism. 52(S):S208.*
Braun et al., 2006. Ann Rheum Dis. 66:316-620, published on line Aug. 11, 2005.*
NCT00235105, 2005.*
NCT00195819, started Sep. 16, 2005.*
NCT00085644, started Jun. 10, 2004.*
Haibel H. et al., Adalimumab is Effective in Patients with Preradiographic Axial Spondyloarthritis: Results of a 12-Week, Randomized Controlled Trial, *Rheumatology*, 2007, 46(Suppl 1):i52.

(Continued)

*Primary Examiner* — Shulamith H Shafer
(74) *Attorney, Agent, or Firm* — Foley Hoag LLP

(57) ABSTRACT

The invention provides methods, uses and compositions for the treatment of ankylosing spondylitis (AS). The invention describes methods and uses for treating ankylosing spondylitis, wherein a TNFα inhibitor, such as a human TNFα antibody, or antigen-binding portion thereof, is used to reduce signs and symptoms of ankylosing spondylitis in a subject. Also described are methods for determining the efficacy of a TNFα inhibitor for treatment of ankylosing spondylitis in a subject.

10 Claims, 36 Drawing Sheets

(56) References Cited

U.S. PATENT DOCUMENTS

| | | |
|---|---|---|
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0219142 A1 | 11/2004 | Banerjee et al. |
| 2005/0123541 A1 | 6/2005 | Heavner et al. |
| 2005/0249735 A1 | 11/2005 | Le et al. |
| 2006/0009385 A1 | 1/2006 | Hoffman et al. |
| 2006/0018907 A1 | 1/2006 | Le et al. |
| 2006/0083741 A1 | 4/2006 | Hoffman et al. |
| 2006/0246073 A1 | 11/2006 | Knight et al. |
| 2007/0003548 A1 | 1/2007 | Heavner et al. |
| 2007/0041905 A1 | 2/2007 | Hoffman et al. |
| 2007/0071747 A1* | 3/2007 | Hoffman et al. ........... 424/145.1 |
| 2007/0081996 A1 | 4/2007 | Hoffman et al. |
| 2007/0172897 A1* | 7/2007 | Maksymowych et al. ..... 435/7.9 |
| 2007/0196373 A1 | 8/2007 | Le et al. |
| 2007/0202104 A1* | 8/2007 | Banerjee et al. ........... 424/145.1 |
| 2007/0248595 A1* | 10/2007 | Fischkoff et al. .......... 424/131.1 |
| 2007/0298040 A1 | 12/2007 | Le et al. |
| 2008/0025976 A1 | 1/2008 | Le et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0311043 A1 | 12/2008 | Hoffman et al. |
| 2009/0028794 A1 | 1/2009 | Medich et al. |
| 2009/0068172 A1 | 3/2009 | Kaymakcalan et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0226530 A1 | 9/2009 | Lassner et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0021451 A1 | 1/2010 | Wong |
| 2010/0040630 A1 | 2/2010 | Elden et al. |
| 2010/0160894 A1 | 6/2010 | Julian et al. |
| 2010/0278822 A1 | 11/2010 | Fraunhofer et al. |
| 2011/0054414 A1 | 3/2011 | Shang et al. |
| 2011/0171227 A1 | 7/2011 | Okun et al. |
| 2011/0300151 A1 | 12/2011 | Okun et al. |
| 2012/0014956 A1 | 1/2012 | Kupper et al. |
| 2012/0039900 A1 | 2/2012 | Stuhlmuller et al. |
| 2012/0077213 A1 | 3/2012 | Pla et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0258114 A1 | 10/2012 | Salfeld et al. |
| 2012/0282262 A1 | 11/2012 | Okun et al. |
| 2012/0282270 A1 | 11/2012 | Krause et al. |
| 2013/0004507 A1 | 1/2013 | Fischkoff et al. |
| 2013/0028903 A1 | 1/2013 | Wan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0243763 A1 | 9/2013 | Banerjee et al. |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0309242 A1 | 11/2013 | Wan et al. |
| 2013/0309309 A1 | 11/2013 | Borhani et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0344537 A1 | 12/2013 | Hsieh |
| 2014/0086929 A1 | 3/2014 | Krause et al. |
| 2014/0086930 A1 | 3/2014 | Krause et al. |
| 2014/0086931 A1 | 3/2014 | Krause et al. |

OTHER PUBLICATIONS

Haibel H. et al., Efficacy of Adalimumab in the Treatment of Preradiographic Axial Spondyloarthritis: Results of a 20-Week, Randomized Controlled Trial with an Open-Label Extension Phase, *Ann. Rheum. Dis.*, 2007, 66(Suppl II):64 (Abstract OP0043).

Haibel H. et al., Efficacy of Adalimumab in the Treatment of Axial Spondyloarthritis Without Radiographically Defined Sacroiliitis, *Arthritis Rheum.*, 2008, 58:1981-91.

Anderson J. et al., "Ankylosing spondylitis Assessment Group Preliminary Deifinition of Short Term Improvement in Ankylosing Spondylitis," Arthritis and Rheumatism (2001) 44 (8): 1876-1886.

Asli B. et al., "Inhibition of Tumor Necrosis Factor α and Ankylosing Apondylitis," N Engl J Med., (2003) 348(4) : 359-360.

Boeger C. et al., "Treatment of ankylosing spondylitis with infliximab", Ann Rheum Dis (2001) 60: 1159-1160.

Boules, P. et al., "Pharmacological treatment of ankylosing spondylitis," Drugs (2005) 65 (15): 2111-2127. XP009133932.

Brandt, J. et al., "Successful Short Term treatment of Severe Undifferentiated Spondyloarthropathy with the Anti-Tumor Necrosis Factor—a Monoclonal Antibody Infliximab," J Rheumatol (2002) 29: 118-122.

Brandt, J. et al., "Successful treatment of Active Ankylosing Spondylitis with the Anti-Tumor Necrosis Factor α Monoclonal Antibody Infliximab", Arthritis & Rheumat, (2000), 43 (6): 1346-1352.

Braun, J. et al., "Anti- tumor Necrosis factor α therapy for ankylosing spondylitis: international experience," Ann Rheum Dis (2002) 61 (Suppl III): ii51- ii60.

Braun, J. et al., "Anti-TNF-α: a new dimension in the pharmacotherapy of the spondyloarthropathies," Ann Rheum Dis, (2000) 59 (6): 404-407.

Braun, J. et al., "Biologic therapies in the spondyloarthritis: new opportunities, new challenges," Curr Opin Rheumatol, (2003) 5: 394-407.

Braun, J. et al., "International ASAS consensus statement for the use of anti-tumor necrosis factor agents with ankylosing spondylitis'" Ann Rheum Dis, (2003) 62: 817-824.

Braun, J. et al., "New Treatment Options in Spondyloarthropathies: Increasing Evidence for Significant Efficacy of Anti-Tumor Necrosis Factor Therapy," Curr. Opin Rheumatol. (2001) 13: 245-249.

Braun, J. et al., "Novel approaches in the treatment of ankylosing spondylitis and other spondyloarthritides," Expert Opin Inves Drugs, (2003), 12 (7): 1097-1109.

Braun, J. et al., "Therapy of ankylosing spondylitis and other spondyloarthritides: established medical treatment, anti-TNF α therapy and other novel approaches," Arthritis Res., (2002) 4: 307-321.

Braun, J. et al., "Treatment of active ankylosing spondylitis with infliximab: a randomised controlled multicentre trial," Lancet, (2002), 359: 1187-1193.

Breban., M. et al., "Efficacy of infliximab in refractory ankylosing spondylitis: results of a six month open-label study," Rheumatology (2002) 41: 1280-1285.

Cherouvim, E. P. et al., "Infliximab therapy for patients with active and refractory spondylarthropathies at the dose of 3 mg/kg." J. Clin Rheumatol., 2004, 10: 162-168.

Ching L. et al., "Induction of intratumoral tumor necrosis factor (TNF) synthesis and hemorrhagic necrosis by 5, 6-dimethylxanthenone-4-acetic acid (DMXAA) in TNF knockout mice'" Cancer Res., (1999), 59: 3304-3307.

Davis J. et al., "Major clinical response and partial remission in ankylosing spondylitis subjects treated with adalimumab: The ATLAS Trial," Arthritis & Rheumatism, (2005), 52: S208-209. XP009133946.

Davis, J. et al., "Adalimumab Reduces Pain and Fatigue in Ankylosing Spondylitis (AS) Patients—Results from the ATLAS Trial.," Annual Scientific Meeting, 2006, Amsterdam, The Netherlands, Jun. 21-24, 2006.

(56) References Cited

OTHER PUBLICATIONS

Davis, J. et al., "Understanding the role of tumor necrosis factor inhibition in ankylosing spondylitis," Seminars Arthritis Rheumatism, (2005), 34 (4): 668-677.
Dayer, J.M. et al., "Anti-TNF-α therapy for ankylosing spondylitis- a specific or nonspecific treatment", N Engl J Med, vol. 346, No. 18, (2002): 1399-1400.
De Keyser et al., "Anti- TNF-alpha therapy in ankylosing spondylitis." Cytokine, 2006, 93: 294-298.
Dernis, E. et al.,"Infliximab in spondylarthropathy—Influence on bone density", Clin Exp Rheumatol, (2002) 20 (Suppl. 28): S185-S186.
Dernis-Labous et al., Assessment of fatigue in the management of patients with ankylosing spondylitis. Rheumatology (Oxford), (2003), 42 (12): 1523-1528.
Efthimiou, P. et al., "Role of biological agents in immune-mediated inflamatory diseases", Southern Med J (2005) 98 (2): 192-204. XP009063672.
Gorman, J.D. et al., "Treatment of ankylosing spondylitis by inhibition of tumor necrosis factor α," N. Engl J Med., (2002), 346: 1349-1356.
Haibel, H et al., "Adalimumab in the treatment of active ankylosing spondylitis: Results of an open-label 52-week trial," Ann Rheum Dis, (2005), 64 (Suppl III): 316.
Haibel, H. et al., "Adalimumab reduced spinal symptoms in active ankylosing spondylitis: clinical and manetic resonance imaging results of a fifty-two week open-label trial", Arthritis & Rheumatism, (2006), 54: 678-681. XP-002583872.
Heiberg, M.S., et al., The comparative effectiveness of tumour necrosis factor-blocking agents in patients with rheumatoid arthritis and patients with ankylosing spondilytis: a six month, longitudinal, observational, mutlticenter study. Arthritis Rheum., (2005), 52(8): 2506-2512.
Horneff, G. et al., "TNF-a antagonists for the treatment of juvenile-onset spondyloarthritides," Clin Exp Rheumatol, (2002), (Suppl. 28): S137-S142.
Kaiser, M. J. et al., "Efficacy of infliximab (Remicade®) in the treatment of spondyloarthropathies. Two cae reports," Joint Bone Spine, (2001), 68: 525-527.
Kavanaugh, A.F., "Adalimumab Treatment with and without Methotrexate in Patients with Moderate to Severe Psoriatic Arthritis: Results from ADEPT," Abstract #FRI0227, Ann. Rheum. Dis., (2005), 64(Suppl III): 325.
Kempeni, J., "Preliminary results of early clinical trials with the fully human anti-TNF α monoclonal antibody D2E7," Ann Rheum Dis, (1999), 58: (Suppl I) 170-172.
Luc, M. et al., "Patients without biological inflammation and responders to anti-TNF-alpha in axial ankylosing spondyllitis," Arthritis & Rheumatism, (2005), 52: S216.
Luo, M. P. et al., "Adalimumab reduces fatigue in patients with active ankylosing spondylitis (AS)- 6 month results of a Canadian AS study", Value in Health, 2005, 8(6): A 13.
Maksymowych, W. P. et al., "Canadian Rheumatology Association Consensus on the Use of Anti-Tumor Necrosis Factor-α Directed Therapies in the Treatment of Spondyloarthritis," J Rheumatol, (2003), 30: 1356-1363.
Maksymowych, W. P. et al., "Efficacy of adalimumab in active ankylosing spondylitis (AS)-results of the Canadian AS Study," Arthritis & Rheumatism, (2005), 52: S217.
Marzo-Ortega, H. et al., "Inhibition of Tumor Necrosis Factor α and Ankylosing Spondylitis," N Engl J Med, (2003), 348 (4): 359-360.
Pham, T. et al., "Inhibition of biological agents in patients with ankylosing spondylitis: results of a Delphi study by the ASAS Group," Ann Rheum Dis, (2003), 62: 812-816.
Reimold, A. M. et al., "New Indication for Treatment of Chronic Inflammation by TNF-a Blockade," Am J Med Sci, (2003), 325 (2): 75-92.
Roussou et al., "The Bath Ankylosing Spondylitis Activity and Function Indices (BASDAI and BASFI) and their correlation with main symptoms experienced by patients with spondyloarthritis," Clin Rheumatol., (2010), 29: 869-874.
Rudwaleit, M. et al., "How to diagnose axial spondyloarthritis early," Ann Rheum Dis, (2004), 63: 535-543.
Schnarr, S. et al., "Anti-tumour necrosis factor (TNF)-α therapy in undifferentiated spondyloarthopathy," Clin Exp Rheumatol, (2002), 20 (Suppl. 28): S126-S129.
Sieper, J. et al., "New treatment options in ankylosing spondylitis: a role for anti-TNFα therapy," Ann Rheum Dis, (2001), 60: iii58-iii61.
Steinerova, M et al., "A pilot study with referred patients suffering early spondyloarthropathies: results of espidep study." Ann Rheum Dis., 2007, 66 (Suppl II): 410.
Stokes, D. G. et al., "Potential of Tumor Necrosis Factor Neutralization Strategies in Rheumatological Disorders Other Than Rheumatoid Arthritis," Seminars in Arthritis and Rheumatism, (2003), 33(1): 1-18.
Stone, M. et al., "Clinical and Imaging Correlates of Response to Treatment with Infliximab in Patients with Ankylosing Spondylitis," J Rheumatol (2001), 28: 1605-1614.
Van der Bosch, F. et al., "Crohn's disease asociated with spondyloarthropathy: effect of TNF-α blockade with infliximab on articular symptoms," The Lancet, (2000), 356: 1821-1822.
Van der Heijde, D. et al., "Adalimumab improves health-related quality of life in ptients with active ankylosing spondylitis- The ATLAS trial," (2005), 52(9): S211.
Van der Heijde, D. et al., "Adalimumab therapy results in significant reduction of signs and symptoms in subjects with ankylosing spondylitis: The ATLAS Trial" Arthritis & Rheumatism, (2005), 52 (9): S281.
Wendling D. et al., "Anti-TNFα therapy in ankylosing spondylitis," Expert Opin Pharmacother., (2004), 5(7): 1497-1507.
Wikipedia, Ankylosing Spondylitis [online], [retrieved on Jul. 3, 2013]. Retrieved from the Internet URL: http://en.wikipedia.org/wiki/Ankylosing_spondylitis.
Zou, J. X. et al., "Immunological basis for the use of TNFα-blocking agents in ankylosing spondylitis and immunological changes during treatment," Clin Exp Rheumatol., (2002), 20(Suppl. 28): S34-S37.
U.S. Appl. No. 10/622,683, filed Jul. 18, 2013, Banerjee, et al.
U.S. Appl. No. 11/818,510, filed Jun. 13, 2007, Wong, et al.
U.S. Appl. No. 11/786,053, filed Apr. 10, 2007, Willian, et al.
U.S. Appl. No. 11/786,444, filed Apr. 10, 2007, Pollack, et al.
U.S. Appl. No. 11/786,445, filed Apr. 10, 2007, Pollack, et al.
U.S. Appl. No. 11/786,461, filed Apr. 10, 2007, Wong, et al.
U.S. Appl. No. 11/788,312, filed Apr. 19, 2007, Willian, et al.
U.S. Appl. No. 11/788,740, filed Apr. 19, 2007, Kupper, et al.
U.S. Appl. No. 11/804,587, filed May 17, 2007, Hoffman, et al.
U.S. Appl. No. 11/824,516, filed Jun. 29, 2007, Julian, et al.
U.S. Appl. No. 11/880,433, filed Jul. 20, 2007, Willian, et al.
U.S. Appl. No. 12/130,831, filed May 30, 2008, Pollack, et al.
U.S. Appl. No. 12/306,513, filed Dec. 23, 2008, Julian, et al.
U.S. Appl. No. 12/646,891, filed Dec. 23, 2009, Okun, et al.
U.S. Appl. No. 13/019,810, filed Feb. 2, 2011, Kupper, et al.
U.S. Appl. No. 14/156,829, filed Jan. 23, 2014, Pla, et al.
U.S. Appl. No. 14/157,460, filed Jan. 23, 2014, Pla, et al.
U.S. Appl. No. 14/010,172, filed Aug. 26, 2013, Hoffman, et al.
U.S. Appl. No. 14/147,287, filed Jan. 3, 2014, Krause, et al.
U.S. Appl. No. 14/170,045, filed Jan. 31, 2014, Julian, et al.
U.S. Appl. No. 14/173,780, filed Feb. 5, 2014, Hoffman, et al.
U.S. Appl. No. 14/175,993, filed Feb. 7, 2014, Fischkoff et al.
U.S. Appl. No. 14/183,845, filed Feb. 19, 2014, Kaymackalan et al.
U.S. Appl. No. 14/195,588, filed Mar. 3, 2014, Pla et al.
U.S. Appl. No. 14/226,333, filed Mar. 26, 2014, Pla et al.
U.S. Appl. No. 14/226,579, filed Mar. 26, 2014, Pla et al.

* cited by examiner

SPARCC MRI Spinal Index: Maximum Score per Disco-vertebral Unit (DVU)

Cumulative probability of improvement in the Spihal (SPARCC)= scores for adalimumab versus placebo-treated patients at Week 12

Cumulative improvement in sacroiliac joint SPARCC score for adalimumab versus placebo treated patients at Week 12

Scatter plots of the spinal SPARCC change score versus baseline spinal SPARCC score Conceptual Structure

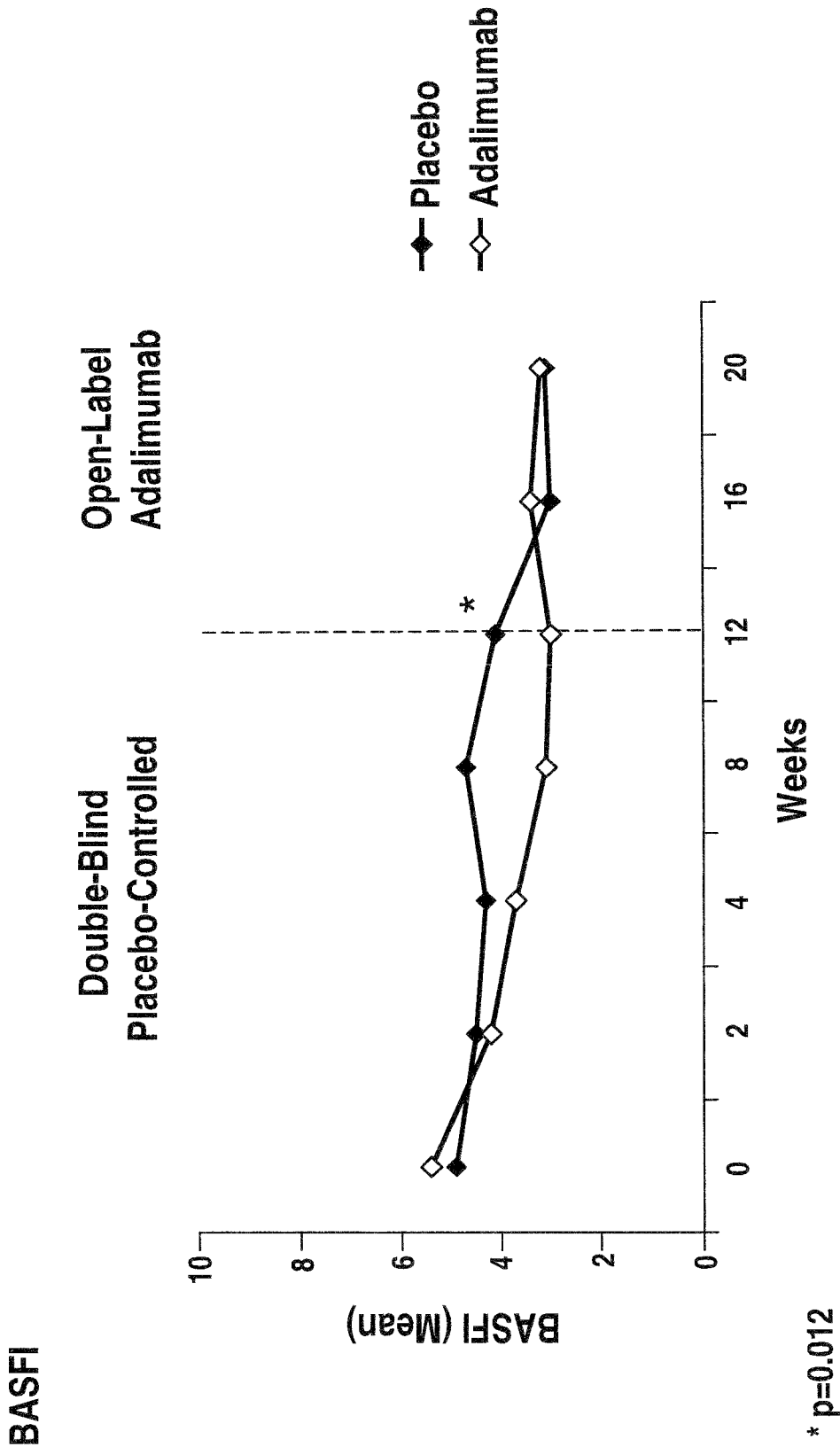

METHODS FOR TREATMENT OF ANKYLOSING SPONDYLITIS USING TNF ALPHA ANTIBODIES

RELATED APPLICATIONS

This application is a continuation of U.S. application Ser. No. 11/818,510, filed Jun. 13, 2007. U.S. application Ser. No. 11/818,510 is a continuation-in-part of U.S. application Ser. No. 11/786,461, filed Apr. 10, 2007. U.S. application Ser. No. 11/786,461 claims the benefit of priority to U.S. provisional patent application No. 60/790,909 filed on Apr. 10, 2006; U.S. provisional patent application No. 60/809,770 filed on May 30, 2006; U.S. provisional patent application No. 60/815,489 filed on Jun. 20, 2006; U.S. provisional patent application No. 60/909,683 filed on Apr. 2, 2007; and U.S. provisional patent application No. 60/858,376 filed on Nov. 10, 2006. The contents of all the above-mentioned priority applications are hereby incorporated by reference in their entirety.

BACKGROUND OF THE INVENTION

Ankylosing spondylitis (AS) is a chronic, progressive, inflammatory disease with considerable impact on patient functioning, well-being, and disability. The prevalence of AS has traditionally been estimated in the range of 0.1-1.9%, with more males affected than females (Sieper et al. Ann Rheum Dis 2001; 60:3-18; Silman & Hochberg Rheum Dis Clin North Am 1996; 22:737-49; Gran & Husby, Semin Arthritis Rheum 1993; 22(5):319-34). Millions of people are affected by ankylosing spondylitis (AS). As a chronic disease of the axial skeleton and large peripheral joints, AS causes inflammatory back pain and stiffness and it is associated with other inflammatory diseases of the skin, eyes and intestines. AS is difficult to diagnose in its early stages and is often an overlooked cause of persistent back pain in young adults.

As the disease progresses, patients with AS experience pain, joint stiffness, and the eventual loss of spinal mobility. These clinical symptoms and subsequent disease progression result in functional limitations, as well as impairment in health-related quality of life (Dagfinrud et al. Ann Rheum Dis 2004:63:1605-10; Bostan et al. Rheumatol Int 2003; 23:121-6; Zink et al., J Rheumatol 2000; 27:613-22; Ward 1998, Rheum Dis Clin North Am 1998; 24:815-27). In severe cases, AS may result in complete spinal fusion, causing extreme physical limitation.

No cure exists for AS. Traditionally, there were only a limited number of treatments available for ankylosing spondylitis (AS), including nonsteroidal anti-inflammatory drugs (NSAIDs) and physiotherapy. NSAIDs and physiotherapy provide symptomatic relief but do not affect disease activity or progression in AS. Traditional disease-modifying antirheumatic drugs (DMARDs), such as methotrexate and sulfasalazine, have demonstrated only limited effectiveness. Generally, treatment includes trying to relieve pain and stiffness using medications such as nonsteroidal anti-inflammatory drugs (NSAIDs), corticosteroids, and disease-modifying antirheumatic drugs (DMARDs). In recent years, biologic response modifiers that inhibit TNF activity have become additional therapies for treating AS, as tumor necrosis factor (TNFα) is present in increased concentrations in joints.

SUMMARY OF THE INVENTION

Although TNFα inhibitors are effective at treating AS, there remains a need for a more effective treatment option for subjects suffering from AS, especially in improving the fatigue and pain associated with the disease and in treating subjects who have failed more conventional therapy, i.e., DMARD or NSAIDs. Thus, there also remains a need for improved methods and compositions that provide a safe and effective treatment of AS using TNFα inhibitors.

The invention provides improved methods, uses, and compositions for treating AS using TNFα inhibitors, including human TNFα antibodies, or antigen-binding portions thereof.

The invention includes a method of decreasing pain and fatigue in a subject having AS comprising administering a TNFα inhibitor, e.g., human TNFα antibody, or antigen-binding portion thereof, to the subject such that pain and fatigue are decreased.

The invention also includes a use of a TNFα inhibitor, e.g., human TNFα antibody, or antigen-binding portion thereof, in the manufacture of a medicament for the treatment of pain and fatigue in a subject having AS.

In one embodiment, the decrease in fatigue is determined by a decrease of at least about 1.1 in a BASDAI score of the subject. In one embodiment, the decrease in fatigue is determined by a decrease of at least about 2.2 in a BASDAI score of the subject. In one embodiment, the decrease in fatigue is determined by a decrease of at least about 2.3 in a BASDAI score of the subject.

The invention also provides a method of inducing partial remission of AS in a subject comprising administering a TNFα inhibitor, e.g., human TNFα antibody, or antigen-binding portion thereof, to the subject, such that partial remission of AS is induced. The invention further provides a use of a TNFα inhibitor, e.g., human TNFα antibody, or antigen-binding portion thereof, in the manufacture of a medicament for inducing partial remission of AS in a subject. In one embodiment, partial remission is sustained for at least 52 weeks. In one embodiment, the subject has a value of less than 20 on a scale of 0-100 in all four ASAS domains.

The invention includes a method of achieving a decrease of at least about 50% in a spinal SPARCC score of a subject having AS comprising administering a TNFα inhibitor, e.g., human TNFα antibody, or antigen-binding portion thereof, to the subject such that the spinal SPARCC score is decreased by at least about 50%. In one embodiment, a decrease of at least about 54% in the spinal SPARCC score of the subject is achieved. In one embodiment, a decrease of at least about 57% in the spinal SPARCC score of the subject is achieved.

The invention describes a method of achieving a decrease of at least about 51% in a joint SPARCC score of a subject having AS comprising administering a TNFα inhibitor, e.g., human TNFα antibody, or antigen-binding portion thereof, to the subject such that the spinal SPARCC score is decreased by at least about 50%. In one embodiment, a decrease of at least about 53% in the joint SPARCC score of the subject is achieved. In one embodiment, a decrease of at least about 59% in the joint SPARCC score of the subject is achieved.

The invention includes a method of treating ankylosing spondylitis in a subject comprising administering a dose of a TNFα inhibitor, e.g., human TNFα antibody, or antigen-binding portion thereof, to the subject, wherein the dose results in a mean serum trough concentration of about 6-7 μg/mL of the TNFα inhibitor.

The invention also includes a method of treating ankylosing spondylitis in a subject comprising administering a concomitant therapy comprising a TNFα inhibitor e.g., human TNFα antibody, or antigen-binding portion thereof, and methotrexate to the subject, wherein the concomitant therapy results in a mean serum trough concentration of about 7-9 µg/mL of the TNFα inhibitor.

A method of treating ankylosing spondylitis (AS) in a subject who has failed prior treatment with a TNFα inhibitor comprising administering a human TNFα antibody, or antigen-binding portion thereof, to the subject such that AS is treated. In one embodiment, the subject has failed prior treatment with infliximab and/or etanercept.

In one embodiment, the invention provides a method of treating early axial spondylarthritis in a subject comprising administering a TNFα inhibitor, e.g., human TNFα antibody, or antigen-binding portion thereof, to the subject, such that early axial spondylarthritis is treated.

In one embodiment, the TNFα inhibitor is administered to the subject on a biweekly dosing regimen. In another embodiment, the TNFα inhibitor is administered in a dose of about 40 mg. In yet another embodiment, the TNFα inhibitor is administered to the subject subcutaneously.

The invention also provides a method for determining whether a patient (or patient population) is being effectively treated with a TNFα inhibitor, e.g., a human antibody or antigen-binding portion thereof, based on the patient's Patient Acceptable Symptom State (PASS) response. Thus, the invention provides a method of determining the efficacy of a TNFα inhibitor for treating ankylosing spondylitis (AS) in a subject comprising determining a PASS response of a patient population having AS and who was administered the TNFα inhibitor, wherein a PASS response of "yes" in at least about 29% of the patient population indicates that the TNFα inhibitor is an effective TNFα inhibitor for the treatment of AS in a subject. In one embodiment, the invention further comprises administering the effective TNFα inhibitor to s subject for the treatment of AS. In one embodiment, the invention provides a method of treating AS in a subject comprising administering an effective TNFα inhibitor to the subject such that AS is treated, wherein the effective TNFα inhibitor was previously identified providing a "yes" PASS response in at least about 29% of a patient population having AS and who was administered the TNFα inhibitor.

The invention also provides a method of determining the efficacy of a TNFα inhibitor, e.g., human TNFα antibody, or antigen-binding portion thereof, for treating ankylosing spondylitis (AS) in a subject comprising determining a Bath Ankylosing Spondylitis Disease Activity Index (BASDAI) 20 response of a patient population having AS and who was administered the TNFα inhibitor, wherein an BASDAI 20 response in at least about 80% of the patient population indicates that the TNFα inhibitor is an effective TNFα inhibitor for the treatment of AS in a subject.

The invention also includes a method of determining the efficacy of a TNFα inhibitor, e.g., human TNFα antibody, or antigen-binding portion thereof, for treating ankylosing spondylitis (AS) in a subject comprising determining a Bath Ankylosing Spondylitis Disease Activity Index (BASDAI) 50 response of a patient population having AS and who was administered the TNFα inhibitor, wherein an BASDAI 50 response in at least about 67% of the patient population indicates that the TNFα inhibitor is an effective TNFα inhibitor for the treatment of AS in the subject.

The invention includes a method of determining the efficacy of a TNFα inhibitor, e.g., human TNFα antibody, or antigen-binding portion thereof, for treating ankylosing spondylitis (AS) in a subject comprising determining a Bath Ankylosing Spondylitis Disease Activity Index (BASDAI) 70 response of a patient population having AS and who was administered the TNFα inhibitor, wherein an BASDAI 70 response in at least about 27% of the patient population indicates that the TNFα inhibitor is an effective TNFα inhibitor for the treatment of AS in the subject.

The invention further includes a method of determining the efficacy of a TNFα inhibitor, e.g., human TNFα antibody, or antigen-binding portion thereof, for treating ankylosing spondylitis (AS) in a subject comprising determining an Assessment in Ankylosing Spondylitis (ASAS) response of a patient population having AS and who was administered the TNFα inhibitor, wherein an ASAS20 response in at least about 61% of the patient population indicates that the TNFα inhibitor is an effective TNFα inhibitor for the treatment of AS in the subject. In one embodiment, an ASAS20 response in at least about 70% of the patient population indicates that the TNFα inhibitor is an effective TNFα inhibitor for the treatment of AS in the subject. In one embodiment, an ASAS20 response in at least about 73% of the patient population indicates that the TNFα inhibitor is an effective TNFα inhibitor for the treatment of AS in the subject. In one embodiment, an ASAS20 response in at least about 75% of the patient population indicates that the TNFα inhibitor is an effective TNFα inhibitor for the treatment of AS in the subject.

In one embodiment, the invention further comprises administering the effective TNFα inhibitor to s subject for the treatment of AS.

The invention also includes a method of treating AS in a subject comprising administering an effective TNFα inhibitor to the subject such that AS is treated, wherein the effective TNFα inhibitor was previously identified as resulting in a BASDAI 20 response in at least about 80% of a patient population having AS and who was administered the TNFα inhibitor.

The invention further provides a method of treating AS in a subject comprising administering an effective TNFα inhibitor to the subject such that AS is treated, wherein the effective TNFα inhibitor was previously identified as resulting in a BASDAI 50 response in at least about 67% of a patient population having AS and who was administered the TNFα inhibitor.

The invention also describes a method of treating AS in a subject comprising administering an effective TNFα inhibitor to the subject such that AS is treated, wherein the effective TNFα inhibitor was previously identified as resulting in a BASDAI 70 response in at least about 27% of a patient population having AS and who was administered the TNFα inhibitor.

The invention also includes a method of treating AS in a subject comprising administering an effective TNFα inhibitor to the subject such that AS is treated, wherein the effective TNFα inhibitor was previously identified as resulting in an ASAS20 response in at least about 61% of a patient population having AS who was administered the TNFα inhibitor.

The invention also provides a method of determining the efficacy of a TNFα inhibitor, e.g., human TNFα antibody, or antigen-binding portion thereof, or for treating ankylosing spondylitis (AS) in a subject comprising determining a Assessment in Ankylosing Spondylitis (ASAS) 50 response of a patient population having AS and who was administered the TNFα inhibitor, e.g., human TNFα antibody, or antigen-binding portion thereof, wherein an ASAS50 response in at least about 16% of the patient population indicates that the TNFα inhibitor, e.g., human TNFα antibody, or antigen-binding portion thereof, is an effective TNFα inhibitor for the treatment of AS in the subject. In one embodiment, an ASAS50 response in at least about 20% of the patient population indicates that the TNFα inhibitor, e.g., human TNFα antibody, or antigen-binding portion thereof, is an effective TNFα inhibitor, e.g., human TNFα antibody, or antigen-binding portion thereof, for the treatment of AS in the subject. In one embodiment, an ASAS50 response in at least about 30% of the patient population indicates that the TNFα inhibitor, e.g., human TNFα antibody, or antigen-binding portion thereof, is an effective TNFα inhibitor, e.g., human TNFα antibody, or antigen-binding portion thereof, for the treatment of AS in the subject. In one embodiment, an ASAS50 response in at least about 38% of the patient population indicates that the TNFα inhibitor, e.g., human TNFα antibody, or antigen-binding portion thereof, is an effective human TNFα antibody, or antigen-binding portion thereof, for the treatment of AS in the subject.

The invention also includes a method of determining the efficacy of a TNFα inhibitor, e.g., human TNFα antibody or for treating ankylosing spondylitis (AS) in a subject comprising determining a Assessment in Ankylosing Spondylitis (ASAS) 70 response of a patient population having AS and who was administered the TNFα inhibitor, e.g., human TNFα antibody, or antigen-binding portion thereof, wherein an ASAS70 response in at least about 7% of the patient population indicates that the TNFα inhibitor, e.g., human TNFα antibody, or antigen-binding portion thereof, is an effective TNFα inhibitor, e.g., human TNFα antibody, or antigen-binding portion thereof, for the treatment of AS in the subject.

In one embodiment, an ASAS70 response in at least about 20% of the patient population indicates that the TNFα inhibitor, e.g., human TNFα antibody, or antigen-binding portion thereof, is an effective TNFα inhibitor, e.g., human TNFα antibody, or antigen-binding portion thereof, for the treatment of AS in the subject. In one embodiment, an ASAS70 response in at least about 23% of the patient population indicates that the TNFα inhibitor, e.g., human TNFα antibody, or antigen-binding portion thereof, is an effective TNFα inhibitor, e.g., human TNFα antibody, or antigen-binding portion thereof, for the treatment of AS in the subject. In one embodiment, an ASAS70 response in at least about 30% of the patient population indicates that the TNFα inhibitor, e.g., human TNFα antibody, or antigen-binding portion thereof, is an effective TNFα inhibitor, e.g., human TNFα antibody, or antigen-binding portion thereof, for the treatment of AS in the subject. In one embodiment, an ASAS70 response in at least about 40% of the patient population indicates that the TNFα inhibitor, e.g., human TNFα antibody, or antigen-binding portion thereof, is an effective TNFα inhibitor, e.g., human TNFα antibody, or antigen-binding portion thereof, for the treatment of AS in the subject.

In one embodiment, the invention further comprises administering the effective TNFα inhibitor, e.g., human TNFα antibody, or antigen-binding portion thereof, to a subject to treat AS.

The invention also includes a method of treating AS in a subject comprising administering an effective TNFα inhibitor, e.g., human TNFα antibody, or antigen-binding portion thereof, to the subject, wherein the effective TNFα inhibitor, e.g., human TNFα antibody, or antigen-binding portion thereof, was previously identified as achieving an ASAS50 response in at least about 16% of a patient population having AS who was administered the TNFα inhibitor, e.g., human TNFα antibody, or antigen-binding portion thereof.

The invention provides a method of treating AS in a subject comprising administering an effective TNFα inhibitor, e.g., human TNFα antibody, or antigen-binding portion thereof, to the subject, wherein the effective TNFα inhibitor, e.g., human TNFα antibody, or antigen-binding portion thereof, was previously identified as achieving an ASAS70 response in at least about 23% of a patient population having AS who was administered the TNFα inhibitor, e.g., human TNFα antibody, or antigen-binding portion thereof.

The invention also includes an article of manufacture comprising a TNFα inhibitor, e.g., human TNFα antibody, or antigen-binding portion thereof, and a package insert comprising instructions for administering the TNFα inhibitor, e.g., human TNFα antibody, or antigen-binding portion thereof, to a human subject for the treatment of adults with moderate to severe active ankylosing spondylitis who have had an inadequate response to conventional therapy.

The invention also includes an article of manufacture comprising a TNFα inhibitor, e.g., human TNFα antibody, or antigen-binding portion thereof, and a package insert which indicates that the TNFα inhibitor, e.g., human TNFα antibody, or antigen-binding portion thereof, is indicated for the treatment of adults with moderate to severe active ankylosing spondylitis who have had an inadequate response to conventional therapy.

The invention includes an article of manufacture comprising a TNFα inhibitor, e.g., human TNFα antibody, or antigen-binding portion thereof, and a package insert which indicates that the TNFα inhibitor, e.g., human TNFα antibody, or antigen-binding portion thereof, is indicated for the treatment of patients who have had an inadequate response to or are intolerant to prior TNF inhibitor or antagonist therapy, e.g., infliximab and/or etanercept.

The invention also provides a method of testing the effectiveness of a TNFα inhibitor for the treatment of AS comprising administering the TNFα inhibitor to a preselected patient population having AS and determining the effectiveness of the TNFα inhibitor using the Assessment in Ankylosing Spondylitis (ASAS) response rate in the patient population, wherein an ASAS20 response rate in about 68% of the patient population indicates the TNFα inhibitor is effective for the treatment of AS.

The invention provides a method of testing the efficacy of a TNFα inhibitor for the treatment of AS comprising administering the TNFα inhibitor to a preselected patient population having AS; and determining the efficacy of the TNFα inhibitor using a baseline Bath Ankylosing Spondylitis Activity Index (BASDAI) score of the patient population and a BASDAI score of the patient population following administration of the TNFα inhibitor, wherein a BASDAI20 in about 80% of the patient population indicates that the TNFα inhibitor is effective for treating AS.

The invention further provides a method of testing the efficacy of a TNFα inhibitor for the treatment of AS comprising administering the TNFα inhibitor to a preselected patient population having AS; and determining the efficacy of the TNFα inhibitor using a baseline ASAS score of the patient population and an ASAS score of the patient population following administration of the TNFα inhibitor, wherein a ASAS70 in about 40% of the patient population indicates the TNFα inhibitor is effective for treating AS.

The invention describes a method of predicting long-term efficacy of a TNFα inhibitor for treatment of AS in a human subject comprising administering the TNFα inhibitor to the subject; and predicting the long-term efficacy using a baseline C-reactive protein (CRP) concentration of the subject and the CRP concentration of the subject at about 2 weeks following administration of the TNFα inhibitor, wherein a CRP concentration decrease to a normal range indicates that the TNFα inhibitor will be effective for the long term treatment of AS.

The invention includes a method of achieving partial remission of a patient having AS comprising administering to the patient a TNFα inhibitor.

The invention also provides a method of increasing work productivity in a patient having AS comprising administering to the patient a human TNFα antibody, or antigen-binding portion thereof, such that physical functioning is improved.

The invention includes a method for determining the efficacy of a TNFα inhibitor for the treatment of ankylosing spondylitis (AS) in a patient comprising assessing whether the patient considers his/her current disease state satisfactory (PASS).

The invention also provides a method for improving the overall well being of a subject having AS comprising administering a TNFα inhibitor to the subject and determining the physical functioning response of the subject, wherein an improvement in the physical functioning response indicates an improvement in the overall well being of the subject.

The invention also provides a method for monitoring the effectiveness of a TNFα inhibitor for the treatment of pain in a human subject having AS comprising: administering the TNFα inhibitor to the subject; and determining the effectiveness of the TNFα inhibitor using a baseline score from a pain assessment test selected from the group consisting of Total Back Pain (TBP) VAS, Nocturnal Pain (NP) VAS, and the SF-36 Bodily Pain domain and a score from the pain assessment test following administration of the TNFα inhibitor, wherein a change selected from the group consisting of about −19.5 for the TBP assessment test; about −19.2 for the NP assessment test; and about 19.2 for the SF-36 assessment test indicates that the TNFα inhibitor is effective at reducing pain in a subject having AS.

The invention includes a method of predicting the efficacy of a TNFα inhibitor for the treatment of AS comprising administering the TNFα inhibitor to a human subject having AS; predicting the efficacy of the TNFα inhibitor using a baseline C-reactive protein (CRP) level of the human subject and a CRP level following administration of the TNFα inhibitor, wherein a reduction in the CRP level to normal levels indicates that the TNFα inhibitor is effective at treating AS.

The invention also describes method of increasing work productivity in a patient having AS comprising administering to the patient a TNFα inhibitor such that physical functioning is improved.

The invention includes a method of treating ankylosing spondylitis (AS) in a subject comprising subcutaneously administering to the subject a TNFα inhibitor on a biweekly dosing regimen, wherein the serum trough concentration level of the TNFα inhibitor in the subject is no less than about 6-7 μg/mL. In one embodiment, the TNFα inhibitor is administered in combination with methotrexate.

The invention also provides a method of treating AS in a subject comprising subcutaneously administering to the subject a TNFα inhibitor on a biweekly dosing regimen in combination with methotrexate, wherein the serum trough concentration level of TNFα inhibitor in the subject is no less than about 7-9 μg/mL.

The invention describes a package comprising a TNFα inhibitor and a label, in a position which is visible to prospective purchasers, comprising a printed statement which informs prospective purchasers that TNFα inhibitor mean steady-state trough concentrations of approximately 6-7 μg/mL and 7-9 μg/mL were observed without and with methotrexate, respectively.

The invention describes a method of testing the effectiveness of a TNFα inhibitor for the treatment of AS comprising administering the TNFα inhibitor to a preselected patient population having AS and determining the effectiveness of the TNFα inhibitor using the Assessment in Ankylosing Spondylitis (ASAS) response rate in the patient population, wherein an ASAS20 response rate in about 68% of the patient population indicates the TNFα inhibitor is effective for the treatment of AS.

The invention further includes a method of testing the efficacy of a TNFα inhibitor for the treatment of AS administering the TNFα inhibitor to a preselected patient population having AS; and determining the efficacy of the TNFα inhibitor using the presence of anti-TNFα inhibitor antibodies in the serum of subjects of the patient population in correlation with a baseline ASAS score from the patient population and an ASAS score of the patient population following administration of the TNFα inhibitor, wherein the TNFα inhibitor is effective for treating AS if an ASAS20 response is achieved in about 76% of patients determined as having no anti-TNFα inhibitor antibodies in the serum. In one embodiment, the TNFα inhibitor has already been administered to the pre-selected patient population when the efficacy is determined.

The invention also includes a method of testing the efficacy of a TNFα inhibitor for the treatment of AS administering the TNFα inhibitor to a preselected patient population having AS; and determining the efficacy of the TNFα inhibitor using the presence of anti-TNFα inhibitor antibodies in the serum of subjects of the patient population in correlation with a baseline ASAS score from the patient population and an ASAS score of the patient population following administration of the TNFα inhibitor, wherein the TNFα inhibitor is effective for treating AS is an ASAS20 response is achieved in about 68% of patients determined as having anti-TNFα inhibitor antibodies in their serum. In one embodiment, the presence of anti-TNFα inhibitor antibodies is determining using ELISA methods. In one embodiment, the TNFα inhibitor has already been administered to the pre-selected patient population when the efficacy is determined.

The invention describes a method of testing the efficacy of a TNFα inhibitor for the treatment of AS comprising: administering the TNFα inhibitor to a preselected patient population having AS; and determining the efficacy of the TNFα inhibitor using a baseline Bath Ankylosing Spondylitis Activity Index (BASDAI) score of the patient population and a BASDAI score of the patient population following administration of the TNFα inhibitor, wherein a BASDAI20 in about 80% of the patient population indicates that the TNFα inhibitor is effective for treating AS. In one embodiment, the TNFα inhibitor has already been administered to the pre-selected patient population when the efficacy is determined.

The invention also includes a method of testing the efficacy of a TNFα inhibitor for the treatment of AS comprising: administering the TNFα inhibitor to a preselected patient population having AS; and determining the efficacy of the TNFα inhibitor using a baseline BASDAI score of the patient population and a BASDAI score of the patient population following administration of the TNFα inhibitor, wherein a BASDAI50 in about 67% of the patient population indicates the TNFα inhibitor is effective for treating AS. In one embodiment, the TNFα inhibitor has already been administered to the pre-selected patient population when the efficacy is determined.

The invention describes a method of testing the efficacy of a TNFα inhibitor for the treatment of AS comprising: administering the TNFα inhibitor to a preselected patient population having AS; and determining the efficacy of the TNFα inhibitor using a baseline BASDAI score of the patient population and a BASDAI score of the patient population following administration of the TNFα inhibitor, wherein a BASDAI70 in about 27% of the patient population indicates the TNFα inhibitor is effective for treating AS. In one embodiment, the TNFα inhibitor has already been administered to the pre-selected patient population when the efficacy is determined.

The invention also provides a method of testing the efficacy of a TNFα inhibitor for the treatment of AS comprising: administering the TNFα inhibitor to a preselected patient population having AS; and determining the efficacy of the TNFα inhibitor using a baseline ASAS score of the patient population and an ASAS score of the patient population following administration of the TNFα inhibitor, wherein an ASAS20 in about 73% of the patient population indicates that TNFα inhibitor is effective for treating AS. In one embodiment, the TNFα inhibitor has already been administered to the pre-selected patient population when the efficacy is determined.

The invention describes a method of testing the efficacy of a TNFα inhibitor for the treatment of AS comprising: administering the TNFα inhibitor to a preselected patient population having AS; and determining the efficacy of the TNFα inhibitor using a baseline ASAS score of the patient population and an ASAS score of the patient population following administration of the TNFα inhibitor, wherein an ASAS40 in about 60% of the patient population indicates the TNFα inhibitor is effective for treating AS. In one embodiment, the TNFα inhibitor has already been administered to the pre-selected patient population when the efficacy is determined.

The invention includes method of testing the efficacy of a TNFα inhibitor for the treatment of AS comprising administering the TNFα inhibitor to a preselected patient population having AS; and determining the efficacy of the TNFα inhibitor using a baseline ASAS score of the patient population and an ASAS score of the patient population following administration of the TNFα inhibitor, wherein a ASAS70 in about 40% of the patient population indicates the TNFα inhibitor is effective for treating AS. In one embodiment, the TNFα inhibitor has already been administered to the pre-selected patient population when the efficacy is determined.

The invention also includes a method of predicting long-term efficacy of a TNFα inhibitor for treatment of AS in a human subject comprising administering the TNFα inhibitor to the subject; and predicting the long-term efficacy using a baseline C-reactive protein (CRP) concentration of the subject and the CRP concentration of the subject at about 2 weeks following administration of the TNFα inhibitor, wherein a CRP concentration decrease to a normal range indicates that the TNFα inhibitor will be effective for the long term treatment of AS. In one embodiment, the baseline CRP concentration is about 15 mg/L. In one embodiment, the TNFα inhibitor has already been administered to the pre-selected patient population when the efficacy is determined.

The invention also provides a method for improving the overall well being of a subject having AS comprising administering a TNFα inhibitor to the subject and determining the physical functioning response of the subject, wherein an improvement in the physical functioning response indicates an improvement in the overall well being of the subject. In one embodiment, the physical functioning response is determined using an index selected from the group consisting of an ASAS response, a BASDAI response, or a combination thereof. In another embodiment, the invention further comprises verifying the improvement in the overall well being of the subject using a Health Related Quality of Life (HRQL) score. In one embodiment, the HRQL score is determined using an index selected from the group consisting of a SF-36 mental summary component (SF-36 MCS) score, an AS Quality of Life (ASQoL) score, or a combination thereof.

The invention provides a method for improving the physical functioning response of a subject having AS comprising administering a TNFα inhibitor to the subject and determining the overall well being of the subject, wherein an improvement in the overall well being of the subject indicates an improvement in the overall physical functioning response of the subject. In one embodiment, the overall well being of the subject is determining using an HRQL score. In one embodiment, the HRQL score is determined using an index selected from the group consisting of a SF-36 MCS score, an ASQoL score, or a combination thereof. In one embodiment, the change in the ASQoL score is about 2 or the change in the SF-36 MCS score is >3 from baseline. In one embodiment, the invention further comprises verifying the improvement in the physical functioning response using an index selected from the group consisting of an ASAS response, a BASDAI response, or a combination thereof.

The invention includes a method for determining the efficacy of a TNFα inhibitor for improving the overall well being and physical functioning in a human subject having AS comprising
  a) administering the TNFα inhibitor to a patient population having AS; and
  b) determining the efficacy of the TNFα inhibitor using a baseline physical functioning response selected from the group consisting of an ASAS response, a BASDAI response, or a combination thereof, and a baseline overall well being response comprising an HRQL score based on an index selected from the group consisting of a SF-36 MCS score, an ASQoL score, or a combination thereof, of the patient population and a corresponding physical functioning response and overall well being response of the patient population following administration of the TNFα inhibitor, wherein the TNFα inhibitor is effective at improving the overall well being and physical functioning of the patient population if at least one of the following is achieved:
  i) the patient population has an ASAS response of at least ASAS70 and has a mean SF-36 MCS score change from baseline of at least about 14;
  ii) the patient population has an ASAS response between at least ASAS20 to less than ASAS50 and has a mean ASQoL score change from baseline of at least about −3.1;
  iii) the patient population has an ASAS response between at least ASAS50 to less than ASAS70 and a mean ASQoL score change from baseline of at least about −4.0;
  iv) the patient population has an ASAS response between at least ASAS20 to less than ASAS50 and a mean ASQoL score change from baseline of at least about −3.1;
  v) the patient population has an ASAS response of at least ASAS70 and a mean ASQoL score change from baseline of at least about −7.5;
  vi) the patient population has a BASDAI response of at least BASDAI50 to less than BASDAI70 and a mean SF-36 MCS score change from baseline of at least about 4.3;
  vii) the patient population has a BASDAI response of at least BASDAI70 and a mean SF-36 MCS score change from baseline of at least about 7.6;
  viii) the patient population has a BASDAI response of at least BASDAI50 to less than BASDAI70 and a mean SF-36 MCS score change from baseline of at least about 4.3;

ix) the patient population has a BASDAI response of at least BASDAI50 to less than BASDAI70 and a mean ASQoL score change from baseline of at least about −4.0; and x) the patient population has a BASDAI response of at least BASDAI70 and a mean ASQoL score change from baseline of at least about −6.8.

The invention also provides a method of reducing both spinal and sacroiliac (SI) joint inflammation in a human subject having AS comprising administering a TNFα inhibitor to the subject such the spinal and sacroiliac (SI) joint inflammation is reduced. In one embodiment, the reduction of spinal and SI joint inflammation is determined using magnetic resonance imaging (MRI). In another embodiment, there is at least about a 53% improvement in spine inflammation from a baseline determination to a determination at a time period following baseline. In still another embodiment, there is at least about a 54% improvement in SI joint inflammation from a baseline determination to a determination at a time period following baseline. In one embodiment, the time period following baseline is about 12 weeks.

The invention provides a method of predicting the efficacy of a TNFα inhibitor for the treatment of AS comprising administering the TNFα inhibitor to a human subject having AS; predicting the efficacy of the TNFα inhibitor using a baseline C-reactive protein (CRP) level of the human subject and a CRP level following administration of the TNFα inhibitor, wherein a reduction in the CRP level to normal levels indicates that the TNFα inhibitor is effective at treating AS.

The invention includes a method for monitoring the effectiveness of a TNFα inhibitor for the treatment of pain in a human subject having AS comprising: administering the TNFα inhibitor to the subject; and determining the effectiveness of the TNFα inhibitor using a baseline score from a pain assessment test selected from the group consisting of Total Back Pain (TBP) VAS, Nocturnal Pain (NP) VAS, and the SF-36 Bodily Pain domain and a score from the pain assessment test following administration of the TNFα inhibitor, wherein a change selected from the group consisting of about −19.5 for the TBP assessment test; about −19.2 for the NP assessment test; and about 19.2 for the SF-36 assessment test indicates that the TNFα inhibitor is effective at reducing pain in a subject having AS.

The invention further provides a method for monitoring the effectiveness of a TNFα inhibitor for the treatment of fatigue in a human subject having AS comprising: administering the TNFα inhibitor to the subject; and determining the effectiveness of the TNFα inhibitor using a either a baseline BASDAI fatigue item score or a baseline SF-36 Vitality item score and a BASDAI fatigue item score or a baseline SF-36 Vitality item score following administration of the TNFα inhibitor, wherein either a change of about −1.1 for the BASDAI fatigue item or about 13.1 for the SF-36 vitality item indicates that the TNFα inhibitor is effective at reducing fatigue in a subject having AS.

The invention also provides a method for monitoring the effectiveness of a TNFα inhibitor for treatment of enthesitis in a human subject having AS comprising: administering the TNFα inhibitor to the subject; and determining the effectiveness of the TNFα inhibitor using a baseline BASDAI enthesitis item score and a BASDAI enthesitis item score determined after administration of the TNFα inhibitor, wherein a change of about −1.79 for the BASDAI enthesitis item indicates that the TNFα inhibitor is effective at reducing enthesitis in a subject having AS.

In one embodiment, the TNFα inhibitor is a TNFα antibody, or antigen-binding portion thereof, or a fusion protein.

In one embodiment, the TNFα antibody, or antigen-binding portion thereof, is selected from the group consisting of a human antibody, a chimeric antibody, a humanized antibody, and a multivalent antibody. In one embodiment, the TNFα antibody, or antigen-binding portion thereof, is infliximab or golimumab.

In one embodiment, the human TNFα antibody, or antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less.

In one embodiment, the human TNFα antibody, or antigen-binding portion thereof, has the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment, the human TNFα antibody, or antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11.

In one embodiment, the human TNFα antibody, or antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2.

In one embodiment, the human TNFα antibody, or antigen-binding portion thereof, is adalimumab.

BRIEF DESCRIPTION OF THE FIGURES

FIGS. 35 and 36 show improvements in BASFI and BASDAI.

DETAILED DESCRIPTION OF THE INVENTION

I. Definitions

Figure 1:
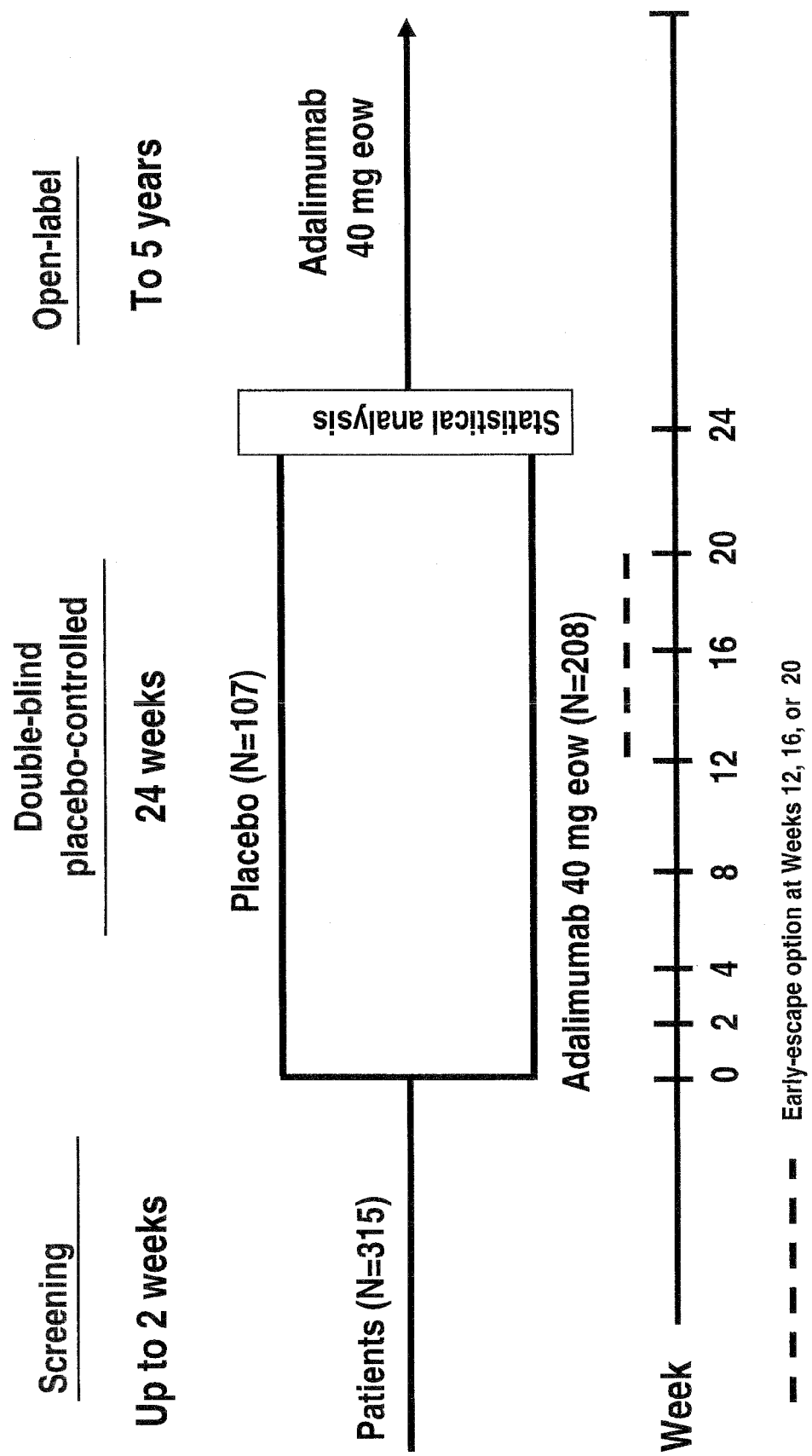
FIG. 1 graphically depicts Study H's design.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" includes agents which interfere with TNFα activity. The term also includes each of the anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356. In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA®0 Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (Enbrel®, Amgen; described in WO 91/03553 and WO 09/406,476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" or "antigen-binding fragment" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Binding fragments include Fab, Fab', F(ab')$_2$, Fabc, Fv, single chains, and single-chain antibodies. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH or VL domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Hoffiger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

Still further, an antibody or antigen-binding portion thereof may be part of a larger immunoadhesin molecules, formed by covalent or noncovalent association of the antibody or antibody portion with one or more other proteins or peptides. Examples of such immunoadhesin molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesin molecules can be obtained using standard recombinant DNA techniques, as described herein.

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In a preferred embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immunogenicity.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173, 494; PCT International Publication No. WO 86/01533; U.S. Pat. No. 4,816,567; European Patent Application No. 125, 023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314: 446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141: 4053-4060, Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693, 762, Selick et al., WO 90/07861, and Winter, U.S. Pat. No. 5,225,539.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNoFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "dose," as used herein, refers to an amount of TNFα inhibitor which is administered to a subject.

The term "dosing", as used herein, refers to the administration of a substance (e.g., an anti-TNFα antibody) to achieve a therapeutic objective (e.g., treatment of ankylosing spondylitis (AS)).

A "dosing regimen" describes a treatment schedule for a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

The terms "biweekly dosing regimen", "biweekly dosing", and "biweekly administration", as used herein, refer to the time course of administering a substance (e.g., an anti-TNFα antibody) to a subject to achieve a therapeutic objective, e.g., throughout the course of treatment. The biweekly dosing regimen is not intended to include a weekly dosing regimen. Preferably, the substance is administered every 9-19 days, more preferably, every 11-17 days, even more preferably, every 13-15 days, and most preferably, every 14 days. In one embodiment, the biweekly dosing regimen is initiated in a subject at week 0 of treatment. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in US 20030235585, incorporated by reference herein.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions. In one embodiment, a TNFα antibody is administered in combination with methotrexate for the treatment of ankylosing spondylitis.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody.

The term "treatment," as used within the context of the present invention, is meant to include therapeutic treatment, as well as prophylactic or suppressive measures, for the treatment of ankylosing spondylitis. For example, the term treatment may include administration of a TNFα inhibitor prior to or following the onset of ankylosing spondylitis thereby preventing or removing signs of the disease or disorder. As another example, administration of a TNFα inhibitor after clinical manifestation of ankylosing spondylitis to combat the symptoms and/or complications and disorders associated with ankylosing spondylitis comprises "treatment" of the disease. Further, administration of the agent after onset and after clinical symptoms and/or complications have developed where administration affects clinical parameters of the disease or disorder and perhaps amelioration of the disease, comprises "treatment" of the ankylosing spondylitis.

Those "in need of treatment" include mammals, such as humans, already having AS, including those in which the disease or disorder is to be prevented.

Various aspects of the invention are described in further detail herein.

The invention provides improved uses and compositions for treating ankylosing spondylitis with a TNFα inhibitor, e.g., a human TNFα antibody, or an antigen-binding portion thereof. Compositions and articles of manufacture, including kits, relating to the methods and uses for treating ankylosing spondylitis are also contemplated as part of the invention.

II. TNF Inhibitors

A TNFα inhibitor which is used in the methods and compositions of the invention includes any agent which interferes with TNFα activity. In a preferred embodiment, the TNFα inhibitor can neutralize TNFα activity, particularly detrimental TNFα activity which is associated with ankylosing spondylitis, and related complications and symptoms.

In one embodiment, the TNFα inhibitor used in the invention is an TNFα antibody (also referred to herein as a TNFα antibody), or an antigen-binding fragment thereof, including chimeric, humanized, and human antibodies. Examples of TNFα antibodies which may be used in the invention include, but not limited to, infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein.

Other examples of TNFα inhibitors which may be used in the methods and compositions of the invention include etanercept (Enbrel, described in WO 91/03553 and WO 09/406, 476), soluble TNF receptor Type I, a pegylated soluble TNF receptor Type I (PEGs TNF-R1), p55TNFR1gG (Lenercept), and recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

In one embodiment, the invention features uses and composition for treating or determining the efficacy of a TNFα inhibitor for the treatment of ankylosing spondylitis, wherein the TNFα antibody is an isolated human antibody, or antigen-binding portion thereof, that binds to human TNFα with high affinity and a low off rate, and also has a high neutralizing capacity. Preferably, the human antibodies used in the invention are recombinant, neutralizing human anti-hTNFα antibodies. The most preferred recombinant, neutralizing antibody of the invention is referred to herein as D2E7, also referred to as HUMIRA® or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HU-MIRA®) have been described in Salfeld et al., U.S. Pat. Nos. 6,090,382, 6,258,562, and 6,509,015, which are each incorporated by reference herein. The methods of the invention may also be performed using chimeric and humanized murine anti-hTNFβ antibodies which have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

In one embodiment, the method of the invention includes determining the efficacy of an antibody, e.g., D2E7 antibodies and antibody portions, D2E7-related antibodies and antibody portions, or other human antibodies and antibody portions with equivalent properties to D2E7, such as high affinity binding to hTNFα with low dissociation kinetics and high neutralizing capacity, for the treatment of ankylosing spondylitis. In one embodiment, the invention provides treatment with an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less. More preferably, the isolated human antibody, or antigen-binding portion thereof, dissociates from human TNFα with a $K_{off}$ of $5 \times 10^{-4}$ s$^{-1}$ or less, or even more preferably, with a $K_{off}$ of $1 \times 10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1 \times 10^{-8}$ M or less, even more preferably with an IC$_{50}$ of $1 \times 10^{-9}$ M or less and still more preferably with an IC$_{50}$ of $1 \times 10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to treating AS by administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the antibody or antigen-binding portion thereof preferably contains the following characteristics:

a) dissociates from human TNFα with a $K_{off}$ rate constant of $1 \times 10^{-3}$ $s^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ $s^{-1}$ or less. Even more preferably, the antibody, or antigen-binding portion thereof, dissociates from human TNFα with a $K_{off}$ of $1 \times 10^{-4} s^{-1}$ or less.

In yet another embodiment, the antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_\kappa I$ human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_H 3$ human germline family, more preferably from the DP-31 human germline VH gene and most preferably from the D2E7 VH framework sequences shown in FIGS. 2A and 2B of U.S. Pat. No. 6,090, 382.

Accordingly, in another embodiment, the antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention includes uses of an isolated human antibody, or an antigen-binding portions thereof, containing D2E7-related VL and VH CDR3 domains. For example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the methods and compositions of the invention may be modified for improved treatment of ankylosing spondylitis. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat ankylosing spondylitis by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion used in the methods of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesin molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H 3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e., differences in the amplified sequence as compared to the true germline sequence, for example as a result of somatic mutation), it may be desirable to change these amino acid differences back to the true germline sequences (i.e., "backmutation" of framework residues to the germline configuration).

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982)*Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, nucleic acid, vector and host cell compositions that can be used for recombinant expression of the antibodies and antibody portions used in the invention include nucleic acids, and vectors comprising said nucleic acids, comprising the human TNFα antibody adalimumab (D2E7). The nucleotide sequence encoding the D2E7 light chain variable region is shown in SEQ ID NO: 36. The CDR1 domain of the LCVR encompasses nucleotides 70-102, the CDR2 domain encompasses nucleotides 148-168 and the CDR3 domain encompasses nucleotides 265-291. The nucleotide sequence encoding the D2E7 heavy chain variable region is shown in SEQ ID NO: 37. The CDR1 domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-65; Huse et al. (1989) *Science* 246:1275-1281; McCafferty et al., *Nature* (1990) 348:552-554; Griffiths et al. (1993) *EMBO J* 12:725-734; Hawkins et al. (1992)*J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human neutralizing antibodies with high affinity and a low off rate constant for hTNFα, e.g., adalimumab, are described in U.S. Pat. Nos. 6,090,382, 6,258,562, and 6,509,015, each of which is incorporated by reference herein.

Antibodies, antibody-portions, and other TNFα inhibitors for use in the methods of the invention, can be incorporated into pharmaceutical compositions suitable for administration to a subject. Typically, the pharmaceutical composition comprises an antibody, antibody portion, or other TNFα inhibitor, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, the antibody or other TNFα inhibitor is administered by intravenous infusion or injection. In another preferred embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, the invention includes pharmaceutical compositions comprising an effective TNFα inhibitor and a pharmaceutically acceptable carrier, wherein the effective TNFα inhibitor may be used to treat ankylosing spondylitis.

In one embodiment, the antibody or antibody portion for use in the methods of the invention is incorporated into a pharmaceutical formulation as described in PCT/IB03/04502 and U.S. Appln. No. 20040033228, incorporated by reference herein. This formulation includes a concentration 50 mg/ml of the antibody D2E7 (adalimumab), wherein one pre-filled syringe contains 40 mg of antibody for subcutaneous injection.

The antibodies, antibody-portions, and other TNFα inhibitors of the present invention can be administered by a variety of methods known in the art, although for many therapeutic applications, the preferred route/mode of administration is parenteral, e.g., subcutaneous injection. In another embodiment, administration is via intravenous injection or infusion.

As will be appreciated by the skilled artisan, the route and/or mode of administration will vary depending upon the desired results in view of the teachings herein. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

In one embodiment, the TNFα antibodies and inhibitors used in the invention are delivered to a subject subcutaneously. In one embodiment, the subject administers the TNFα inhibitor, including, but not limited to, TNFα antibody, or antigen-binding portion thereof, to himself/herself.

The TNFα antibodies and inhibitors used in the invention may also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. Appln. No. 20040033228, incorporated by reference herein, are used to treat ankylosing spondylitis using the treatment methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion for use in the methods of the invention is coformulated with and/or coadministered with one or more additional therapeutic agents, including an ankylosing spondylitis inhibitor or antagonist. For example, an anti-hTNFα antibody or antibody portion of the invention may be coformulated and/or coadministered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Additional description regarding methods and uses of the invention comprising administration of a TNFα inhibitor are described in Part III of this specification.

The invention also pertains to packaged pharmaceutical compositions or kits for administering the anti-TNF antibodies of the invention for the treatment of ankylosing spondylitis. In one embodiment of the invention, the kit comprises a TNFα inhibitor, such as an antibody and instructions for administration of the TNFα inhibitor for treatment of ankylosing spondylitis. The instructions may describe how, e.g., subcutaneously, and when, e.g., at week 0, week 2, week 4, etc., the different doses of TNFα inhibitor shall be administered to a subject for treatment.

Another aspect of the invention pertains to kits containing a pharmaceutical composition comprising a TNFα inhibitor, such as an antibody, and a pharmaceutically acceptable carrier and one or more pharmaceutical compositions each comprising an additional therapeutic agent useful for treating ankylosing spondylitis, and a pharmaceutically acceptable carrier. Alternatively, the kit comprises a single pharmaceutical composition comprising an anti-TNFα antibody, one or more drugs useful for treating ankylosing spondylitis, and a pharmaceutically acceptable carrier. The instructions may describe how, e.g., subcutaneously, and when, e.g., at week 0, week 2, week 4, etc., doses of TNFα inhibitor and/or the additional therapeutic agent shall be administered to a subject for treatment.

The kit may contain instructions for dosing of the pharmaceutical compositions for the treatment of ankylosing spondylitis. Additional description regarding articles of manufacture of the invention are described in subsection III.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

III. Uses and Compositions for Treating Ankylosing Spondylitis

Ankylosing spondylitis (AS) is a chronic rheumatic disease. The sacroiliac joints are affected and, to a varying degree, the spinal column. The disease may also involve the peripheral joints and extra-articular structures. Patients commonly experience pain, morning stiffness and disability, all which generally increase with duration of disease. Systemic features, such as anorexia and fatigue may also occur. In late disease, some patients develop acute anterior uveitis, cardiovascular or pulmonary problems. Men are more commonly affected than women, and, as with other sponylarthritides, AS is associated with positivity for the HLA-B27 gene.

In one embodiment, the invention provides a method for treating ankylosing spondylitis in a subject. The invention also provides a method for achieving partial remission of a subject having AS by administering a TNFα inhibitor.

Certain subtypes of AS may be treated in accordance with the invention. In one embodiment, early axial spondylarthritis (SpA) is treated by administering a TNFα inhibitor, e.g., antibody, or antigen-binding portion thereof, to a subject. Preradiographic axial SpA is associated with chronic low back pain, and may be diagnosed based, for example, on inflammatory back pain, HLA-B27 positivity, and an MRI showing acute inflammation of spine or sacroiliac joints.

The invention provides a method for treating certain subpopulations of AS patients who may be especially difficult to treat. For example, the invention provides a method for treating patients who have failed conventional therapies known to treat AS, such as treatment with an NSAIDs or a DMARD. The invention further provides a a method of treating ankylosing spondylitis (AS) in a subject or patient who has failed prior treatment with a TNFα inhibitor, e.g., infliximab and/or etanercept, comprising administering a human TNFα antibody, or antigen-binding portion thereof, to the subject such that AS is treated.

The invention further provides a method of decreasing pain and fatigue in a subject having AS comprising administering a human TNFα antibody, or antigen-binding portion thereof, to the subject such that pain and fatigue are decreased. The invention also includes use of a human TNFα antibody, or antigen-binding portion thereof, in the manufacture of a medicament for the treatment of pain and fatigue in a subject having AS.

The invention also provides methods for improving AS in a subject based on indices used to measure the disease state. In one embodiment, the invention provides a method for decreasing the decrease in fatigue is determined by a decrease of at least about 1.1 in a BASDAI score of the subject. In one embodiment, the decrease in fatigue is determined by a decrease of at least about 2.2 in a BASDAI score of the subject. In one embodiment, the decrease in fatigue is determined by a decease of at least about 2.3 in a BASDAI score of the subject.

The invention also includes a method of inducing partial remission of AS in a subject comprising administering a human TNFα antibody, or antigen-binding portion thereof, to the subject, such that partial remission of AS is induced. The invention provides a use of a human TNFα antibody, or antigen-binding portion thereof, in the manufacture of a medicament for inducing partial remission of AS in a subject. Partial remission may be defined, in one embodiment, as sustained remission for at least 52 weeks. In one embodiment, the subject has a value of less than 20 on a scale of 0-100 in all four ASAS domains.

The invention also includes a method of achieving a decrease of at least about 50% in a spinal SPARCC score of a subject having AS comprising administering a human TNFα antibody, or antigen-binding portion thereof, to the subject such that the spinal SPARCC score is decreased by at least about 50%. In one embodiment, the invention provides a decrease of at least about 54% in the spinal SPARCC score of the subject is achieved. In another embodiment, the invention provides a decrease of at least about 57% in the spinal SPARCC score of the subject is achieved.

The invention also includes a method of achieving a decrease of at least about 51% in a joint SPARCC score of a subject having AS comprising administering a human TNFα antibody, or antigen-binding portion thereof, to the subject such that the spinal SPARCC score is decreased by at least about 50%. In one embodiment, the invention provides a method for achieving a decrease of at least about 53% in the joint SPARCC score of the subject is achieved; a decrease of at least about 59% in the joint SPARCC score of the subject is achieved.

Methods of treatment described herein may include administration of a TNFα inhibitor to a subject to achieve a therapeutic goal, e.g., improvement in ASAS domains, induction of partial remission, ASAS20, ASAS50, ASAS70 response, improvement in BASDAI score, and/or maintenance of a positive PASS response. Also included in the scope of the invention are uses of a TNFα inhibitor in the manufacture of a medicament to achieve a therapeutic goal, e.g., improvement in ASAS domains, induction of partial remission, ASAS20, ASAS50, ASAS70 response, improvement in BASDAI score, and/or maintenance of a positive PASS response. Thus, where methods are described herein, it is also intended to be part of this invention that the use of the TNFα inhibitor in the manufacture of a medicament for the purpose of the method is also considered within the scope of the invention. Likewise, where a use of a TNFα inhibitor in the manufacture of a medicament for the purpose of achieving a therapeutic goal is described, methods of treatment resulting in the therapeutic goal are also intended to be part of the invention.

In one embodiment, treatment of AS is achieved by administering a human TNFα antibody, or an antigen-binding portion thereof, to a subject having AS, wherein the human TNFα antibody, or an antigen-binding portion thereof, is administered on a biweekly dosing regimen. Biweekly dosing regimens can be used to treat disorders in which TNFα activity is detrimental, and are further described in U.S. application Ser. No. 10/163,657 (US 20030235585), incorporated by reference herein. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing is preferably administered parenterally, including subcutaneously.

In one embodiment, the invention provides a method of treating AS in a subject comprising administering a human TNFα antibody, or antigen-binding portion thereof, e.g., adalimumab, to the subject at week 0 on a biweekly dosing regimen. In one embodiment, the human TNFα antibody, or antigen-binding portion thereof, is administered subcutaneously. In one embodiment, AS is treated by administering a human TNFα antibody, or antigen-binding portion thereof, on biweekly dosing regimen for a minimum time period, e.g., at least about 12 weeks, at least about 20, at least about 26, at least about 52 weeks.

In one embodiment, the human TNFα antibody, or an antigen-binding portion thereof, is administered in a dose of about 40 mg. In one embodiment, the human TNFα antibody, or an antigen-binding portion thereof, is adalimumab.

The invention also provides pharmacokinetic parameters which have been identified as providing a therapeutic benefit to a subject having ankylosing spondylitis (AS). Certain mean steady-state trough levels of a TNFα inhibitor have be identified as corresponding to therapeutic benefits for subject having AS, including, but not limited to, partial remission of AS. The term "trough level" refers to the serum TNFα inhibitor concentration at a time after delivery of a previous dose and immediately prior to delivery of the next subsequent dose of drug in a series of doses. Generally, the trough serum concentration is a minimum sustained efficacious drug concentration in the series of drug administrations. Also, the trough serum concentration is frequently targeted as a minimum serum concentration for efficacy because it represents the serum concentration at which another dose of drug is to be administered as part of the treatment regimen. In some instances, pharmacokinetic parameters of the TNFα inhibitor may depend on additional agents administered in combination for the treatment of AS. In one embodiment, the invention provides a method of treating ankylosing spondylitis in a subject comprising administering a dose of a TNFα inhibitor, e.g., adalimumab, to the subject, wherein the dose results in a mean serum trough concentration of about 6-7 μg/mL of the TNFα inhibitor. A method of treating ankylosing spondylitis in a subject comprising administering a concomitant therapy comprising a TNFα inhibitor, e.g., adalimumab and methotrexate to the subject, wherein the concomitant therapy results in a mean serum trough concentration of about 7-9 μg/mL of the TNFα inhibitor.

Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Dosage regimens described herein may be adjusted to provide the optimum desired response, e.g., maintaining remission of AS, in consideration of the teachings herein. It is to be noted that dosage values may vary with the type and severity of AS. It is to be further understood that for any particular subject, specific dosage regimens may be adjusted over time according to the teachings of the specification and the individual need and the professional judgment of the person administering or supervising the administration of the compositions, and that dosage amounts and ranges set forth herein are exemplary only and are not intended to limit the scope or practice of the claimed invention.

Examples of other methods and uses of TNFα inhibitors for the treatment of AS are also described in U.S. Provisional Appln. Nos. 60/812,312, 60/857,352, and 60/858,328, incorporated herein by reference.

Articles of Manufacture

The invention also provides a packaged pharmaceutical composition wherein the TNFα inhibitor, e.g., TNFα antibody, is packaged within a kit or an article of manufacture. The kit or article of manufacture of the invention contains materials useful for the treatment, including induction and/or remission, prevention and/or diagnosis of AS. The kit or article of manufacture comprises a container and a label or package insert or printed material on or associated with the container which provides information regarding use of the TNFα inhibitor, e.g., a TNFα antibody, for the treatment of AS.

A kit or an article of manufacture refers to a packaged product comprising components with which to administer a TNFα inhibitor for treatment of AS. The kit preferably comprises a box or container that holds the components of the kit. The box or container is affixed with a label or a Food and Drug Administration approved label, including a protocol for administering the TNFα inhibitor. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody adalimumab (or D2E7), as described in PCT/IB03/04502 and U.S. application Ser. No. 10/222,140, incorporated by reference herein.

The term "package insert" is used to refer to instructions customarily included in commercial packages of therapeutic products, that contain information about the indications, usage, dosage, administration, contraindications and/or warnings concerning the use of such therapeutic products.

In one embodiment, the article of manufacture of the invention comprises (a) a first container with a composition contained therein, wherein the composition comprises a TNFα antibody; and (b) a package insert indicating that the TNFα antibody may be used for reducing signs and symptoms in patients with active AS.

Suitable containers for the TNFα inhibitor, e.g., a TNFα antibody, include, for example, bottles, vials, syringes, pens, etc. The containers may be formed from a variety of materials such as glass or plastic. The container holds a composition which is by itself or when combined with another composition effective for treating, preventing and/or diagnosing the condition and may have a sterile access port.

In one embodiment, the article of manufacture comprises a TNFα inhibitor, e.g., a TNFα antibody, and a label which indicates to a subject who will be administering the TNFα inhibitor about using the TNFα inhibitor for the treatment of AS. The label may be anywhere within or on the article of manufacture. In one embodiment, the article of manufacture comprises a container, such as a box, which comprises the TNFα inhibitor and a package insert or label providing information pertaining to use of the TNFα inhibitor for the treatment of AS. In another embodiment, the information is printed on a label which is on the outside of the article of manufacture, in a position which is visible to prospective purchasers.

In one embodiment, the package insert of the invention informs a reader, including a subject, e.g., a purchaser, who will be administering the TNFα inhibitor for treatment, that the TNFα inhibitor, e.g., a TNFα antibody such as adalimumab, is an indicated treatment of AS, including of moderately to severely active disease in adult patients.

In one embodiment, the article of manufacture of the invention comprises a human TNFα antibody, or antigen-binding portion thereof, and a package insert comprising instructions for administering the human TNFα antibody, or antigen-binding portion thereof, to a human subject for the treatment of adults with moderate to severe active ankylosing spondylitis who have had an inadequate response to conventional therapy, e.g., NSAIDs and/or DMARDs.

The package insert may describe certain patient populations who may respond favorably to the TNFα inhibitor within the article of manufacture. For example, the package insert may indicate that the TNFα antibody, e.g., adalimumab, may be used to treat AS in patients who have had an inadequate response to conventional therapy and/or who have lost response to or are intolerant to infliximab. In one embodiment, the invention provides an article of manufacture comprising a human TNFα antibody, or antigen-binding portion thereof, and a package insert which indicates that the human TNFα antibody, or antigen-binding portion thereof, is indicated for the treatment of adults with moderate to severe active ankylosing spondylitis who have had an inadequate response to conventional therapy, e.g., NSAIDs and/or DMARDs.

In one embodiment, the package insert of the invention describes certain therapeutic benefits of the TNFα antibody, e.g., adalimumab, including specific symptoms of AS which may be reduced by using the TNFα antibody, e.g., adalimumab. It should be noted that the package insert may also contain information pertaining to other disorders which are treatable using the TNFα antibody, e.g., adalimumab. Information described herein which is provided in a package insert and pertains to other disorders, i.e., diseases other than AS, is also included within the scope of the invention. The package insert of the invention may indicate that extra TNFα in your body can attack normal healthy body tissues and cause inflammation especially in the tissues in your bones, cartilage, joints and digestive tract. The package insert of the invention may also indicate that adalimumab helps reduce the signs and symptoms of immune diseases, including rheumatoid and psoriatic arthritis (pain and swollen joints), ankylosing spondylitis (morning stiffness and back pain), and Crohn's disease (abdominal pain and diarrhea).

In another embodiment, the package insert of the invention describes the dose and administration of adalimumab, for the treatment of AS. The label may indicate that the recommended dose for the treatment of AS with adalimumab is 40 mg administered every other week. In one embodiment, the package insert of the invention indicates that adalimumab is administered by subcutaneous injection.

The package insert of the invention may also provide information to subjects who will be receiving adalimumab regarding combination uses for both safety and efficacy purposes. The package insert of the invention may contain warnings and precautions regarding the use of the TNFα inhibitor, e.g., a TNFα antibody such as adalimumab.

The label of the invention may further contain information regarding the use of the TNFα inhibitor, e.g., a TNFα antibody such as adalimumab, in clinical studies for AS. In one embodiment, the label of the invention describes the studies described herein as the Examples, either as a whole or in portion.

The label of the invention may contain information regarding the pharmacodynamics of the TNFα inhibitor, e.g., a TNFα antibody such as adalimumab.

In one embodiment of the invention, the kit comprises a TNFα inhibitor, such as an antibody, an second pharmaceutical composition comprising an additional therapeutic agent, and instructions for administration of both agents for the treatment of AS. The instructions may describe how, e.g., subcutaneously, and when, e.g., at week 0, week 2, and biweekly thereafter, doses of TNFα antibody and/or the additional therapeutic agent shall be administered to a subject for treatment.

Another aspect of the invention pertains to kits containing a pharmaceutical composition comprising an anti-TNFα antibody and a pharmaceutically acceptable carrier and one or more additional pharmaceutical compositions each comprising a drug useful for treating ankylosing spondylitis, and a pharmaceutically acceptable carrier. Alternatively, the kit comprises a single pharmaceutical composition comprising an anti-TNFα antibody, one or more drugs useful for treating a ankylosing spondylitis, and a pharmaceutically acceptable carrier. The kits further contain instructions for dosing of the pharmaceutical compositions for the treatment of ankylosing spondylitis.

The package or kit alternatively may contain the TNFα inhibitor and it may be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

Additional Therapeutic Agents

Methods, uses, and compositions of the invention also include combinations of TNFα inhibitors, including antibodies, and other therapeutic agents. TNFα inhibitors, including antibodies, or antigen binding portions thereof, can be used alone or in combination with additional agents to treat AS. It should be understood that antibodies, or antigen binding portion thereof, can be used alone or in combination with an additional agent, e.g., a therapeutic agent, said additional agent being selected by the skilled artisan for its intended purpose in consideration of the teachings herein. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

TNFα inhibitors described herein may be used in combination with additional therapeutic agents such as a Disease Modifying Anti-Rheumatic Drug (DMARD) or a Nonsteroidal Antiinflammatory Drug (NSAID) or a steroid or any combination thereof. Preferred examples of a DMARD are hydroxychloroquine, leflunomide, methotrexate, parenteral gold, oral gold and sulfasalazine. Preferred examples of non-steroidal anti-inflammatory drug(s) also referred to as NSAIDS include drugs like ibuprofen. Other preferred combinations are corticosteroids including prednisolone; the well known side effects of steroid use can be reduced or even eliminated by tapering the steroid dose required when treating patients in combination with the anti-TNFα antibodies of this invention. Non-limiting examples of therapeutic agents for ankylosing spondylitis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists/inhibitors such as soluble p55 or p75 TNF receptors, derivatives, thereof, (p75TNFR1gG (Enbrel™) or p55TNFR1gG (Lenercept), chimeric, humanized or human TNF antibodies, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451, 983; and 6,448,380, each of which is incorporated by reference herein. Other combinations including TNFα converting enzyme (TACE) inhibitors; IL-1 inhibitors (Interleukin-1-converting enzyme inhibitors, IL-IRA etc.) may be effective for the same reason. Other combinations include the IL-6 antibody tocilizumab (Actemra). Other preferred combinations include Interleukin 11. Yet another preferred combination are other key players of the autoimmune response which may act parallel to, dependent on or in concert with TNFα function; especially preferred are IL-18 antagonists including IL-18 antibodies or soluble IL-18 receptors, or IL-18 binding proteins. It has been shown that TNFα and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The TNFα inhibitors, including antibodies, or antigen binding portions thereof, used in the invention may also be combined with agents, such as methotrexate, 6-MP, azathioprine sulphasalazine, mesalazine, olsalazine chloroquinine/hydroxychloroquine, penicillamine, aurothiomalate (intramuscular and oral), azathioprine, colchicine, corticosteroids (oral, inhaled and local injection), beta-2 adrenoreceptor agonists (salbutamol, terbutaline, salmeterol), xanthines (theophylline, aminophylline), cromoglicate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g. IRAK, NIK, IKK, p38 or MAP kinase inhibitors), IL-1β converting enzyme inhibitors, TNFα, converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), tocilizumab (Actemra), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe AS cases, cyclosporine.

The TNFα inhibitor used in the methods and compositions of the invention may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists.

Non-limiting examples of therapeutic agents for AS with which TNFα inhibitor, such as an antibody, or antibody portion, can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab.

Non-limiting examples of therapeutic agents for Ankylosing Spondylitis with which an antibody, or antibody portion, of the invention can be combined include the following: ibuprofen, diclofenac and misoprostol, naproxen, meloxicam, indomethacin, diclofenac, celecoxib, rofecoxib, Sulfasalazine, Methotrexate, azathioprine, minocycline, prednisone, etanercept, infliximab. In one embodiment, the methods of the invention include the combination of a TNFα inhibitor and methotrexate.

IV. Efficacy of TNFα Inhibitor

The invention also provides methods for determining whether a TNFα inhibitor is effective at treating AS in a subject. Such methods may be used to determine the efficacy of a TNFα inhibitor, including those which are unknown or unconfirmed to have such efficacy. Using the methods described herein, effective TNFα inhibitors may be determined or confirmed, and, subsequently, used in the method of treating AS.

Methods of determining efficacy of a TNFα inhibitor for treating ankylosing spondylitis (AS) in a subject include any means known in the art. The clinical course of AS is measured by using any number of instruments to evaluate various AS symptoms. Some of the commonly used scales include the Assessment in Ankylosing Spondylitis (ASAS), the Bath Ankylosing Spondylitis Disease Activity Index (BASDAI) (Garrett et al. (1994) *J Rheumatol* 21:2286), the Bath Ankylosing Spondylitis Metrology Index (BASMI) (Jenkinson et al. (1994) *J Rheumatol* 21:1694), the Patient Acceptable Symptom State (PASS), and the Bath Ankylosing Spondylitis Functional Index (BASFI) (Calin et al. (1994) *J Rheumatol* 21:2281). These indices can be used to monitor a patient over time and to determine improvement. Each of these scales is described further below as examples of criteria which may be used to measure the clinical course of AS.

The Assessment in Ankylosing Spondylitis (ASAS20) may be used as an endpoint, including as a primary endpoint, for determining the efficacy of AS. An ASAS20 indicates a ≥20% improvement and absolute improvement of ≥10 units (scale of 0-100) in ≥3 of 4 domains: Subject Global Assessment, Pain, Function, and Inflammation. There must be an absence of deterioration in the potential remaining domain (deterioration is defined as a change for the worse of ≥20% and a net worsening of ≥10 units (scale of 0-100).

The Bath Ankylosing Spondylitis Disease Activity Index (BASDAI) may be used to evaluate the level of disease activity in a patient with AS. BASDAI focuses upon signs and symptoms of the inflammatory aspects of AS, nocturnal and total back pain, the patient's global assessment and actual physical measurements of spinal mobility such as the Schober's test, chest expansion score and occiput to wall measurement. BASDAI measures disease activity on the basis of six questions relating to fatigue, spinal pain, peripheral arthritis, enthesitis (inflammation at the points where tendons/ligaments/joint capsule enter the bone), and morning stiffness. These questions are answered on a 10-cm horizontal visual analog scale measuring severity of fatigue, spinal and peripheral joint pain, localized tenderness, and morning stiffness (both qualitative and quantitative). The final BASDAI score has a range of 0 to 10.

The Bath Ankylosing Spondylitis Functional Index (BASFI) measures the physical function impairment caused by AS, and is a self-assessment instrument that consists of 8 specific questions regarding function in AS, and 2 questions reflecting the patient's ability to cope with everyday life. Each question is answered on a 10-cm horizontal visual analog scale, the mean of which gives the BASFI score (0-10).

The Bath Ankylosing Spondylitis Metrology Index (BASMI) consists of 5 simple clinical measurements that provide a composite index and define disease status in AS. Analysis of metrology (20 measurements) identified these 5 measurements as most accurately reflecting axial status: cervical rotation, tragus to wall distance, lateral flexion, modified Schober's test, and internalleolar distance. The BASMI is quick (7 minutes), reproducible, and sensitive to change across the entire spectrum of disease. The BASMI index comprises 5 measures of hip and spinal mobility in AS. The five BASMI measures, scaled 0 (mild) to 10 (severe), include tragus to wall distance, cervical rotation, lumbar flexion, lumbar side flexion, and intermolecular distance.

Patient Acceptable Symptom State (PASS) is a method for assessing whether the patient (pt) considers his/her overall disease state satisfactory, and provides a method which considers the individual patient response. The PASS concept requires only that the clinician asks the patient a single question requiring a yes or no answer: "Considering all the different ways your disease is affecting you, if you would stay in this state for the next months, do you consider that your current state is satisfactory?" Achievement of PASS indicates that a patient feels well, and assessment of PASS, therefore, is a simple measure to determine whether a patient has achieved therapeutic success, including in a clinical trial or in clinical practice. Use of the PASS concept in addition to other patient-reported outcome measures has been described in a few chronic rheumatic conditions (Tubach et al. Ann Rheum Dis 2005; 64:29-33; Dougados et al. Arthritis Res Ther 2007; 9:R11) and acute pain conditions (Tubach et al. Arthritis Rheum 2006; 55:526-30; Dougados et al. PLoS Clin Trials 2007; 2:e9).

Combinations of the above-mentioned criteria may be used to evaluate patients progress with a TNF inhibitor in accordance with the invention. In addition, radiographic, MRI, and bone and cartilage degradation markers may also be used to determine disease activity in AS patients.

In one embodiment, the invention provides a method for determining efficacy using a Bath Ankylosing Spondylitis Disease Activity Index (BASDAI) 20 response. The invention includes a method of determining the efficacy of a TNFα inhibitor for treating ankylosing spondylitis (AS) in a subject comprising determining a Bath Ankylosing Spondylitis Disease Activity Index (BASDAI) 20 response of a patient population having AS and who was administered the TNFα inhibitor, wherein an BASDAI 20 response in at least about 80% of the patient population indicates that the TNFα inhibitor is an effective TNFα inhibitor for the treatment of AS in a subject. The invention further provides a method of treating AS in a subject comprising administering an effective TNFα inhibitor to the subject such that AS is treated, wherein the effective TNFα inhibitor was previously identified as resulting in a BASDAI 20 response in at least about 80% of a patient population having AS and who was administered the TNFα inhibitor.

The invention also includes a method of determining the efficacy of a TNFα inhibitor for treating ankylosing spondylitis (AS) in a subject comprising determining a Bath Ankylosing Spondylitis Disease Activity Index (BASDAI) 50 response of a patient population having AS and who was administered the TNFα inhibitor, wherein an BASDAI 50 response in at least about 67% of the patient population indicates that the TNFα inhibitor is an effective TNFα inhibitor for the treatment of AS in the subject. In one embodiment, an BASDAI 50 response in at least about 20%, at least about 42%, or at least about 45%, of the patient population indicates that the TNFα inhibitor is an effective TNF inhibitor for the treatment of AS in the subject. In one embodiment, an BASDAI 50 response in at least about 20%, 21% 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, of the patient population indicates that the TNFα inhibitor is an effective TNF inhibitor for the treatment of AS in the subject.

The invention further provides a method of determining the efficacy of a TNFα inhibitor for treating ankylosing spondylitis (AS) in a subject comprising determining a Bath Ankylosing Spondylitis Disease Activity Index (BASDAI) 70 response of a patient population having AS and who was administered the TNFα inhibitor, wherein an BASDAI 70 response in at least about 27% of the patient population indicates that the TNFα inhibitor is an effective TNFα inhibitor for the treatment of AS in the subject.

The invention provides a method of treating AS in a subject comprising administering an effective TNFα inhibitor to the subject such that AS is treated, wherein the effective TNFα inhibitor was previously identified as resulting in an ASAS20 response in at least about 61% of a patient population having AS who was administered the TNFα inhibitor. In one embodiment, an ASAS20 response in at least about 42%, at least about 51%, at least about 58%, at least about 59%, at least about 62%, at least about 73%, or at least about 75% of the patient population indicates that the TNFα inhibitor is an effective TNFα inhibitor for the treatment of AS in the subject. In one embodiment, an ASAS20 response in at least about 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73% 74%, 75%, 76%, of the patient population indicates that the TNFα inhibitor is an effective TNFα inhibitor for the treatment of AS in the subject The invention also includes a method of determining the efficacy of a TNFα inhibitor for treating ankylosing spondylitis (AS) in a subject comprising determining a Assessment in Ankylosing Spondylitis (ASAS) response of a patient population having AS and who was administered the TNFα inhibitor, wherein an ASAS20 response in at least about 61% of the patient population indicates that the TNFα inhibitor is an effective TNFα inhibitor for the treatment of AS in the subject. In one embodiment, an ASAS20 response in at least about 70% of the patient population indicates that the TNFα inhibitor is an effective TNFα inhibitor for the treatment of AS in the subject. In one embodiment, an ASAS20 response in at least about 73% of the patient population indicates that the TNFα inhibitor is an effective TNFα inhibitor for the treatment of AS in the subject. In one embodiment, an ASAS20 response in at least about 75% of the patient population indicates that the TNFα inhibitor is an effective TNFα inhibitor for the treatment of AS in the subject. In one embodiment, an ASAS20 response in at least about 61%, 62%, 63%, 64%, 65%, 66%, 67%, 68%, 69%, 70%, 71%, 72%, 73%, 74%, or 75% of the patient population indicates that the TNFα inhibitor is an effective TNFα inhibitor for the treatment of AS in the subject The invention also provides a method of determining the efficacy of a human TNFα antibody, or antigen-binding portion thereof, or for treating ankylosing spondylitis (AS) in a subject comprising determining a Assessment in Ankylosing Spondylitis (ASAS) 50 response of a patient population having AS and who was administered the human TNFα antibody, or antigen-binding portion thereof, wherein an ASAS50 response in at least about 16% of the patient population indicates that the human TNFα antibody, or antigen-binding portion thereof, is an effective human TNFα antibody, or antigen-binding portion thereof, for the treatment of AS in the subject. In one embodiment, an ASAS50 response in at least about 20% of the patient population indicates that the human TNFα antibody, or antigen-binding portion thereof, is an effective human TNFα antibody, or antigen-binding portion thereof, for the treatment of AS in the subject. In one embodiment, an ASAS50 response in at least about 30% of the patient population indicates that the human TNFα antibody, or antigen-binding portion thereof, is an effective human TNFα antibody, or antigen-binding portion thereof, for the treatment of AS in the subject. In one embodiment, an ASAS50 response in at least about 38% of the patient population indicates that the human TNFα antibody, or antigen-binding portion thereof, is an effective human TNFα antibody, or antigen-binding portion thereof, for the treatment of AS in the subject. In one embodiment, an ASAS50 response in at least about 16%, at least about 35%, or at least about 28% of the patient population indicates that the TNFα inhibitor is an effective TNFα inhibitor for the treatment of AS in the subject. In one embodiment, an ASAS50 response in at least about 16%, 17%, 18%, 19%, 20%, 21%, 22%, 23%, 24%, 25%, 26%, 27%, 28%, 29%, 30%, 31%, 32%, 33%, 34%. 35%, 36%, 37%, or 38% the patient population indicates that the TNFα inhibitor is an effective TNFα inhibitor for the treatment of AS in the subject.

The invention also includes a method of determining the efficacy of a human TNFα antibody or for treating ankylosing spondylitis (AS) in a subject comprising determining a Assessment in Ankylosing Spondylitis (ASAS) 70 response of a patient population having AS and who was administered the human TNFα antibody, or antigen-binding portion thereof, wherein an ASAS70 response in at least about 7% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 20% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 23% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 30% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 40% of the patient population indicates that the human TNFα antibody, or antigen-binding portion thereof, is an effective human TNFα antibody, or antigen-binding portion thereof, for the treatment of AS in the subject. In one embodiment, an ASAS70 response in at least about 7%, at least about 23%, at least about 24%, or at least about 40% of the patient population indicates that the TNFα inhibitor is an effective TNFα inhibitor for the treatment of AS in the subject. In one embodiment, an ASAS70 response in at least about 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%. 35%, 36%, 37%, 38%, 39%, or 40% of the patient population indicates that the TNFα inhibitor is an effective TNFα inhibitor for the treatment of AS in the subject.

The invention also includes a method of determining the efficacy of a TNFα inhibitor for treating ankylosing spondylitis (AS) in a subject comprising determining a Patient Acceptable Symptom State (PASS) response of a patient population having AS and who was administered the TNFα inhibitor, wherein a PASS response of "yes" in at least about 29% or higher of the patient population indicates that the TNFα inhibitor is an effective TNFα inhibitor for the treatment of AS in a subject.

Numbers intermediate to any percentages recited herein, including those in the Examples, e.g., 61%, 62%, 63%. 64%, 65%, 66%, 67%, 68%, 69%, are also intended to be part of this invention. Ranges of values using a combination of any of the above recited values as upper and/or lower limits are intended to be included in the scope of the invention The invention also includes administering the effective human TNFα antibody, or antigen-binding portion thereof, described herein to a subject to treat AS.

Also encompassed in the invention is a method of treatment comprising administering a TNFα inhibitor shown to be efficacious according to the methods described herein and in the Examples. In one embodiment, the methods of the invention comprise administering the TNFα inhibitor to the subjects of a patient population and determining the efficacy of the TNFα inhibitor by determining changes, improvements, measurements, etc., using AS known in the art, in the patient population in comparison to the Examples set forth below. For example, the invention further provides a method of treating AS in a subject comprising administering an effective TNFα inhibitor to the subject such that AS is treated, wherein the effective TNFα inhibitor was previously identified as resulting in a BASDAI 50 response in at least about 67% of a patient population having AS and who was administered the TNFα inhibitor. The invention further provides a treating AS in a subject comprising administering an effective TNFα inhibitor to the subject such that AS is treated, wherein the effective TNFα inhibitor was previously identified as resulting in a BASDAI 70 response in at least about 27% of a patient population having AS and who was administered the TNFα inhibitor.

The invention also includes a method of treating AS in a subject comprising administering an effective human TNFα antibody, or antigen-binding portion thereof, to the subject, wherein the effective human TNFα antibody, or antigen-binding portion thereof, was previously identified as achieving an ASAS50 response in at least about 16% of a patient population having AS who was administered the human TNFα antibody, or antigen-binding portion thereof. The invention further describes a method of treating AS in a subject comprising administering an effective human TNFα antibody, or antigen-binding portion thereof, to the subject, wherein the effective human TNFα antibody, or antigen-binding portion thereof, was previously identified as achieving an ASAS70 response in at least about 23% of a patient population having AS who was administered the human TNFα antibody, or antigen-binding portion thereof.

The invention further provides a method of treating AS in a subject comprising administering an effective TNFα inhibitor to the subject such that AS is treated, wherein the effective TNFα inhibitor was previously identified providing a "yes" PASS response in at least about 29% of a patient population having AS and who was administered the TNFα inhibitor.

Numbers intermediate to any percentages recited herein, including those in the Examples, e.g., 61%, 62%, 63%. 64%, 65%, 66%, 67%, 68%, 69%, are also intended to be part of this invention. Ranges of values using a combination of any of the above recited values as upper and/or lower limits are intended to be included in the scope of the invention.

It should be noted that the Examples provided herein represent different methods of determining the efficacy of a TNFα inhibitor, such as a human TNFα antibody, or antigen-binding portion thereof. As such, data and results described in the Examples section which shows efficacy of a TNFα inhibitor, e.g., ability to treat AS, are included in the methods of determining efficacy of the invention.

Time points for determining efficacy will be understood by those of skill in the art to depend on the type of efficacy being determined in consideration of the teachings herein, e.g., induction of partial remission. In one embodiment, measurements in scores, e.g., an improvement in the ASAS20 response, may be measured against a subject's baseline score. Generally, a baseline refers to a measurement or score of a patient before treatment, i.e. week 0. Other time points may also be included as a starting point in determining efficacy, however.

Patient populations described in the methods of the invention are generally selected based on common characteristics, such as, but not limited to, subjects diagnosed with AS. Such a patient population would be appropriate, for example, for determining the efficacy of the TNFα inhibitor for inducing partial remission in AS in the given patient population. In one embodiment, the patient population is an adult population.

In one embodiment, the methods of the invention for determining whether a TNFα inhibitor is an effective TNFα inhibitor, include determining changes, improvements, measurements, etc., in AS using appropriate indices known in the art, e.g., ASAS responses, BASDAI, from a patient population who has already been administered the TNFα inhibitor. Such a patient population may be pre-selected according to common characteristics, e.g., AS, and may have already been given the TNFα inhibitor. Administration of the TNFα inhibitor may or may not be performed by the same person of ordinary skill who is determining the efficacy of the TNFα inhibitor in accordance with the teachings of the specification.

Methods of the invention relating to determining efficacy, i.e., determining whether a TNFα inhibitor is an effective TNFα inhibitor, may also be applied to specific patient populations within the overall patient population who together have specific, common characteristics, i.e., a subpopulation. In addition, while the above methods are described in terms of patient populations, methods of efficacy described herein may also be applied to individual subjects.

The Examples and discoveries described herein are representative of a TNFα inhibitor, i.e., adalimumab, which is effective for treating AS, including reducing pain and fatigue and inducing partial remission of AS. As such, the studies and results described in the Examples section herein may be used as a guideline for determining the efficacy of a TNFα inhibitor, i.e., whether a TNFα inhibitor is an effective TNFα inhibitor for the treatment of AS. In one embodiment, methods of determining efficacy described herein may be used to determine whether a TNFα inhibitor is bioequivalent to another TNFα inhibitor.

In one embodiment, the article of manufacture of the invention comprises instructions regarding how to determine the efficacy of the TNF inhibitor for the treatment of AS.

The present invention is further illustrated by the following examples which should not be construed as limiting in any way.

Example 1

Pharmacokinetics of Adalimumab in Patients with Active Ankylosing Spondylitis (AS)

Ankylosing spondylitis (AS) is a chronic, inflammatory, progressive disease with considerable impact on patient functional status and well-being that affects the axial skeleton, large peripheral joints, and enthuses that results in restricted spinal mobility. The mechanism of action of adalimumab for AS indication is anti-TNF mediated.

This study evaluated adalimumab exposure, immunogenicity, and the potential impact of immunogenicity on efficacy and safety in patients with active AS treated with adalimumab.

Study H was a trial using adalimumab evaluating long-term efficacy and safety in AS, and was a randomized, placebo-controlled, Phase III study involving patients ≥18 years of age with AS, based on modified New York criteria, who had a inadequate response or intolerance to 1 NSAID and might have failed one or more DMARDs. Active AS, was as diagnosed by 2 of the 3 following symptoms: Bath AS Disease Activity Index (BASDAI) score 4; Visual Analog Scale (VAS) score for total back pain 4; and morning stiffness ≥1 hour.

Patients were randomized to either subcutaneous adalimumab 40 mg every other week (eow) or placebo for 24 weeks. Patients failing to achieve ASAS 20 at Week 12, 16, or 20 were allowed to switch to open-label 40 mg eow (early escape therapy). Blood samples were collected for the evaluation of adalimumab and AAA concentrations at Weeks 0 (Baseline), 12, and 24 (See FIG. 1). Trough serum samples for adalimumab and anti-adalimumab antibody (AAA) assays were obtained at the Baseline, Week 12 and Week 24 visits to determine serum concentrations using validated ELISA methods.

Pearson's Chi-Square test was used to compare the treatment difference between adalimumab and placebo. Any patient receiving early escape therapy was treated as a non-responder at all subsequent visits. Descriptive statistics for serum adalimumab concentration data were calculated.

Among the total 315 patients enrolled, 208 were randomized to the adalimumab arm; 204 of these 208 had adalimumab and AAA concentration measurements. 155 (49%) received early escape therapy, 296 (94%) completed the 24-week period (See Table 1).

TABLE 3

Summary Statistics of Serum Adalimumab Pre-Dose Concentrations

|  | Week 12 | | Week 24 | |
| --- | --- | --- | --- | --- |
|  | With MTX | Without MTX | With MTX | Without MTX |
| N | 18 | 178 | 17 | 170 |
| Mean ± SD (µg/mL) | 6.9 ± 3.5 | 6.4 ± 4.2 | 8.6 ± 3.7 | 7.4 ± 5.1 |
| Range* (µg/mL) | 0.0-13.6 | 0.0-20.6 | 0.0-14.4 | 0.0-23.0 |

A patient was classified as AAA+ if he or she tested AAA+ at either Week 12 or Week 24. The incidence of positive AAA was 8.3% (17 of 204) in patients treated with adalimumab: 8.6% (16 of 185) in patients on monotherapy; 5.3% (1 of 19) in patients with concomitant MTX.

Figure 2:
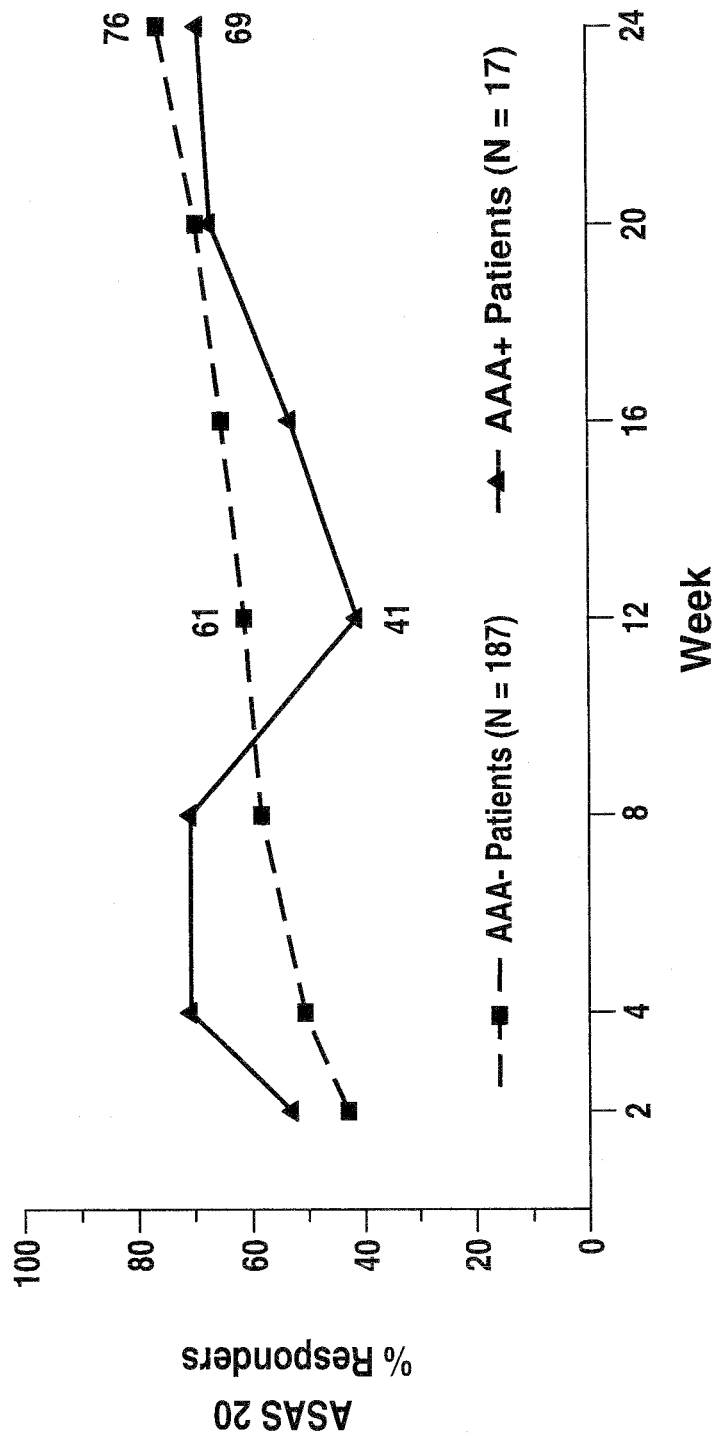
FIG. 2 shows observed ASAS 20% responders in adalimumab-treated patients (n=204) for patients in the study of example 1.

FIG. 2 displays the impact of immunogenicity on efficacy. At Week 12, ASAS 20 response rate in AAA+ patients (41%) was lower than that in AAA− patients (61%). While Week 24, ASAS 20 response rates in AAA+ patients (69%) and AAA− patients (76%) were similar. Overall, the number of AAA+ patients (N=17) was too small for adequate assessment of the impact of immunogenicity on efficacy.

TABLE 1

|  | Placebo | | | Adalimumab 40 mg eow | | | |
| --- | --- | --- | --- | --- | --- | --- | --- |
|  | Completed BP (N = 33) n (%) | Received EET (N = 74) n (%) | Total (N = 107) n (%) | Completed BP (N = 127) n (%) | Received EET (N = 81) n (%) | Total (N = 208) n (%) | Total (N = 315) n (%) |
| Completed Week 24 | 29 (87.9) | 72 (97.3) | 101 (94.4) | 120 (94.5) | 75 (92.6) | 195 (93.8) | 296 (94.0) |
| Prematurely Discontinued | 4 (12.1) | 2 (2.7) | 6 (5.6) | 7 (5.5) | 6 (7.4) | 13 (6.3) | 19 (6.0) |

BP = Blinded period.
EET = Early escape therapy

TABLE 2

Demographic characteristics were similar between placebo and adalimumab groups

|  | Treatment | |
| --- | --- | --- |
|  | Placebo (N = 107) | Adalimumab 40 mg eow (N = 208) |
| Mean Age (yr) | 43 | 42 |
| Range | 18-71 | 19-71 |
| Mean Weight (kg) | 80 | 82 |
| Range | 46-158 | 47-143 |
| Mean Duration of AS (yr) | 10 | 11 |
| % Male | 74 | 75 |
| % Caucasian | 93 | 97 |

Figure 3:
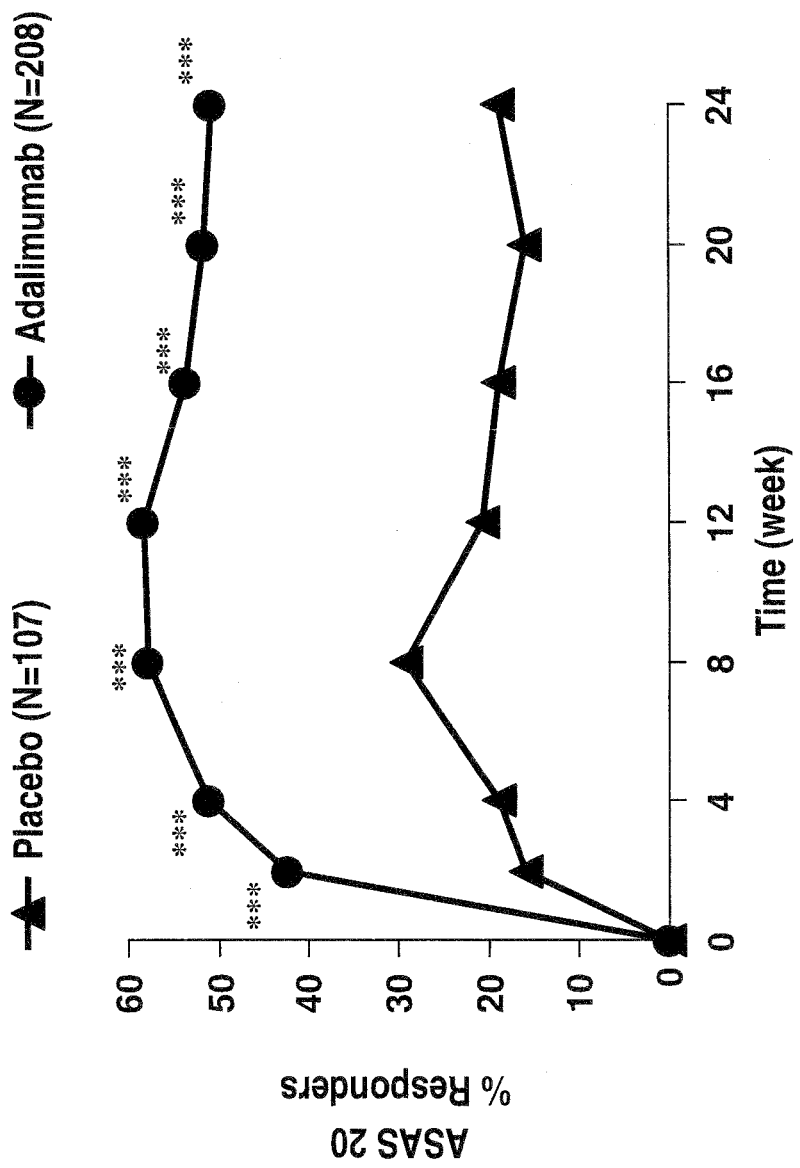
FIG. 3 graphically depicts the time course of ASAS 20—imputed patients in the study of example 1.

The Impact of Immunogenicity on Safety was assessed. Among adalimumab-treated patients, seven had injection site reactions, six were AAA− and one was AAA+. Thirteen patients discontinued during the 24-week study period, and only one was AAA+ and discontinued due to withdrawal of consent. There was no indication that there were any differences in safety between adalimumab-treated patients who developed AAA vs. those who did not Adalimumab is effective in patients with active AS (FIG. 3). During the active treatment, the mean trough concentrations of adalimumab were approximately 6-7 µg/mL for monotherapy (i.e., without MTX) and 7-9 µg/mL with concomitant MTX. (See Table 4) These concentrations were within the range of what was observed in rheumatoid arthritis (5 µg/mL for monotherapy and 8-9 µg/mL with concomitant MTX). Overall, the AAA+ rate for adalimumab-treated patients was 8.3% (17 of 204 patients). When patients were on monotherapy, the AAA+ rate was 8.6% (16 of 185 patients). Patients on concomitant MTX had an AAA+ rate of 5.3% (1 of 19 patients).

TABLE 4

Mean SD PreDose Serum Adalimumab Concentrations (N = 204)

| | Adalimumab Concentration (μg/ml) |
|---|---|
| Week 12 | |
| +MTX | 7.5 |
| No MTX | 6.5 |
| Week 24 | |
| +MTX | 8.5 |
| No MTX | 7.5 |

A total of 204 patients received at least one dose of adalimumab and had serum samples taken at either week 12 or week 24. For MTX samples, N = 16 for week 12 and N = 17 for week 24. For samples with no MTX, N = 178 for week 12 and N = 170 for week 24.

At Week 24, ASAS20 response rate was 68.8% for AAA+ patients and 76.0% for AAA− patients. There were no cases of anaphylaxis and no difference in incidence of urticaria between adalimumab-treated patients who developed AAA vs. those who did not.

In conclusion, adalimumab exposure in active AS was within the range of what was observed in rheumatoid arthritis. AAA+ rate was low and not associated with increased adverse events during the 24-week treatment period.

Example 2

Long-Term Efficacy and Safety of Adalimumab in the Treatment of Active Ankylosing Spondylitis Results of an Open-Label, 2-Year Trial The tumour necrosis factor (TNF) antagonist adalimumab has been shown to be highly efficacious in the short-term treatment of ankylosing spondylitis (AS) (Haibel et al. Arthritis Rheum 2006; 54:678). The objective of this study was to examine the therapeutic effects of adalimumab in a subpopulation of hard to treat patients, i.e., NSAID-refractory AS patients.

Fifteen patients (9 males, 6 females; mean age 40 years, range 19-55; mean disease duration 11 years, range 2-33; 86% HLA-B27 positive) with active disease (mean Bath Ankylosing Spondylitis Activity Index or BASDAI of 6.6, range 4.7-8.5) enrolled in the trial. All patients suffered from spinal pain, and 4 patients also had peripheral arthritis. Adalimumab 40 mg was administered subcutaneously every other week (eow). Clinical outcome assessments included disease activity (BASDAI), function (BASFI), metrology (BASMI), patient's and physician's global and nocturnal assessments of pain (NRS), peripheral joint assessment, Maastricht enthesitis score, quality of life (SF-36), and C-reactive protein (CRP) concentration. The primary endpoint of this study was improvement of disease activity (BASDAI50) at Week 12.

In the study, ten of the 15 patients completed the full 2 years therapy. Results show that after 2 years, the BASDAI showed significant improvements: BASDAI20% in 80% of patients; BASDAI50 in 67% of patients; and BASDIA70 in 27% of patients. Similar levels of improvement were observed via the Assessment of Ankylosing Spondylitis (ASAS) Working Group improvement criteria: ASAS20 in 73%, ASAS40 in 60%, ASAS70 in 40%, and ASAS criteria for partial remission in 27% of patients. Mean CRP concentration decreased from 15.1 mg/L at baseline to normal ranges by Week 2, and remained within normal ranges during the 2 years of follow-up. In addition, the BASFI, patient's and physician's global assessments, general and nocturnal assessments of pain (NRS), BASMI, morning stiffness (BASDAI Questions 4 and 5) all showed significant improvements.

Five patients withdrew from the study over time: one after 8 weeks for personal reasons, one for inefficacy and remitting minor infections at Week 28, one for inefficacy at Week 52, one for a flare of Crohn's disease at Week 88, and one for non-compliance. Adalimumab was well-tolerated throughout the 2-year trial. Three serious adverse events were reported: one flare of AS, one inguinal hernia, and one flare of Crohn's disease.

In conclusion, this 2-year, open-label study demonstrated that patients receiving adalimumab showed significant and sustained improvements of the spinal symptoms of active AS. Improvements were seen in patients' physical function.

Example 3

Improvements in Health Related Quality of Life (HRQL) Correlate Positively with Clinical Reponses in Ankylosing Spondylitis (AS) Patients A study was performed to evaluate the relationship between clinical response criteria (treatment efficacy) and HRQL improvements in patients with active AS.

Data were from Study H, a Phase III study in which patients were randomized to either adalimumab (ADA) 40 mg every other week or placebo (PBO) for 24 weeks. Early-escape option to open-label 40 mg adalimumab sc eow was available at Week 12, or 16, or 20 (see FIG. 1 for Study H design). For this analysis, patients were categorized into mutually exclusive groups by Assessment in Ankylosing Spondylitis (ASAS) 20/50/70 or Bath Ankylosing Spondylitis Disease Activity Index (BASDAI) 20/50/70 criteria, based on Week 12 visit data. HRQL measures include baseline (BL) and Week 12 data of the SF-36 Health Survey and the AS Quality of Life (ASQoL). A change of ≥3 for SF-36 physical summary component (PCS) or mental summary component (MCS) scores and a change of 2 in ASQoL were considered clinical meaningful.

The Clinical Response Criteria was assessed via ASAS, which measures subject's global assessment, pain, function, and inflammation; ASAS20 categorized by improvement of ≥20% and absolute improvement of ≥10 units (on a scale of 0-100) from baseline in ≥3 of the 4 domains, without deterioration in the potential remaining domain; deterioration is defined as a change for the worse of ≥20% and net worsening of ≥10 units (on a scale of 0-100). ASAS50 and ASAS70 were measured based on the same criteria as ASAS20, except measuring improvement from baseline of ≥50% and ≥70%, respectively, and absolute improvement of ≥20 units and ≥30 units, respectively.

ASAS40 was also assessed (modification of the definition used by the ASAS International Working Group): Improvement of ≥40% and absolute improvement of ≥20 units (on a scale of 0-100) from baseline in ≥3 of the 4 domains, without deterioration in the potential remaining domain. Deterioration is defined as a change for the worse of ≥20% and net worsening of ≥10 units (on a scale of 0-100). For this analysis, patients were categorized into mutually exclusive ASAS response groups: Nonresponder (<ASAS20); ≥ASAS20 to <ASAS40; ≥ASAS40.

ASAS 5/6, characterized by: Improvement of ≥20% in 5 of 6 domains; physical function; total back pain; patient global assessment of disease activity; inflammation; spinal mobility; Acute Phase Reactants (C-reactive protein).

BASDAI: was composed of six questions on fatigue, spinal pain, peripheral arthritis, enthesitis, and duration and severity of morning stiffness during the past week. Total score range from 0-10, with lower scores representing a better disease state. BASDAI 20, 50, 70 is defined as 20%, 50%, 70% improvement in BASDAI score, respectively. For this analysis, patients were categorized into mutually exclusive BASDAI response groups: Nonresponder (<BASDAI 20); ≥BASDAI 20 to <BASDAI 50; BASDAI 50 to <BASDAI 70; ≥BASDAI 70.

ANCOVA analyses controlled for age, sex, and the relevant baseline HRQL scores. Overall p-values tested for differences in HEOR response among the 4 ASAS response subgroups or among the 4 BASDAI response subgroups.

SF-36 is a widely applied instrument for measuring health status and consists of 8 domains: physical function, bodily pain, role limitations—physical, general health, vitality, social function, role limitations—emotional, and mental health. Domain scores range from 0-100, with higher scores reflecting better health status. SF-36 also contains 2 summary scores: the physical component summary (PCS) and the mental component summary (MCS); an MID (minimum important difference) of a 3 point change in summary scores is considered clinically meaningful.

The ASQoL is a disease-specific instrument measuring HRQL in patients with AS. Patients are asked to answer 18 yes/no items concerning the impact of AS "at this moment". Scores range from 0-18, with lower scores representing better AS-specific quality of life. The instrument has good reliability and construct validity across several different AS populations, 1-4 and the MID has been suggested to be a change of 2 points.

A total of 315 subjects (ADA, n=208; PBO, n=107) were enrolled. At Week 12, ASAS and BASDAI 20/50/70 responses for ADA patients were significantly better than PBO. Mean change from BL at Week 12 HRQL scores are presented in Table 5.

TABLE 5

| Clinical Improvement Status | SF-36 PCS.[†] | SF-36 MCS.[†] | ASQoL.[†] |
|---|---|---|---|
| By ASAS Criteria | | | |
| Nonresponder (<ASAS20) | 0.7 (6.4) | 1.0 (10.9) | −0.4 (2.7) |
| ≥ASAS20 to <ASAS50 | 6.9* (8.0) | 2.4 (10.1) | −3.1* (3.1) |
| ≥ASAS50 to <ASAS70 | 11.7* (7.5) | 0.3 (10.9) | −4.0* (3.5) |
| ≥ASAS70[4] | 14.0* (6.1) | 9.6* (9.5) | −7.5* (3.7) |
| Overall p-value[#] | <0.001 | <0.001 | <0.001 |
| By BASDAI Criteria | | | |
| Nonresponder (<BASDAI20) | 0.3 (6.3) | −0.5 (10.4) | −0.1 (2.6) |
| ≥BASDAI20 to <BASDAI50 | 5.0* (8.1) | 2.3 (10.3) | −1.9 (2.5) |
| ≥BASDAI50 to <BASDAI70 | 7.3* (7.3) | 4.3* (11.9) | −4.0* (4.0) |
| ≥BASDAI70 | 13.6* (7.0) | 7.6* (10.1) | −6.8* (3.7) |
| Overall p-value[#] | <0.001 | <0.001 | <0.001 |

[†]Mean (SD);
*Clinical meaningful improvement;
[#]P value for overall test of differences among the ASAS or BASDAI groups from the ANCOVA analyses.

At Week 12, patients treated with adalimumab 40 mg eow demonstrated statistically significant results for ASAS20, ASAS40, ASAS 5/6, and BASDAI 50 responses when compared with placebo (Tables 6 and 7). Patients responding to more stringent ASAS20/50/70 or BASDAI 20/50/70 criteria showed a better response in HRQL measures (Table 6).

TABLE 6

ASAS20 and ASAS40[‡] Response at Week 12

| | Placebo | Adalimumab |
|---|---|---|
| ASAS20 | 20.6 | 58.2* |
| ASAS40[‡] | 14 | 40.9[†] |

Numbers represent percentage of patients.
*Statistically significant at p = 0.001 level. p-value by Pearson's Chi-Square test.
[†]p < 0.001; Last Observation Carried Forward (LOCF); P value for difference between therapies from ANCOVA. Nonresponder imputation: Patients who received early escape therapy or discontinued are counted as nonresponders at all subsequent visits. Patients with missing values are counted as nonresponders for that specific visit.
[‡]Modified ASAS40 criteria.

TABLE 7

ASAS 5/6 and BASDAI 50 Response at Week 12

| | Placebo | Adalimumab |
|---|---|---|
| ASAS 5/6 | 13.1 | 48.6* |
| BASDAI 50 | 15.9 | 45.2[†] |

[†]p < 0.001; Last Observation Carried Forward (LOCF); P value for difference between therapies from ANCOVA. Nonresponder imputation: Patients who received early escape therapy or discontinued are counted as nonresponders at all subsequent visits. Patients with missing values are counted as nonresponders for that specific visit.

Figure 4:
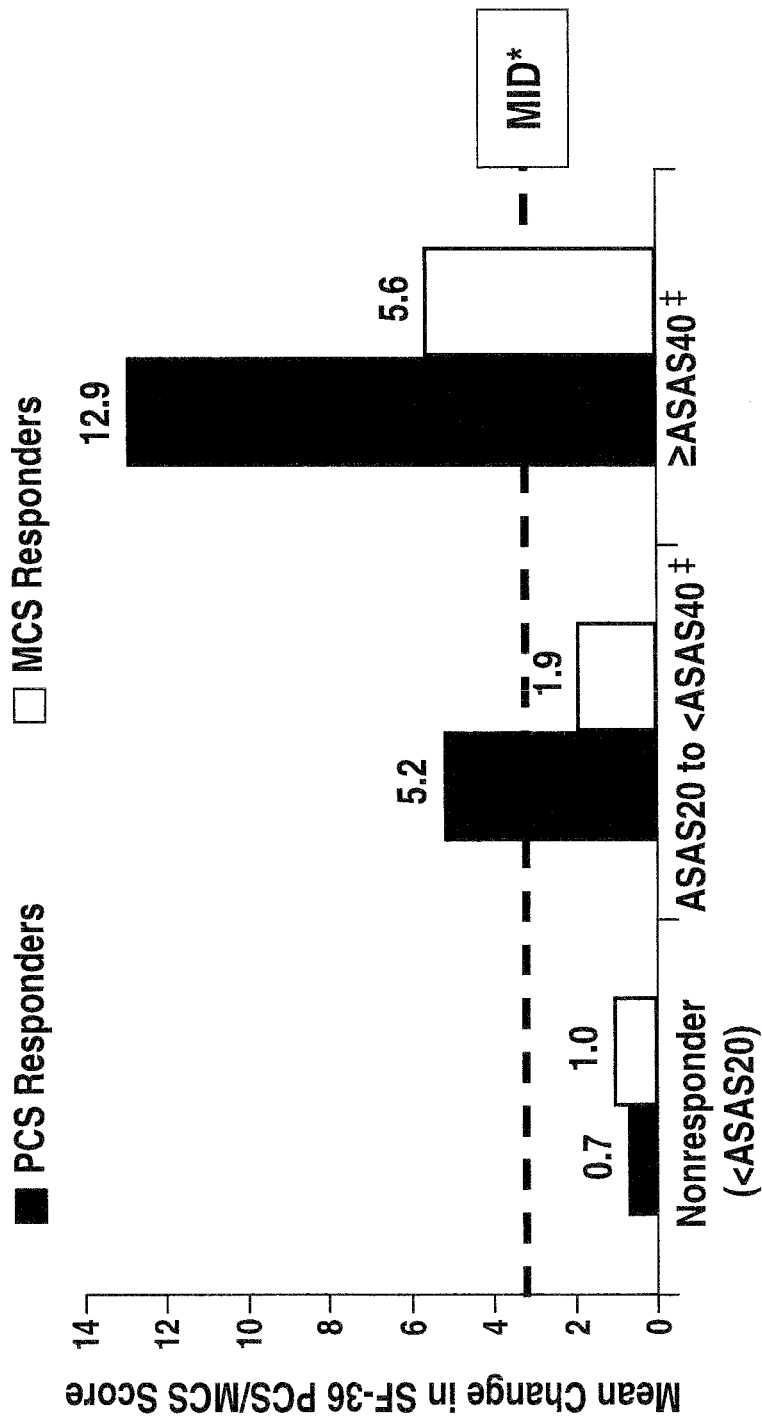
FIG. 4 shows the mean change in SF-36 PCS and MCS scores as stratified by ASAS response at week 12 for patients in the study of example 3.
Figure 5:
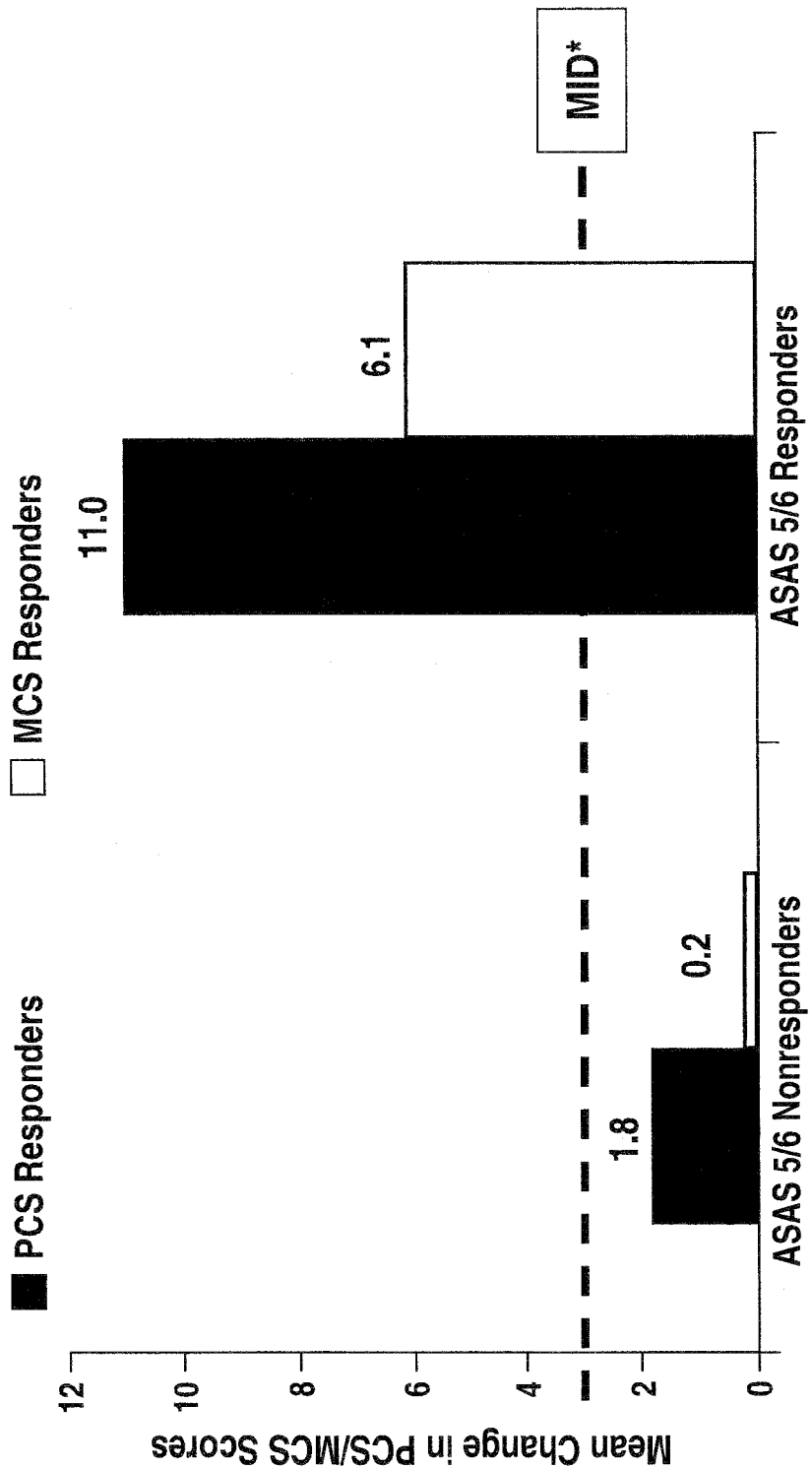
FIG. 5 shows a mean change in SF-36 PCS and MCS Scores as stratified by ASAS response at week 12 for patients in the study of example 3.
Figure 6:
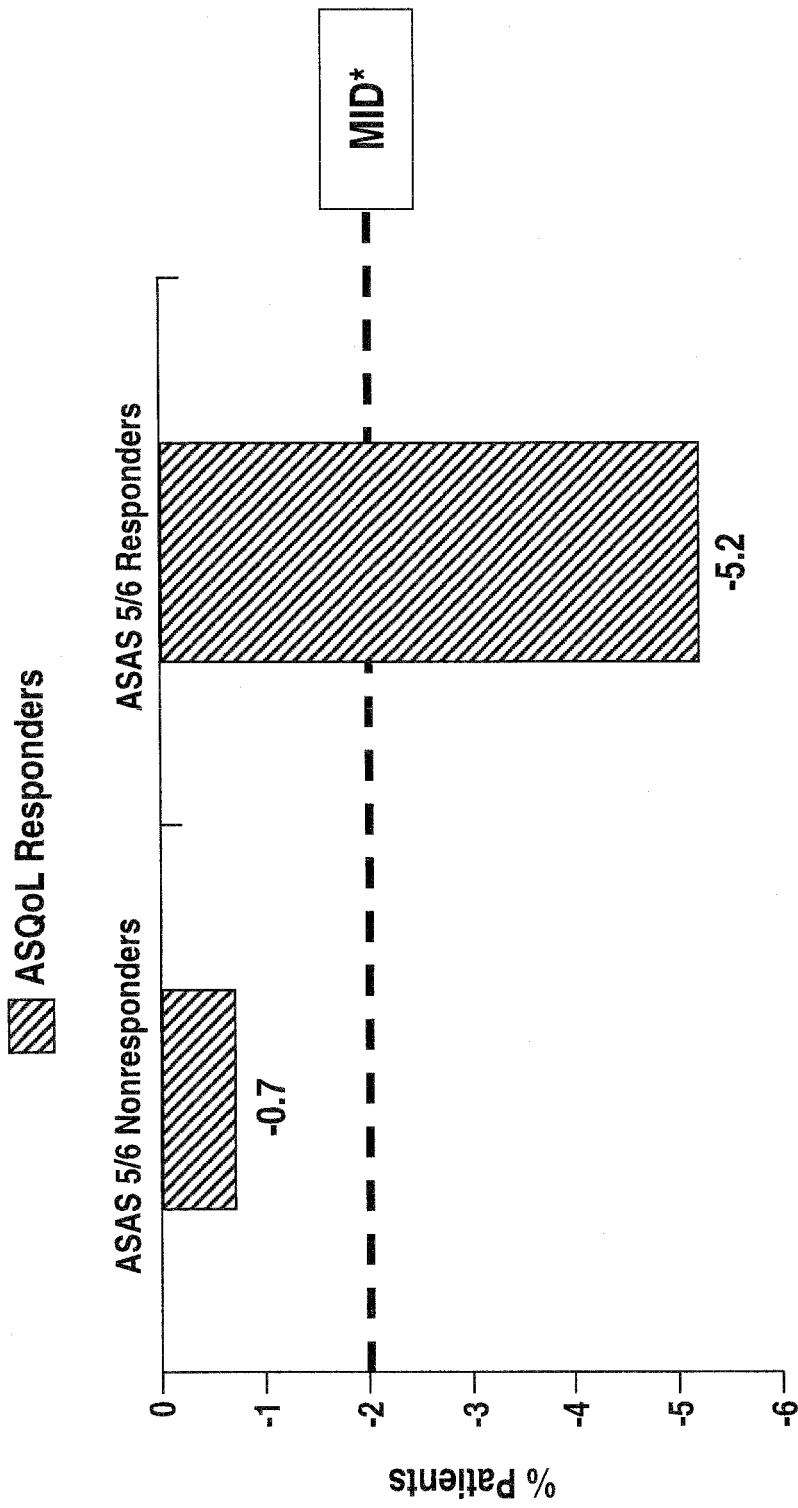
FIG. 6 shows a mean change in ASQoL Scores as stratified by ASAS 5/6 criteria at week 12 for patients in the study of example 3.

At Week 12, patients who reported greater improvements in ASAS and BASDAI response also reported greater improvements in SF-36 PCS and MCS scores (FIGS. 4, and 5). A significant improvement in ASQoL scores was associated with improvements in ASAS responses at Week 12 (see Table 8 and FIG. 6).

TABLE 8

Mean Change in ASQoL Scores as Stratified by ASAS Response at Week 12

| | Mean Change in ASQoL Scores |
|---|---|
| Nonresponders (<ASAS20) | −0.4 |
| ASAS20 to <ASAS40‡ | −2.3 |
| ≥ASAS40‡ | −6.0* | p < 0.0001; p-value for overall test of differences between ASAS responder groups from an ANCOVA model that includes ASAS responder group, baseline score, age, and gender.
*Minimum Important Difference = −2, see Haywood K L, et al. J. Rheumatol. 2003; 30: 764-773; Haywood K L, et al. J. Rheumatol. 2002; 41: 1295-1302.
‡Modified ASAS40 criteria (see above).

In conclusion, this analysis showed a strong correlation between disease activity and HRQL in AS. The significant reduction of signs and symptoms in AS patients treated with adalimumab leads to significant improvement of not only the physical functioning but also overall well being.

Example 4

Adalimumab Reduces Spinal and Sacroiliac Joint Inflammation in Patients with Ankylosing Spondylitis (AS)

52 Week Magnetic Resonance Imaging (MRI) Results

Significant spinal and sacroiliac (SI) joint inflammation is characteristic of AS patients. The purpose of this study was to evaluate the efficacy of adalimumab (ADA) vs. placebo (PBO) in reducing spinal and SI joint inflammation in MRIs among patients with active AS.

The following describes a Phase III study with a 24-week double-blind period during which patients were randomized to receive either ADA 40 mg every other wk (eow) or PBO.

Figure 7:
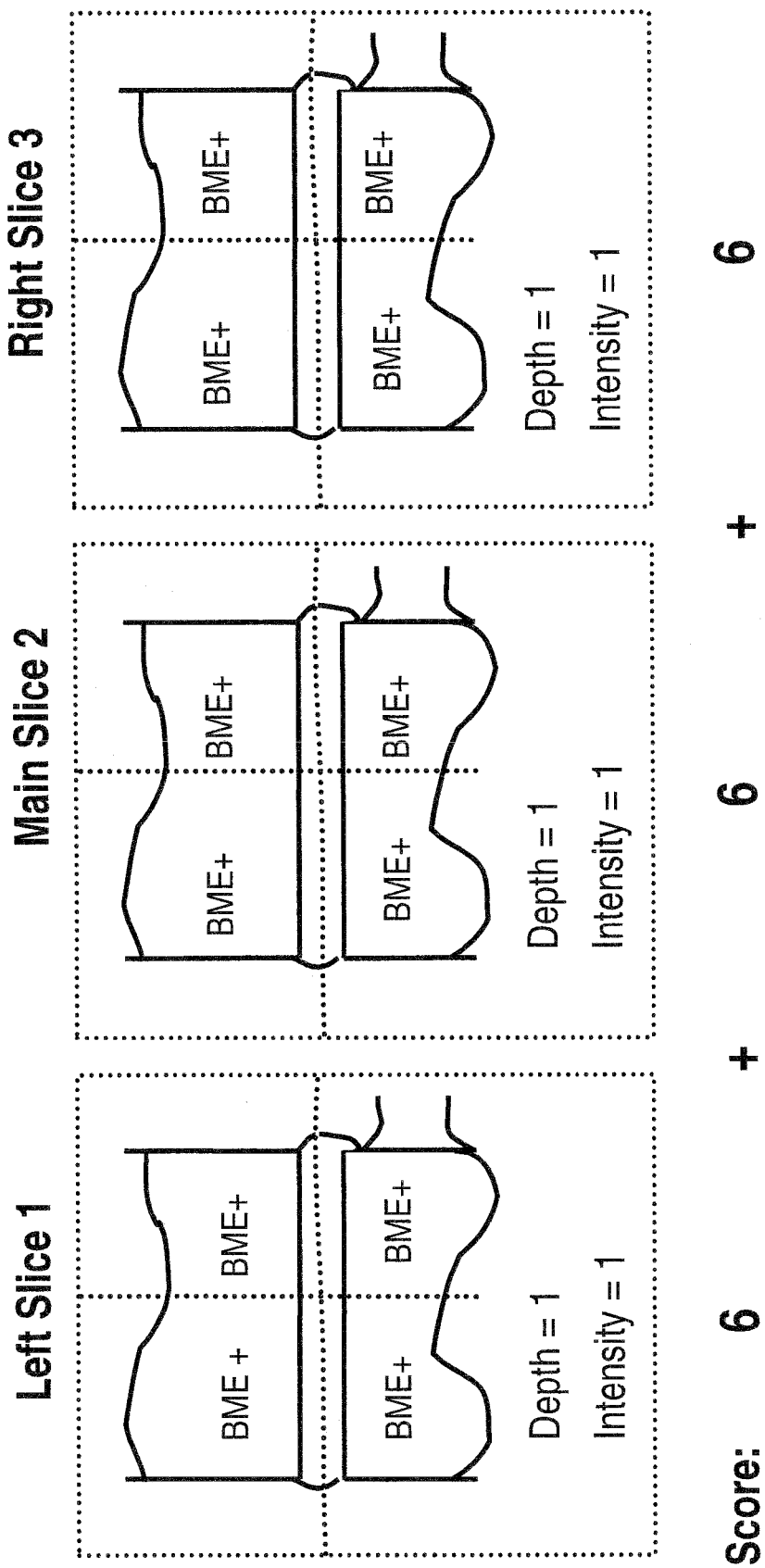
FIG. 7 graphically depicts SPARCC MRI Spinal Index: Maximum Score per Disco-vertebral Unit (DVU).
Figure 8:
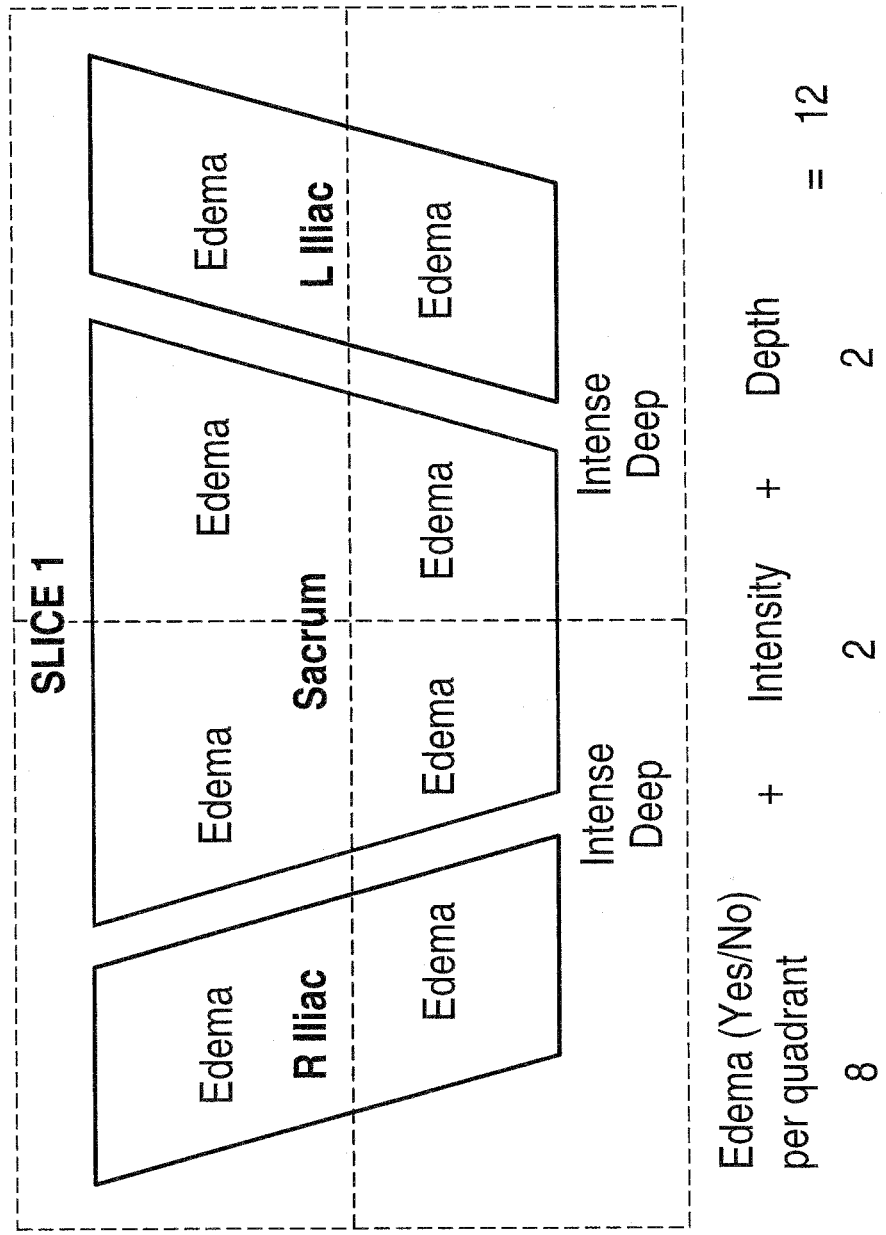
FIG. 8 graphically depicts SPARCC MRI SIJ Index Maximum Score per Coronal Slice.

This was followed by an 80-week open label period where both ADA and PBO patients were administered ADA 40 mg eow. MRIs of the spine and SI joints were performed at Baseline (BL), Week 12, and Week 52. Inflammation was measured by the Spondylarthritis Research Consortium of Canada (SPARCC) MRI Index (FIGS. 7 and 8).

A total of 82 patients with Active AS patients that had an inadequate response to at least 1 NSAID and may have failed at least 1 DMARD were enrolled. 44 patients received PBO and 38 ADA. ADA and PBO arms had similar baseline characteristics (Table 9).

TABLE 9

Baseline Demographics

|  | Placebo (n = 44) | Adalimumab 40 mg eow (n = 38) | p-value |
|---|---|---|---|
| Age, years* | 40.0 | 41.9 | ns |
| Sex, male, n (%) | 36 (81.8) | 29 (76.3) | ns |
| BASDAI score* | 6.5 | 6.2 | ns |
| BASFI score* | 5.6 | 5.2 | ns |
| CRP (mg/dL)*† | 2.3 | 1.8 | ns |

Tables 10-13 show other patient baseline data including concomitant diseases, DMARDs used, other medications used at baseline.

TABLE 10

Concomitant Disease at Baseline

|  | Placebo (n = 44) n (%) | Adalimumab 40 mg eow (n = 38) n (%) | p-value |
|---|---|---|---|
| Inflammatory bowel disease | 5 (11.4) | 4 (10.5) | ns |
| Crohn's disease | 3 (6.8) | 2 (5.3) | ns |
| Ulcerative colitis | 2 (4.5) | 2 (5.3) | ns |
| Psoriasis | 8 (18.2) | 3 (7.9) | ns |
| Uveitis | 15 (34.1) | 17 (44.7) | ns |
| Reactive arthritis/ Reiters syndrome | 3 (6.8) | 2 (5.3) | ns |
| Dactylitis | 1 (2.3) | 0 | ns |

TABLE 11

DMARDs at or Prior to Baseline

| No. of DMARDs | Placebo (n = 44) n (%) | Adalimumab 40 mg eow (n = 38) n (%) |
|---|---|---|
| 0 | 28 (63.6) | 26 (68.4) |
| 1 | 9 (20.5) | 8 (21.1) |
| 2 | 6 (13.6) | 2 (5.3) |
| 3 | 1 (2.3) | 2 (5.3) |
| ≥4 | 0 (0) | 0 (0) |
| At least 1 DMARD | 16 (36.4) | 12 (31.6) |

TABLE 12

DMARDs at Baseline

|  | Placebo (n = 44) | Adalimumab 40 mg eow (n = 38) | p-value* |
|---|---|---|---|
| Baseline DMARD use, n (%) | 9 (20.5) | 6 (15.8) | ns |
| Methotrexate, n (%) | 4 (9.1) | 4 (10.5) | ns |
| Dose (mg/week)† | 18.75 ± 4.79 | 17.50 ± 6.46 |  |
| Sulfasalazine, n (%) | 5 (11.4) | 3 (7.9) | ns |
| Dose (mg/day)† | 2400 ± 894 | 2400 ± 0 |  |
| Leflunomide, n (%) | 0 | 0 | n/d |

*Fisher's exact test
†Mean ± SD

TABLE 13

Concomitant Medication at Baseline

|  | Placebo (n = 44) | Adalimumab 40 mg eow (n = 38) | p-value* |
|---|---|---|---|
| Oral corticosteroids, n (%) | 4 (9.1) | 3 (7.9) | ns |
| Dose (mg/day)† | 7.0 (2.4) | 6.7 (2.9) |  |
| NSAIDs, n (%) | 40 (90.9) | 34 (89.5) | ns |

Data was achieved using commercially available MRI systems (i.e., GE, Phillips, Siemens) operating at 1.0-1.5 Tesla. Two readers, blinded to: Time point and treatment group read the patients MRIs which were taken at three time points: Baseline, Week 12 (Early escape option at Weeks 12, 16, or 20), and Week 52.

The primary endpoint was ASAS20 at Week 12 while the major secondary endpoints included: ASAS20 at Week 24; ASAS50; ASAS 70; Bath Ankylosing Spondylitis Disease Activity Index (BASDAI) 20, 50, 70 response; and C-reactive protein (CRP). ASAS20 components included: patient's global assessment of disease activity; total back pain; Bath Ankylosing Spondylitis Functional Index (BASFI); and inflammation.

Table 14 displays the effects of ADA and PBO on spinal and SI joint inflammation.

TABLE 14

| Inflammation Measure/Arm | N | BL | Wk 12 Mean Value | BL-Wk 12 % Change | p-value* |
|---|---|---|---|---|---|
| Spinal SPARCC/PBO | 41 | 19.9 | 18.6 | −9% | — |
| Spinal SPARCC/ADA | 37 | 16.0 | 6.7 | −54% | <0.0001 |
| SI Joint SPARCC/PBO | 29 | 7.5 | 6.4 | −13% | — |
| SI Joint SPARCC/ADA | 24 | 5.7 | 2.1 | −53% | <0.0001 |

*Comparison of percent change from BL of ADA vs. PBO.

TABLE 15

Patient Disposition at Week 52

|  | Placebo (N = 44) | Adalimumab 40 mg eow (N = 38) |
|---|---|---|
| Patients Randomized | 44 | 38 |
| Patients Treated | 44 | 38 |
| Patients Completing Week 24 | 42 (95.5)* | 38 (100.0)* |
| Patients Completing Week 52 | — | 72 (87.8)*† |

*n (%)
†All patients on adalimumab after Week 24; total N = 82

Figure 9:
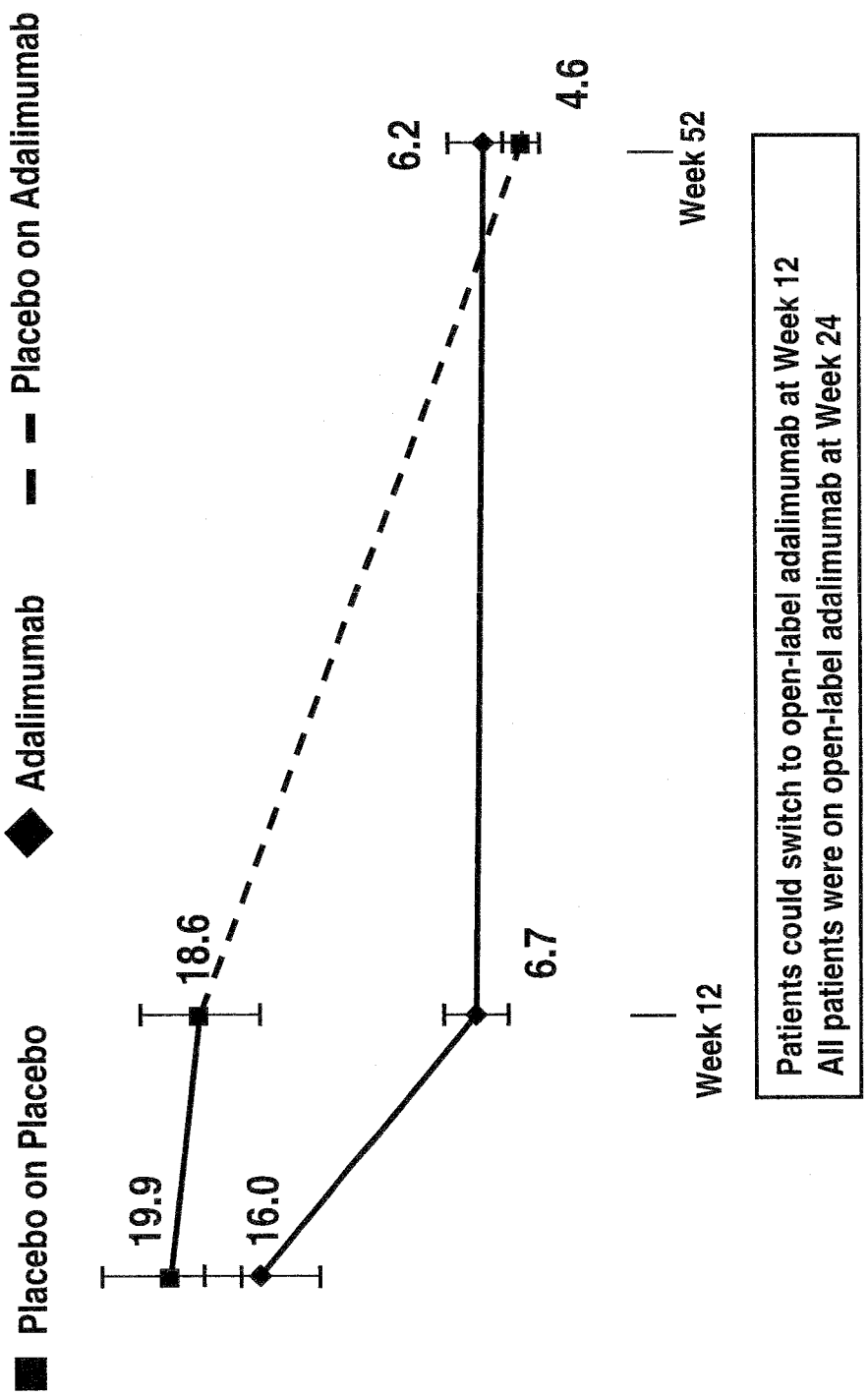
FIG. 9 graphically depicts SPARCC Scores through week 52 for the Spine.
Figure 10:
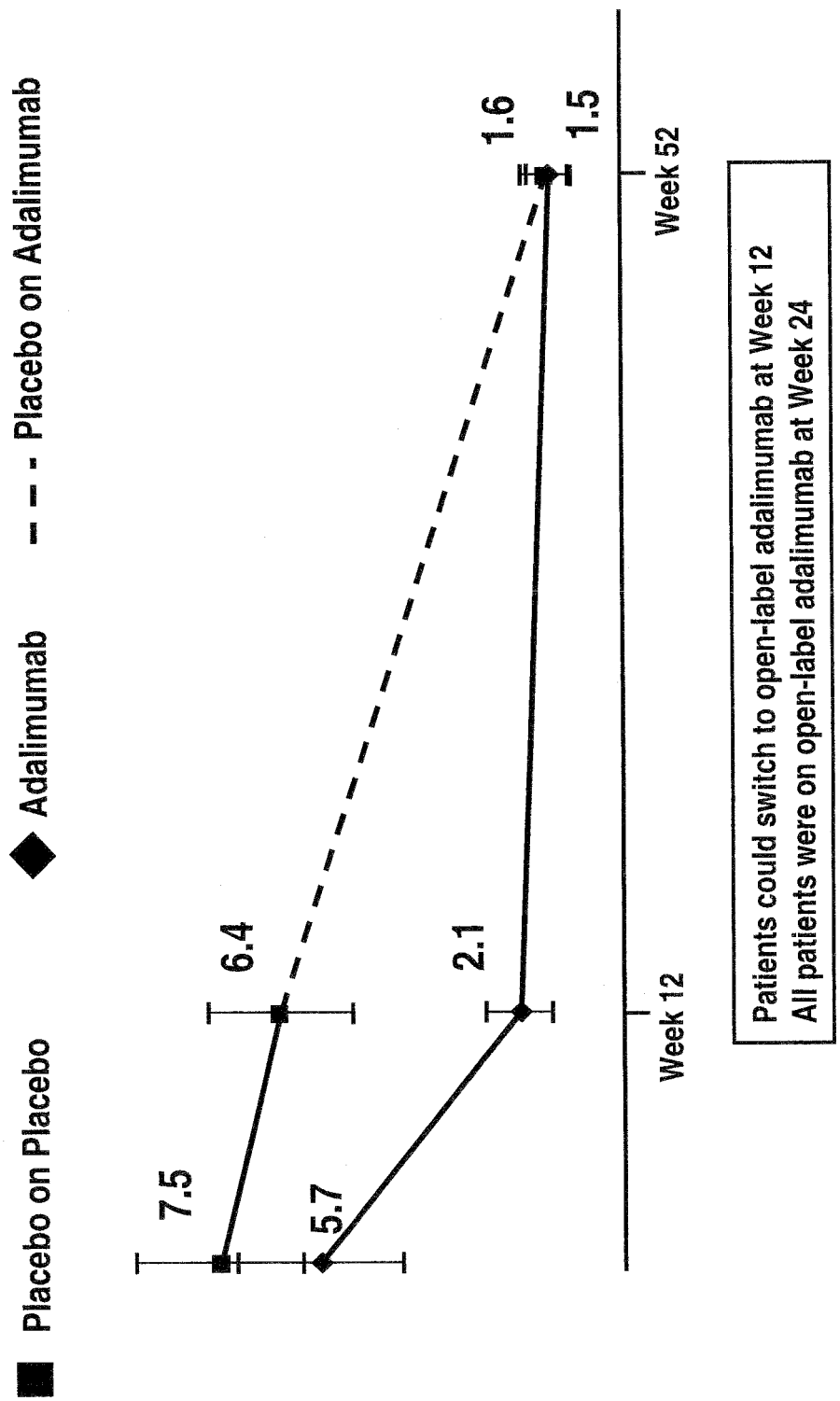
FIG. 10 graphically depicts SPARCC Scores through week 52 for the SI Joint.
Figure 11:
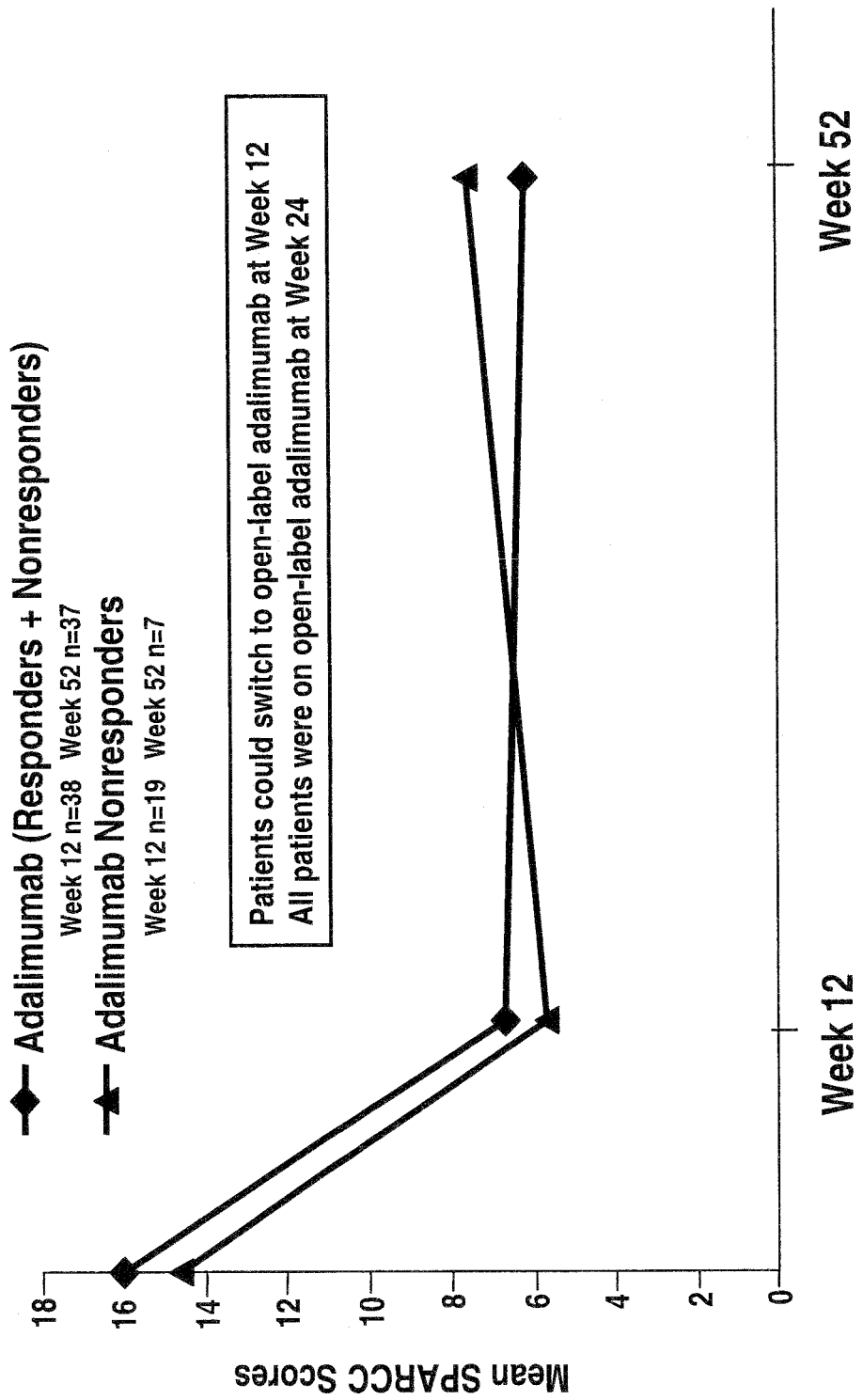
FIG. 11 graphically depicts SPARCC Scores through week 52—spine ASAS20 nonresponders (Observed).
Figure 12:
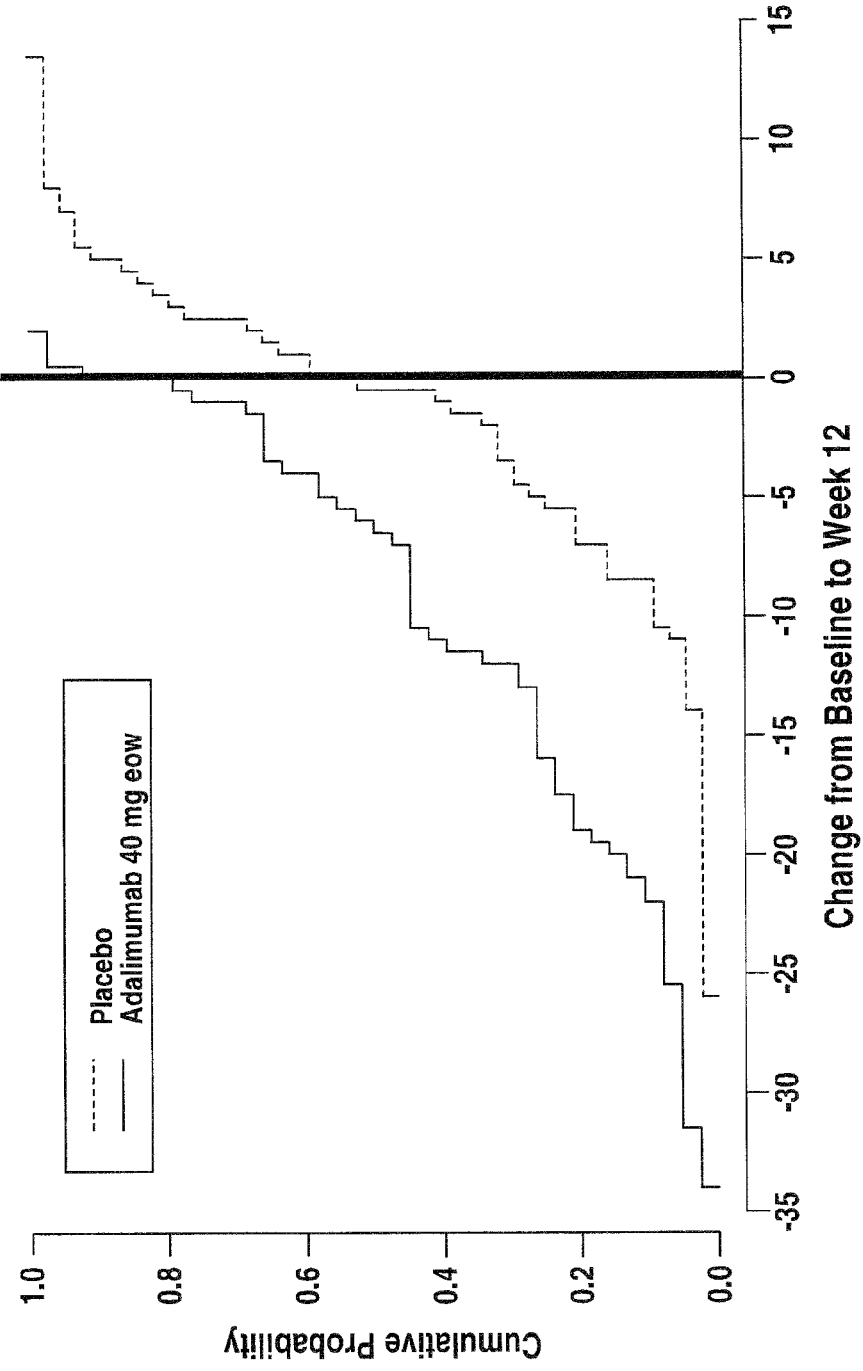
FIG. 12 graphically depicts the cumulative probability—spine baseline to week 12.
Figure 13:
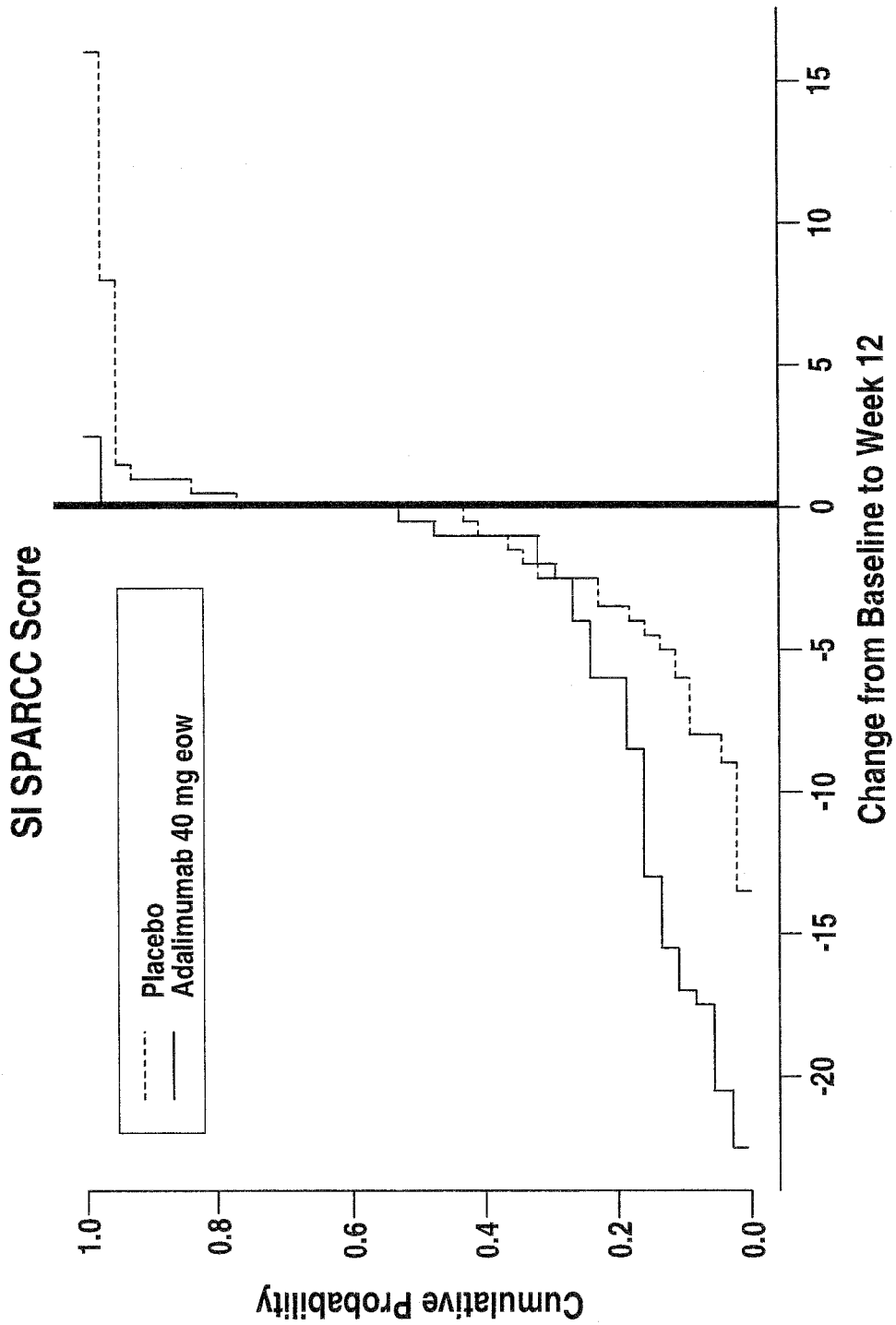
FIG. 13 graphically depicts cumulative probability—SI joint baseline to week 12.

Patient Disposition data at week 52 is shown above in Table 15. In those patients with available data, the reduction in both spinal and SI joint inflammation was sustained through Week 52. In the ADA group, the mean SPARCC scores at Week 52 were 6.2 for the spine (−50% change from BL, n=37) and 1.5 for the SI joints (−52% change from BL, n=23). After Week 24, PBO patients were switched to open label ADA and had improved SPARCC scores in both spine and joint, that were comparable to the ADA patients by Week 52 (FIGS. 9-11). The mean percent change in SPARRC scores in the spine were as follows: 53.6% at week 12 for those patients receiving Adalimumab; 57.2% at week 52 for those patients receiving Adalimumab after placebo; and 50.4% at week 52 for those patients receiving Adalimumab. The mean percent change in SPARRC scores in the SI Joint were as follows: 52.9% week 12 for those patients receiving Adalimumab; 58.6% at week 52 for those patients receiving Adalimumab after placebo; and 51.6% at week 52 for those patients receiving Adalimumab.

Figure 14:
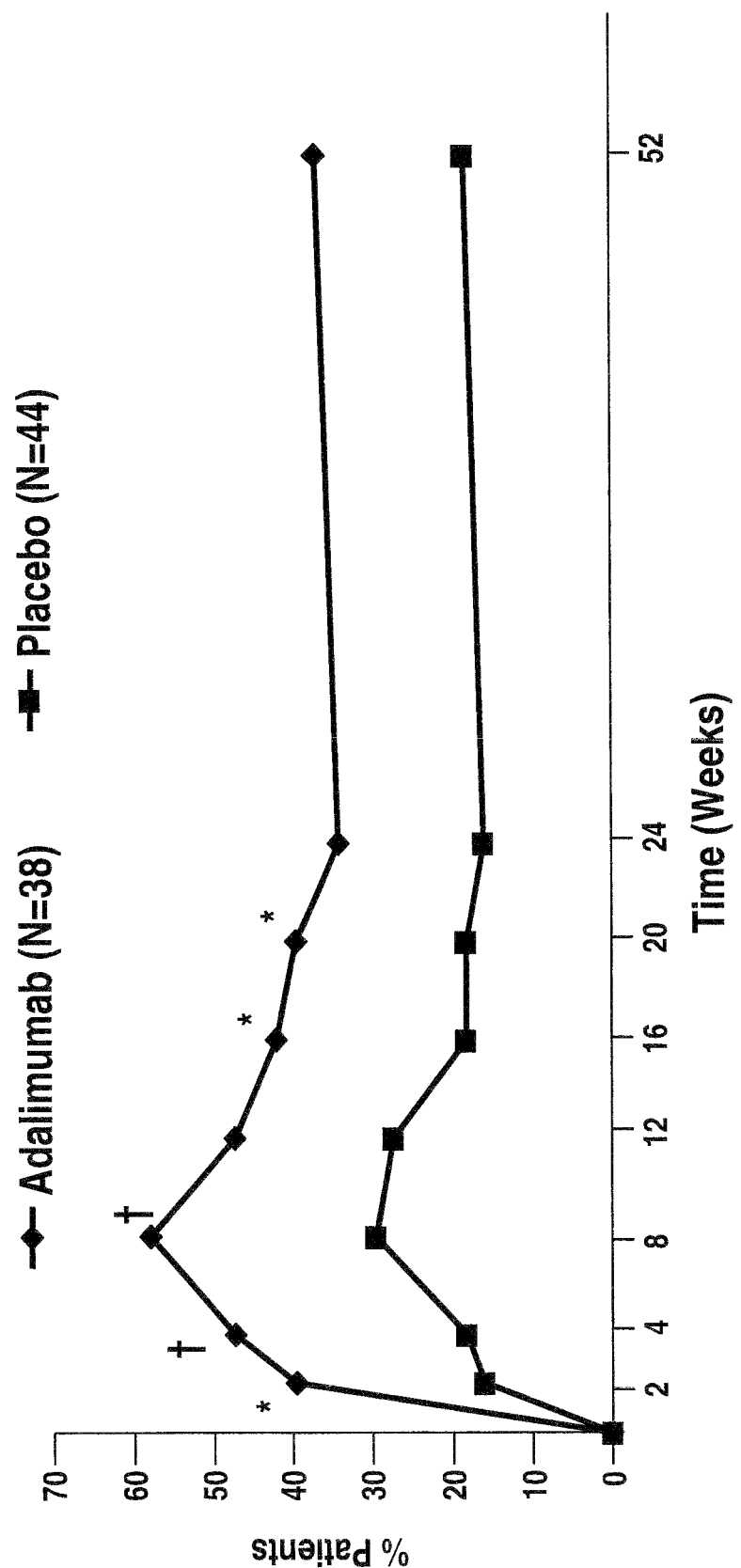
FIG. 14 graphically depicts time course of ASAS20 Response, nonresponder imputation through week 52.
Figure 15:
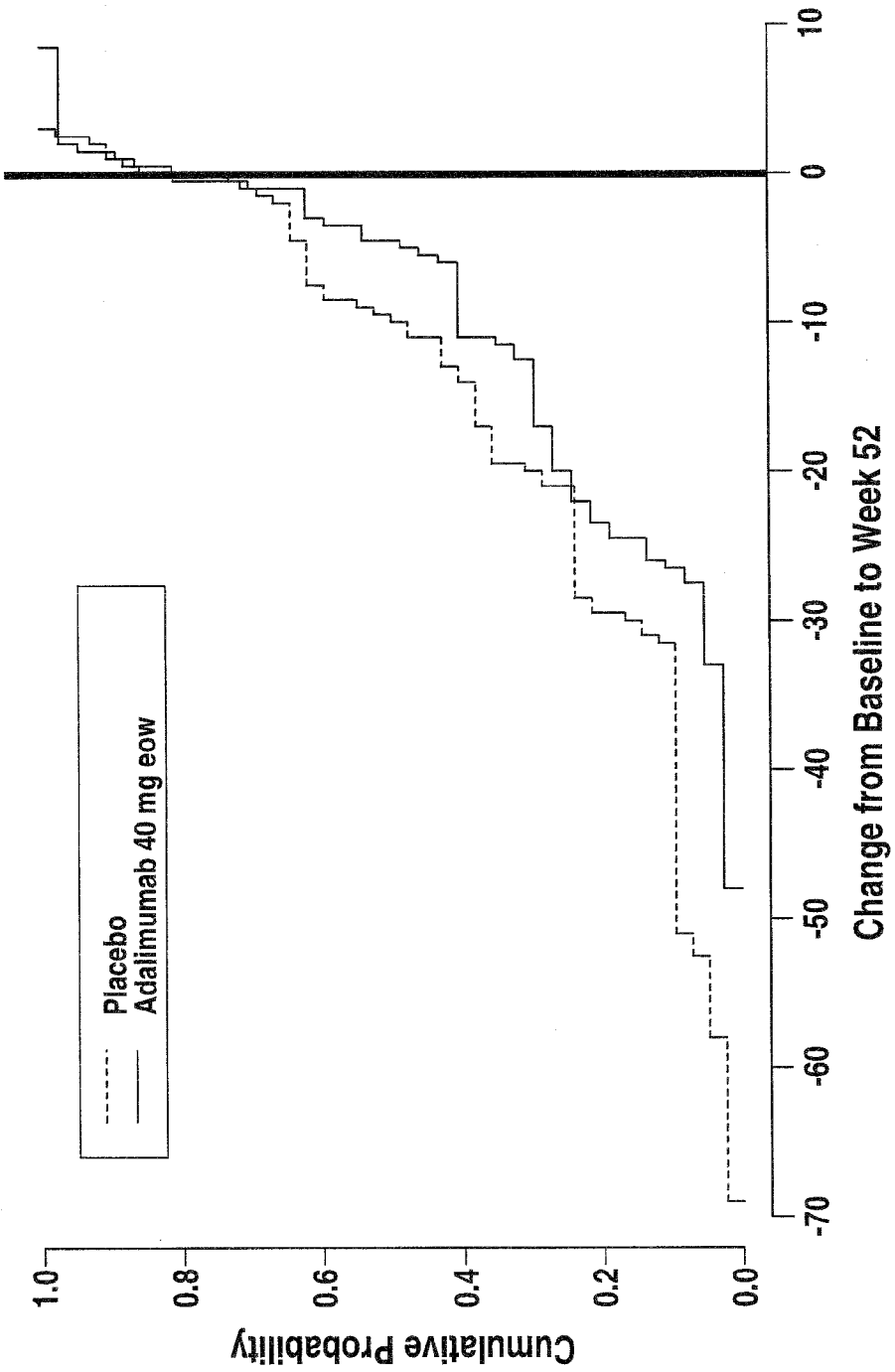
FIG. 15 graphically depicts the cumulative probability—Spine Baseline to Week 52.
Figure 16:
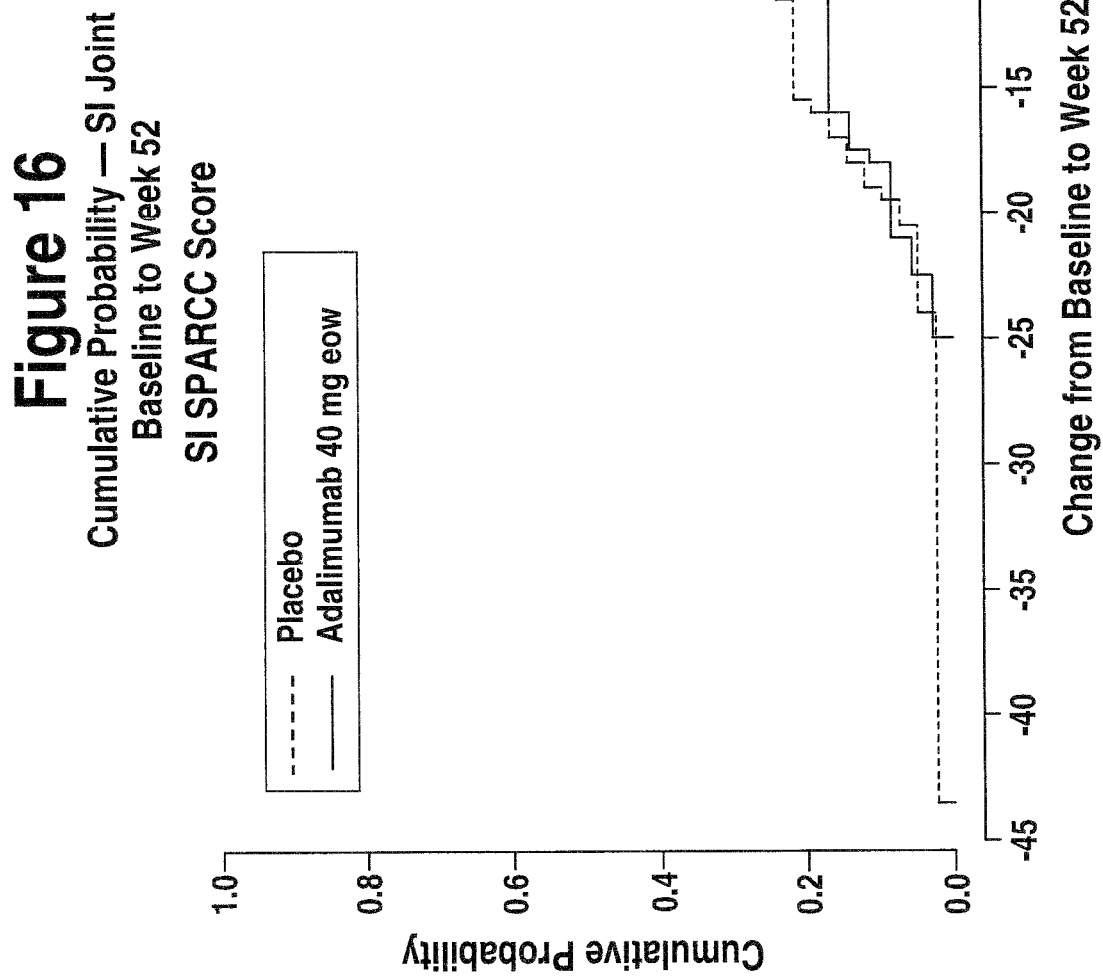
FIG. 16 graphically depicts the cumulative probability—SI Joint Baseline to Week 52.
Figure 17:
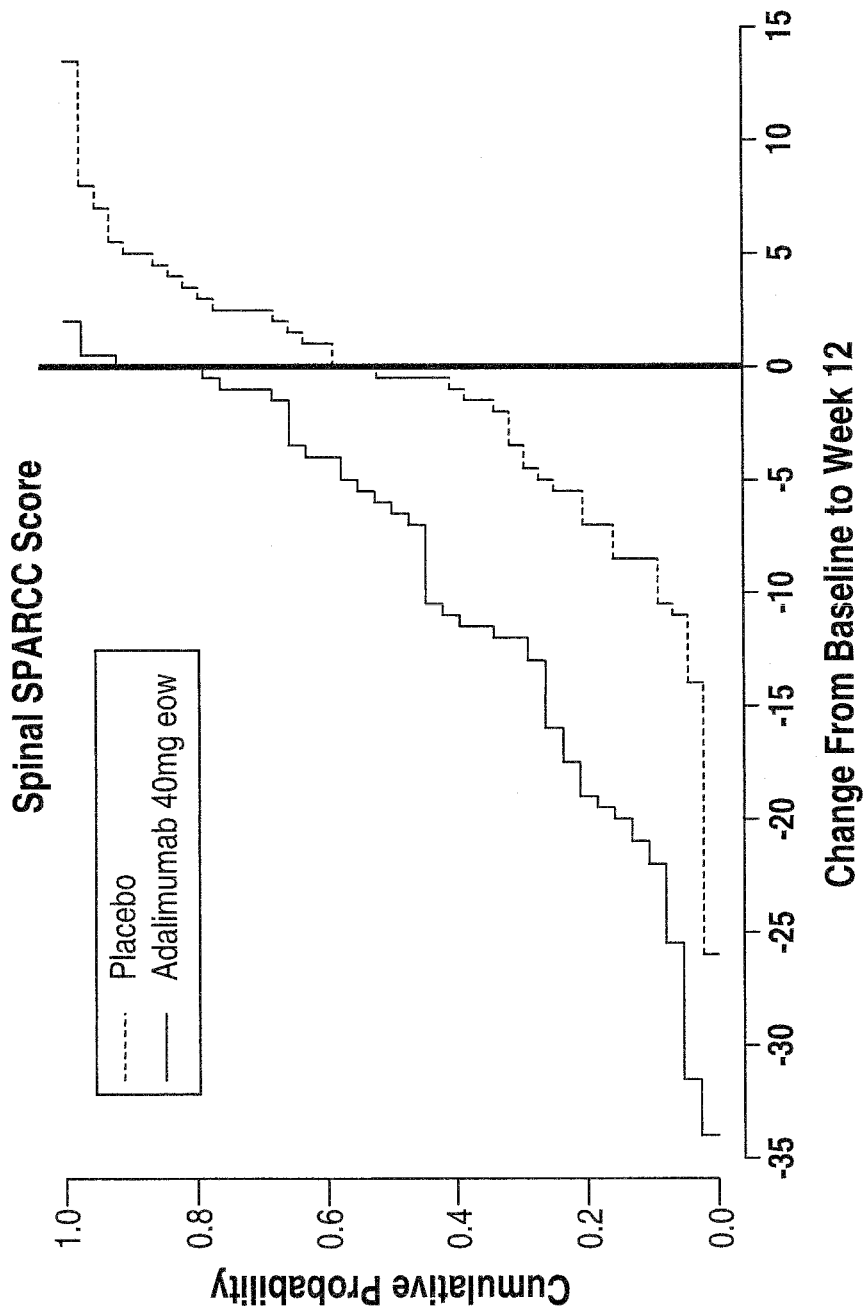
FIGS. 17 and 18 graphically depict the cumulative probability—Spine Baseline and SI Joint Baseline to Week 12.
Figure 18:
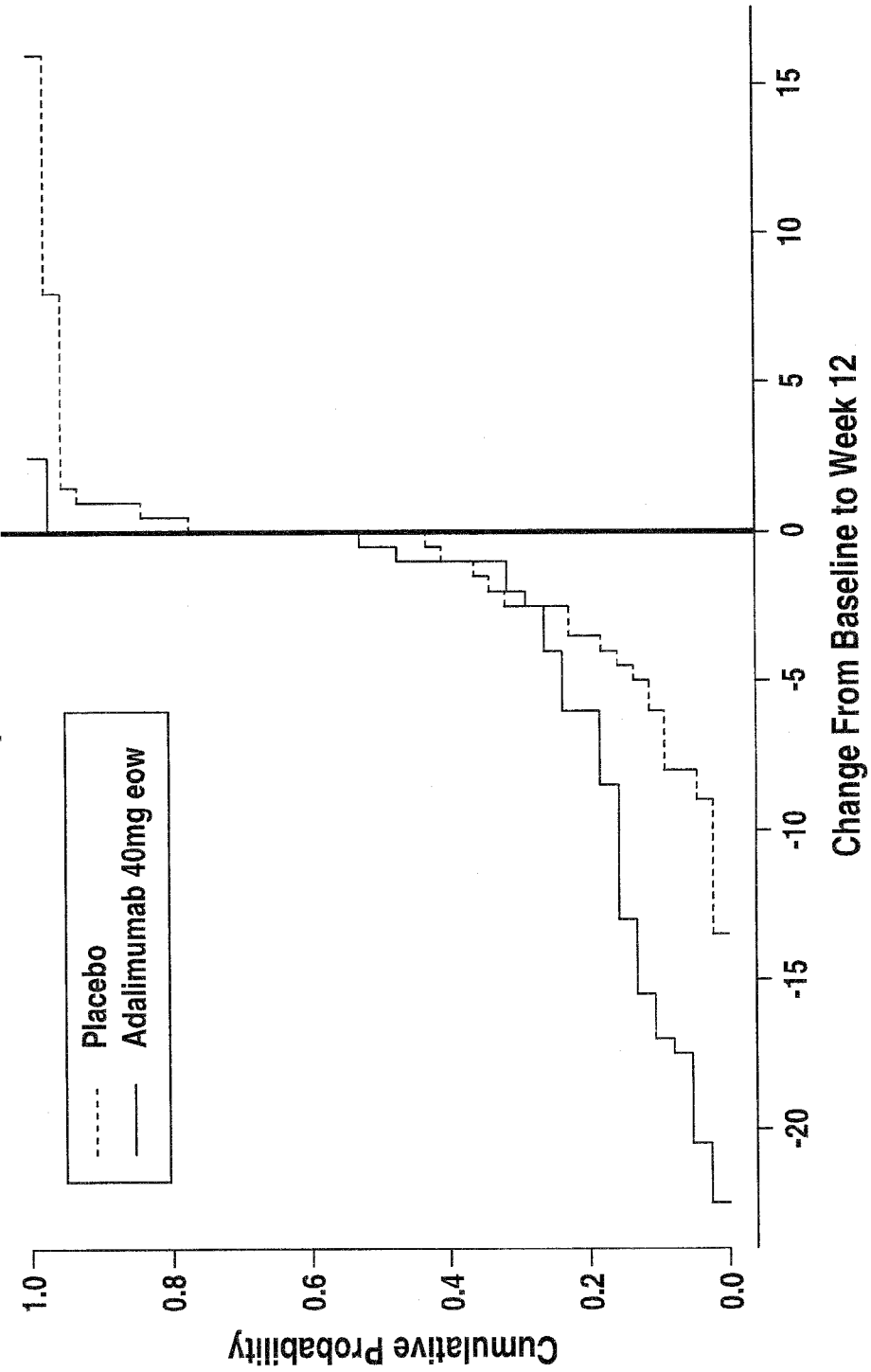

Improvement in C-reactive protein (CRP) levels were also significantly associated with changes in spinal SPARCC score (p=0.018) within the ADA group (as shown in Table 16 below. Adalimumab patients also had higher ASAS 20 responses compared to placebo at Weeks 12 and 24 (FIG. 14). Adalimumab patients had statistically significantly better BASDAI 50 responses compared to placebo at Week 12 (Table 16). Adalimumab patients had statistically significantly better ASAS 50 and ASAS 70 responses at Weeks 12 and 24. Placebo patients who went onto open-label treatment had an excellent ASAS 20 response.

TABLE 16

Correlations Between Clinical Efficacy and Various Parameters

| Change from Baseline in Efficacy Variable | Pearson Correlation Coefficient (r) Change From Baseline to Week 12 in SPARCC Score--Spine | |
|---|---|---|
| | Placebo | Adalimumab |
| CRP | 0.213 | 0.479* |
| BASDAI | 0.154 | 0.213 | p* = 0.018 for adalimumab vs. placebo

FIGS. 12-18 and Table 28 provide other examples of ADA's efficacy in treating AS patients. In addition Tables 17-22 showadalimumab's efficacy determined by SPARCC Scores.

TABLE 17

SPARCC Scores

| Patient | Region | Baseline | Week 12 | Change |
|---|---|---|---|---|
| 131077 | C-Spine | 31.0 | 22.5 | −8.5 |
| 131077 | SI Joints | 26.0 | 12.5 | −13.5 |
| 21030 | C-Spine | 34.5 | 3.0 | −31.5 |
| 21030 | SI Joints | 18.5 | 1.5 | −17.0 |

TABLE 18

Nonzero SPARCC Scores

| | Placebo N = 44 N (%) | Adalimumab N = 38 N (%) |
|---|---|---|
| Patients with Spinal SPARCC Scores at Baseline | 44 (100.0) | 38 (100.0) |
| at Week 12 | 44 (100.0) | 38 (100.0) |
| at Week 52 | 42 (95.5) | 38 (100.0) |
| Nonzero SPARCC Scores at Baseline | 41 (93.2) | 37 (97.4) |
| Patients with SI Joints SPARCC Scores at Baseline | 44 (100.0) | 38 (100.0) |
| at Week 12 | 44 (100.0) | 38 (100.0) |
| at Week 52 | 42 (95.5) | 38 (100.0) |
| Nonzero SPARCC Scores at Baseline | 41 (93.2) | 37 (97.4) |

TABLE 19

SPARCC - ICC scores

| Spine Only | Inter-reader reliability - ANOVA | |
|---|---|---|
| Time point | N | ICC |
| Baseline | 82 | 0.932 |
| Week 12 | 82 | 0.910 |
| Week 52 | 80 | 0.798 |

TABLE 20

SPARCC - ICC scores

| SI Joint | Inter-reader reliability - ANOVA | |
|---|---|---|
| Time point | N | ICC |
| Baseline | 82 | 0.874 |
| Week 12 | 82 | 0.840 |
| Week 52 | 79 | 0.412 |

TABLE 21

SPARCC - ICC scores

Intra-reader reliability - ANOVA

| | Reader 1 | | Reader 2 | |
|---|---|---|---|---|
| Time point | N | ICC | N | ICC |
| Baseline | 10 | 0.976 | 10 | 0.968 |
| Week 12 | 10 | 0.948 | 10 | 0.981 |
| Week 52 | 10 | 0.882 | 10 | 0.981 |

TABLE 22

SPARCC - ICC scores

Intra-reader reliability - ANOVA

| | Reader 1 | | Reader 2 | |
|---|---|---|---|---|
| Time point | N | ICC | N | ICC |
| Baseline | 10 | 0.931 | 10 | 0.991 |
| Week 12 | 10 | 0.971 | 10 | 0.936 |
| Week 52 | 10 | 0.969 | 10 | 0.960 |

In addition to being efficacious, adalimumab was also shown to be well tolerated in patients with AS. The safety profile with adalimumab is consistent with what has been observed with adalimumab in RA and PsA trials. Tables 23-26 all show data relating to reported adverse events.

TABLE 23

Serious Adverse Events (SAE) Through 31 Aug. 2005

| SAE | Onset Day | Outcome |
| --- | --- | --- |
| Diverticular perforation | 251 | Resolved |
| Peritonitis | 194 | Resolved |
| Appendicitis | 193 | Resolved |
| Gastroenteritis | 35 | Resolved |
| Foot fracture | 362 | Resolved |
| Benign mesothelioma | 365 | Resolved |
| Myolipoma | 315 | Resolved |
| Bipolar disorder | 328 | Resolved |
| Psychotic disorder | 343 | Resolved |
| Abortion induced | 456 | Resolved |
| Rotator cuff syndrome | 486 | Ongoing |

TABLE 24

Treatment-Emergent Adverse Events (AEs) Through Week 24

| Patients with: | Placebo (n = 44) n (%) | Adalimumab 40 mg eow (n = 38) n (%) | P Value |
| --- | --- | --- | --- |
| Any AE | 30 (68.2) | 33 (86.8) | ns |
| Serious AE | 0 (0.0) | 1 (2.6) | ns |
| Severe AE | 3 (6.8) | 4 (10.5) | ns |
| AE leading to discontinuation of study drug | 0 (0.0) | 0 (0.0) | ns |
| AE at least possibly drug-related | 13 (29.5) | 12 (31.6) | ns |
| Infectious AE | 8 (18.2) | 14 (36.8) | ns |

TABLE 25

Treatment-Emergent Adverse Events (AEs) Through Week 24

| Patients With: | Placebo (n = 44) n (%) | Adalimumab 40 mg eow (n = 38) n (%) | P Value |
| --- | --- | --- | --- |
| Serious infectious AE | 0 (0.0) | 1 (2.6) | ns |
| Drug hypersensitivity reaction | 0 (0.0) | 0 (0.0) | ns |
| Malignant neoplasm | 0 (0.0) | 0 (0.0) | ns |
| Death | 0 (0.0) | 0 (0.0) | ns |

TABLE 26

Adverse Events ≥5% Incidence Through Week 24

| MedDRA Preferred Term | Placebo (n = 44) n (%) | Adalimumab 40 mg eow (n = 38) n (%) |
| --- | --- | --- |
| Arthralgia | 5 (11.4) | 4 (10.5) |
| Dizziness | 2 (4.5) | 2 (5.3) |
| Headache | 3 (6.8) | 5 (13.2) |
| Injection site reaction | 4 (9.1) | 3 (7.9) |
| Nasopharyngitis | 5 (11.4) | 7 (18.4) |
| Upper respiratory tract infection | 1 (2.3) | 5 (13.2) |

Table 27 shows data relating to those patients choosing the early escape option.

TABLE 27

Patients Receiving Early-Escape Open-Label Therapy

| Visit | Placebo (n = 44) n (%) | Adalimumab 40 mg eow (n = 38) n (%) | Total (N = 82) n (%) |
| --- | --- | --- | --- |
| Total | 36 (81.8) | 23 (60.5) | 59 (72.0) |
| Week 12 | 28 (63.6) | 20 (52.6) | 48 (58.5) |
| Week 14 | 3 (6.8) | 0 (0.0) | 3 (3.7) |
| Week 16 | 3 (6.8) | 3 (7.9) | 6 (7.3) |
| Week 20 | 2 (4.5) | 0 (0.0) | 2 (2.4) |

In conclusion, adalimumab significantly reduced spinal and SI joint inflammation in AS patients after 12 weeks of treatment; this improvement was maintained through 52 weeks. Furthermore, reduction in CRP was predictive of improvements in spinal SPARCC scores in ADA patients at Week 12. The mean change from baseline for C-reactive protein at weeks 12 and 24 was −1.39, as shown in Table 28. Adalimumab was also well tolerated in patients with AS.

TABLE 28

C-Reactive Protein Changes at Weeks 12 and 24

| | CRP (mg/dL)* | |
| --- | --- | --- |
| | Placebo (n = 44) Baseline mean = 2.29 mg/dL | Adalimumab (n = 38) Baseline mean = 1.77 mg/dL |
| Week 12 | 0.16 | −1.39[†] |
| Week 24 | 0.29 | −1.39[†] |

*Mean change from baseline (LOCF).
[†]Statistically significant at P = 0.001 level.
P value for difference between therapies from ANCOVA.
The normal range for CRP, using ultrasensitive assay, is 0.007-0.494 mg/dL Example 5

Adalimumab Significantly Reduces Both Spinal and Sacroiliac Joint Inflammation in Patients With Ankylosing Spondylitis (AS)

Results of a Multicenter, Randomized, Double-Blind, Placebo-Controlled Magnetic Resonance Imaging Study This Example contains further information regarding the study described in Example 4 above. Significant spinal and sacroiliac (SI) joint inflammation is characteristic of AS patients. This study evaluated the efficacy of adalimumab (ADA) vs. placebo (PBO) in reducing spinal and SI joint inflammation in MRIs among patients with active AS.

This was a Phase III study with a 24-week double-blind period during which patients were randomized to receive either ADA 40 mg every other wk (eow) or PBO. This was followed by an 80-week open label period where both ADA and PBO patients were administered ADA 40 mg eow. MRIs of the spine and SI joints were performed at Baseline (BL), Week 12, and Week 52. Inflammation was measured by the Spondylarthritis Research Consortium of Canada (SPARCC) MRI Index (Maksymowych et al. Arthritis Rheum 2005; 53:502-9; Maksymowych et al. Arthritis Rheum 2005; 53:703-9; Landewe et al. J Rheumatol 2005; 32:2050-5).

A total of 82 patients with Active AS patients that had an inadequate response to at least 1 NSAID and may have failed at least 1 DMARD were enrolled. 44 patients received PBO and 38 ADA. ADA and PBO arms had similar baseline characteristics.

Data was achieved using commercially available MRI systems (i.e., GE, Phillips, Siemens) operating at 1.0-1.5 Tesla. Two readers, blinded to: Time point and treatment group, read the patients MRIs which were taken at three time points: Baseline, Week 12 (Early escape option at Weeks 12, 16, or 20), and Week 52.

Patients were adults (≥18 years of age) with a diagnosis of AS defined by the modified New York criteria (van der Linden et al. Arthritis Rheum 1984; 27:361-8) who were not responsive to or were intolerant of ≥1 nonsteroidal antiinflammatory drug. Patients who had failed 1 or more disease-modifying antirheumatic drugs (e.g., methotrexate, sulfasalazine) were also allowed to enroll. Active AS at baseline was defined by fulfillment of 2 of the following 3 criteria: a Bath Ankylosing Spondylitis Disease Activity Index (BASDAI) score ≥4 (Garrett S, Jenkinson T, Kennedy L G, Whitelock H, Gaisford P, Calin A. A new approach to defining disease status in ankylosing spondylitis: the Bath Ankylosing Spondylitis Disease Activity Index. J Rheumatol 1994; 21:2286-91); total back pain visual analog scale (VAS) score ≥40; and morning stiffness ≥1 hour in duration. Patients could continue sulfasalazine (≤3 g/d), methotrexate (≤25 mg/wk), hydroxychloroquine (≤400 mg/d), prednisone and/or prednisone equivalents (≤10 mg/d), and/or nonsteroidal antiinflammatory drugs as long as these doses had remained stable for 4 weeks before baseline.

All patients were evaluated for latent tuberculosis infection at baseline by using a purified protein derivative skin test and chest radiograph; patients with evidence of latent tuberculosis infection were allowed to participate if a documented history of antituberculous treatment was available or if prophylactic antituberculous treatment was initiated before self-administering the first dose of adalimumab.

Patients who had previously received TNF antagonist therapy or 1 or more intraarticular joint injections with corticosteroids within 4 weeks before the baseline visit were excluded from participation. Intraarticular corticosteroids were not allowed during the first 24 weeks of treatment. Patients with radiologic evidence of total spinal ankylosis (bamboo spine) were excluded from participation, as were patients with any contraindication to undergoing an MRI.

All patients in this MRI evaluation participated in a randomized, multicenter, double-blind, placebo-controlled study comparing adalimumab with placebo for the treatment of patients with active AS (Maksymowych et al. Efficacy of adalimumab in active ankylosing spondylitis (AS)—Results of the Canadian AS Study [abstract 505]. Arthritis Rheum 2005; 52(Suppl):S217)). Patients were randomized in a 1:1 ratio to receive either adalimumab 40 mg every other week (eow) or placebo during the initial 24-week double-blind period. Study visits occurred at baseline, Week 2, Week 4, every 4 weeks through Week 24, then every 6 weeks through Week 52. The MRI analysis was limited to the first year of the study. At Week 24, all patients began receiving adalimumab 40 mg eow and this dosage regimen will continue throughout the ongoing open-label period (up to 5 years). Patients who failed to achieve an Assessment in Ankylosing Spondylitis International Working Group 20% response (ASAS20) at Week 12, Week 16, or Week 20 could initiate open-label adalimumab 40 mg eow (early escape option). Patients who had received at least 12 weeks of open-label treatment with adalimumab 40 mg eow and failed to achieve an ASAS20 response were eligible to receive adalimumab 40 mg weekly. Prefilled syringes for subcutaneous injection containing either adalimumab 40 mg or matching placebo were used in the study.

The ASAS response criteria were used to assess the clinical response to adalimumab (Anderson et al. Arthritis Rheum 2001; 44:1876-861). An ASAS20 responder was defined as a patient experiencing improvement of at least 20% and absolute improvement of at least 1 unit from baseline (based on a scale of 0-10) in at least 3 of the following 4 domains: patient's global assessment of disease activity during the past week, represented by the score on a 0-10-cm horizontal VAS; pain during the past week, represented by the total back pain score on a 0-10-cm VAS; function, represented by the Bath AS Functional Index (BASFI) score (0-10-cm VAS) (Calin A, Garrett et al. J Rheumatol 1994; 21:2281-5); inflammation, represented by the mean of the severity and duration of morning stiffness 10-cm VAS scores (mean of questions 5 and 6 of the BASDAI); and no deterioration (defined as a worsening of at least 20% or an absolute increase of at least 1 unit) in the potential remaining domain. The ASAS40 and ASAS 5/6 response criteria were also assessed as previously described (van der Heijde et al Arthritis Rheum 2005; 52:386-94). C-reactive protein (CRP) concentrations at baseline and at every clinic visit were measured using an ultrasensitive CRP assay (normal range, 0.007-0.494 mg/dL). Additional clinical measures of disease activity included nocturnal pain and the Edmonton AS Metrology Index (EDASMI) (Maksymowych et al. Arthritis Rheum 2006; 55:575-82).

An MRI of the spine and SI joints was performed at baseline, Week 12, and Week 52 using appropriate surface coils for commercially available systems operating at 1.0 to 1.5 Tesla. For both the spine and SI joints, STIR sequences were obtained because the intrinsic fat suppression of this T2-weighted sequence allows visualization of bone marrow edema and is more reliable than other sequences when imaging with a large field-of-view. All study sites were instructed to acquire the STIR sequences using the following parameters: repetition time 2720-3170 msec; echo time 38-61 msec; time to inversion 140 msec. Spinal STIR sequences were obtained in sagittal orientation, with 12 to 15 4-mm slices acquired. Imaging of the spine was divided in 2 parts: 1) the entire cervical spine and most of the thoracic spine and 2) the lower portion of the thoracic spine and the entire lumbar spine. STIR sequences of SI joints were obtained in a coronal plane tilted parallel to the long axis of the SI joint, with 12 4-mm slices acquired. T1 spin echo images of the entire spine and SI joints were also obtained for use as anatomical references.

The SPARCC scoring method is based on an abnormal increased signal on the STIR sequence, representing bone marrow edema (defined as an increased signal in bone marrow on a T2-weighted sequence reflecting an increased concentration of "free water" related to a bone lesion). This definition does not distinguish between increased interstitial fluid in the marrow (true edema) and cellular changes associated with increased intracellular water (inflammation). Examples of the scoring method for the spine (Maksymowych et al. Arthritis Rheum 2005; 53:502-9; Maksymowych et al. Validation of the Spondylarthritis Research Consortium of Canada (SPARCC) MRI Spinal Inflammation Index: Is it necessary to score the entire spine? Arthritis Rheum 2006) and the SI joint (Maksymowych et al. Arthritis Rheum 2005; 53:703-9) have been published. The total spinal SPARCC index score ranges from 0 to 108. The total SI joint SPARCC index score ranges from 0 to 72.

All scans were reviewed on work stations with 4 large screens and image-manipulation software custom designed for this trial. This system permitted simultaneous display of all 12 MRI sequences (T1 and STIR for upper and lower spine for all 3 time points) at original (life size) dimensions. Readers had full windowing capability and could choose to score the time points in any order. Scores were recorded electronically on a fifth screen using a computer-assisted masked reading program; the reader was able to see all scores and all scans simultaneously before committing to the final score. Each image was rated by 2 independent readers to allow for calculation of interreader scoring variability. The readers were qualified, trained radiologists who were blinded to patients' identities, treatments, and imaging time points. Ten cases were selected at random to be rescored by each reader to allow for calculation of intrareader scoring variability. These random rereads were completed using the same protocol after initial reads of all MRIs were completed. Bio-Imaging Technologies, Inc., (Newtown, Pa.) was responsible for the collection, digitization, processing, and quality control of MRIs and MRI reading.

The primary efficacy endpoint for the overall study was the ASAS20 response at Week 12. To detect a difference of 31 percentage points in the ASAS20 response at Week 12 with 80% power using Pearson's chi-square test, 39 patients were randomized to each treatment group. Because the SPARCC scores were secondary endpoints of the overall study, there was no a priori power calculation for the MRI subanalysis. An intention-to-treat analysis was used for analyses of the SPARCC scores and all patients with at least 1 baseline MRI were included. The mean of the 2 readers' SPARCC scores was used for all analyses of continuous variables. All statistical tests were 2-sided and comparisons were performed with $\alpha=0.05$.

Baseline and Week 12 measurements were treated as part of the double-blind portion of the study and Week 52 measurements were treated as part of the open-label portion of the study. The changes in SPARCC scores from baseline to Week 12 were compared between the 2 treatment groups using an analysis of covariance (ANCOVA) model with the baseline score as a covariate. Changes from Week 12 to Week 52 were compared between the 2 treatment groups using an ANCOVA model with baseline score and the change from baseline to Week 12 as covariates. There was no imputation of missing SPARCC scores. The SPARCC change scores (from baseline to Week 12 and from baseline to Week 52) were visually evaluated by creating a scatter plot of the change score versus the baseline score for each patient in each treatment group. Additionally, cumulative probability plots were created to show the distribution of change scores for all patients in either adalimumab or placebo treatment arms.

The intrareader ICCs were calculated using an analysis of variance (ANOVA) model with SPARCC scores (spine and SI joint) as the dependent variable, and patient and reader (fixed factor) as independent variables. The level of agreement between the scores assigned by the 2 readers (interreader reliability) was also assessed using an ANOVA to determine the ICCs. An ICC value of >0.6, >0.8, and >0.9 indicates good, very good, and excellent reproducibility, respectively. Bland-Altman plots with 95% confidence intervals, which illustrate the interobserver differences across the range of SPARCC scores, were also used to evaluate reproducibility of the SPARCC scoring method (Bland and Altman. Lancet 1986; 1:307-10).

The association between selected clinical variables and the change in SPARCC scores at Week 12 was evaluated using an ANCOVA model adjusted for baseline SPARCC score, treatment, and change in each of the following measures: BASDAI, selected BASDAI items (i.e., fatigue [item 1], axial disease [item 2], enthesitis [item 4], and inflammation [mean of items 5 and 6]), nocturnal pain, total back pain, patient's global assessment of disease activity, Bath Ankylosing Spondylitis Metrology Index (BASMI) (Jenkinson et al. J Rheumatol 1994; 21:1694-8), EDASMI, and CRP.

Guyatt's effect size for the change in SPARCC scores from baseline to Week 12 was calculated by dividing the mean change in the adalimumab group by the standard deviation of the change in the placebo group; effect sizes were calculated for the change in spinal SPARCC scores and for the change in SI joint SPARCC scores. Guyatt effect sizes of at least 0.2-0.5, 0.5-0.8, and greater than 0.8 were considered small, moderate, and large changes, respectively (Sloan et al. Drug Inf J 2003; 37:23-31).

For about a 1.25 time period, 82 patients with active AS participated in the 52-week, MRI analysis portion of the study. Demographic and baseline characteristics for patients randomized to receive adalimumab (n=38) or placebo (n=44) were similar and consistent with a typical AS population (Table 29). Of note, the mean CRP concentration for both groups of patients was high (Table 29). At baseline and at Week 12, all 44 patients in the placebo group and 38 in the adalimumab group had evaluable MRIs. At Week 52, 42 placebo-treated patients and 38 adalimumab-treated patients had evaluable MRIs; 2 placebo-treated patients had withdrawn from the study.

TABLE 29

Patient Demographic and Baseline Characteristics*

| Characteristic | Placebo (n = 44) | Adalimumab (n = 38) |
|---|---|---|
| Male, % | 81.8 | 76.3 |
| Age, y | 40.0 ± 10.9 | 41.9 ± 11.1 |
| HLA-B27 positive, % | 81.8 | 86.8 |
| Disease duration, y | 12.1 ± 8.7 | 14.5 ± 9.0 |
| BASDAI score (range, 0-10) | 6.5 ± 1.6 | 6.2 ± 1.7 |
| BASFI score (range, 0-10) | 5.6 ± 2.2 | 5.3 ± 2.0 |
| Total back pain VAS (range, 0-100) | 71.7 ± 14.8 | 67.2 ± 16.7 |
| Patient's global assessment (range, 0-100) | 67.8 ± 19.1 | 66.1 ± 18.9 |
| usCRP, mg/dL (0.007-0.494 mg/dL) | 2.3 ± 2.6 | 1.8 ± 1.7 |
| Spinal SPARCC score | 19.9 ± 19.8 | 16.0 ± 15.6 |
| Spinal SPARCC score >0, n (%) | 41 (93.2) | 38 (100) |
| Sacroiliac joint SPARCC score | 7.5 ± 10.0 | 5.7 ± 9.0 |
| Sacroiliac joint SPARCC score >0, n (%) | 29 (65.9) | 24 (63.2) |

*Unless otherwise noted, values are the mean ± SD.
BASDAI = Bath Ankylosing Spondylitis Activity Index; BASFI = Bath Ankylosing Spondylitis Functional Index; usCRP = ultrasensitive C-reactive protein; SD = standard deviation; SPARCC = Spondyloarthritis Research Consortium of Canada; VAS = visual analog scale.

At baseline, mean SPARCC scores were not different between placebo and adalimumab patients for either the spine or the SI joints (Table 29). One adalimumab patient and 3 placebo patients had a spinal SPARCC score of 0 at baseline, and 14 of 38 (36.8%) adalimumab- and 15 of 44 (34.1%) placebo-treated patients had an SI joint SPARCC score of 0 at baseline. No patient had both a spinal and an SI joint SPARCC score of 0 at baseline.

At Week 12, adalimumab-treated patients experienced a statistically significantly (P<0.001) greater reduction in the mean spinal SPARCC score (median change, −6.3; range, −34.0 to 2.0) compared with placebo-treated patients (median change, −0.5; range, −26.0 to 13.5) (For Adalimumab and Placebo on Placebo at week 12, the mean SPARCC score were 6.7 and 18.8 respectively). At Week 24, all patients were receiving adalimumab 40 mg eow, and by Week 52, the spinal SPARCC scores for both adalimumab- and placebo-treated groups were comparable (Mean SPARCC scores of 6.2 for Adalimumab and 4.6 for Placebo on Adalimumab).

The reduction in spinal inflammation in patients randomized to receive adalimumab was sustained from Week 12 to Week 52. A reduction in spinal inflammation between baseline and Week 12 for an individual adalimumab-treated patient was observed upon comparison of magnetic resonance images of the patient's spine.

The change in SI joint SPARCC scores over time followed a similar pattern. At Week 12, the decrease in mean SI joint SPARCC score was statistically significantly greater for adalimumab patients (median change, −0.5; range, −22.5 to 2.5) compared with placebo patients (median change, 0.0; range, −13.5 to 16.0) (P<0.001). In the adalimumab group, the improvement in SI joint SPARCC scores was maintained from Week 12 to Week 52, and scores at Week 52 were comparable for both treatment groups. A reduction in SI joint inflammation for an adalimumab-treated patient was also observed. As expected, the mean changes in both spinal and SI joint SPARCC scores from Week 12 to Week 52 were greater in patients randomized to receive placebo compared with patients randomized to receive adalimumab because patients randomized to adalimumab had already achieved a significant reduction in spinal and SI joint SPARCC scores by Week 12, whereas placebo patients were switched to adalimumab treatment from Weeks 12 to 24. Adalimumab-treated patients experienced a 53.6% mean reduction in spinal SPARCC scores compared with a 9.4% mean increase in scores for placebo-treated patients (P<0.001) at Week 12. The mean percentage reduction in the SI joint SPARCC score was 52.9% for adalimumab-treated patients versus 12.7% for placebo-treated patients (P=0.017). After switching to adalimumab treatment, patients who were initially randomized to receive placebo during the 24-week, double-blind period experienced improvements in SPARCC scores that were similar in magnitude to adalimumab patients at Week 52. Guyatt's effect sizes for the changes in spinal and SI joint SPARCC scores at Week 12 were 1.4 and 0.8, respectively, indicating a large effect by adalimumab on reducing inflammation in both the spinal and SI joints.

Patients who were nonresponders to adalimumab based on clinical assessments, including ASAS20, ASAS40, and ASAS 5/6 responses, experienced statistically significant reductions in spinal and SI joint SPARCC scores by Week 12 that were similar in magnitude to those observed in adalimumab responders (Table 30).

TABLE 30

Comparison of Adjusted Mean Percent Changes (±SE) in Spinal and Sacroiliac Joint SPARCC Scores From Baseline to Week 12 for Clinical Responders and Nonresponders

| Definition of Clinical Response | Baseline to Week 12 Percent Change in Spinal SPARCC Scores, Adjusted Mean ± SE* | | |
|---|---|---|---|
| | Adalimumab | Placebo | P Value† |
| Responders | −52.8 ± 12.3 (n = 17) | 4.7 ± 16.0 (n = 10) | <0.008 |
| Nonresponders | −54.2 ± 13.3 (n = 20) | 10.9 ± 10.7 (n = 31) | <0.001 |
| Responders | −56.2 ± 7.9 (n = 16) | −17.0 ± 18.3 (n = 3) | 0.067 |
| Nonresponders | −51.7 ± 13.5 (n = 21) | 11.5 ± 10.1 (n = 38) | <0.001 |
| Responders | −54.7 ± 15.8 (n = 17) | 33.8 ± 26.6 (n = 6) | 0.009 |
| Nonresponders | −52.7 ± 11.7 (n = 20) | 5.2 ± 8.8 (n = 35) | <0.001 |

| Definition of Clinical Response | Baseline to Week 12 Percent Change in Sacroiliac Joint SPARCC Scores, Adjusted Mean ± SE* | | |
|---|---|---|---|
| | Adalimumab | Placebo | P Value† |
| Responders | −46.7 ± 14.2 (n = 13) | −19.4 ± 16.2 (n = 10) | 0.218 |
| Nonresponders | −60.2 ± 19.9 (n = 11) | −9.2 ± 15.1 (n = 19) | 0.051 |
| Responders | −46.7 ± 15.8 (n = 13) | −36.4 ± 28.4 (n = 4) | 0.757 |
| Nonresponders | −60.2 ± 18.4 (n = 11) | −8.9 ± 12.2 (n = 25) | 0.026 |
| Responders | −42.2 ± 16.4 (n = 12) | −28.5 ± 23.2 (n = 6) | 0.636 |
| Nonresponders | −63.5 ± 17.6 (n = 12) | −8.6 ± 12.7 (n = 23) | 0.016 |

*Patients with a 0 score at baseline were not included in the analysis of percent change.
†P value for change was based on an analysis of variance model with therapy as a factor.
ASAS20 = Assessment in Ankylosing Spondylitis International Working Group 20% response (ie, at least 20% improvement and 1 unit of absolute change in 3 of the 4 following domains: patient's global assessment of disease activity, patient's assessment of pain, function, and inflammation); ASAS40 = ASAS 40% response (ie, at least 40% improvement and 2 units of absolute change in 3 of the 4 domains of the ASAS20 criteria, with no worsening in the fourth domain); ASAS 5/6 = ASAS International Working Group 5/6 criteria (ie, 20% improvement in 5 of 6 domains, consisting of the 4 domains of the ASAS20 criteria plus spinal mobility and acute-phase reactants); SE = standard error; SPARCC = Spondyloarthritis Research Consortium of Canada.

Of the 20 adalimumab-treated patients who were ASAS20 nonresponders at Week 12, 16 had improved spinal SPARCC scores at Week 12. Of these 16, 10 patients were ASAS20 responders at Week 52. The improvements in MRI spinal SPARCC scores for 9 of these 10 patients were sustained at Week 52. Nine of the 20 adalimumab-treated patients who were ASAS20 nonresponders at Week 12 had improved SI joint SPARCC scores at Week 12. Of these 9 patients, 4 were ASAS20 responders at Week 52, and the SI joint SPARCC scores for all 4 patients were sustained at Week 52.

The cumulative probability plot shows that at Week 12, adalimumab-treated patients had a higher probability of improvement in both spinal and SI joint SPARCC scores compared with placebo-treated patients (FIGS. 17 and 18); the curve for adalimumab-treated patients lies to the left of and above the curve for the placebo-treated patients, indicating that virtually all patients treated with adalimumab experienced a reduction in spinal and SI joint inflammation, whereas the curve for placebo patients showed similar numbers of patients experiencing worsening and improvement.

Figure 19:
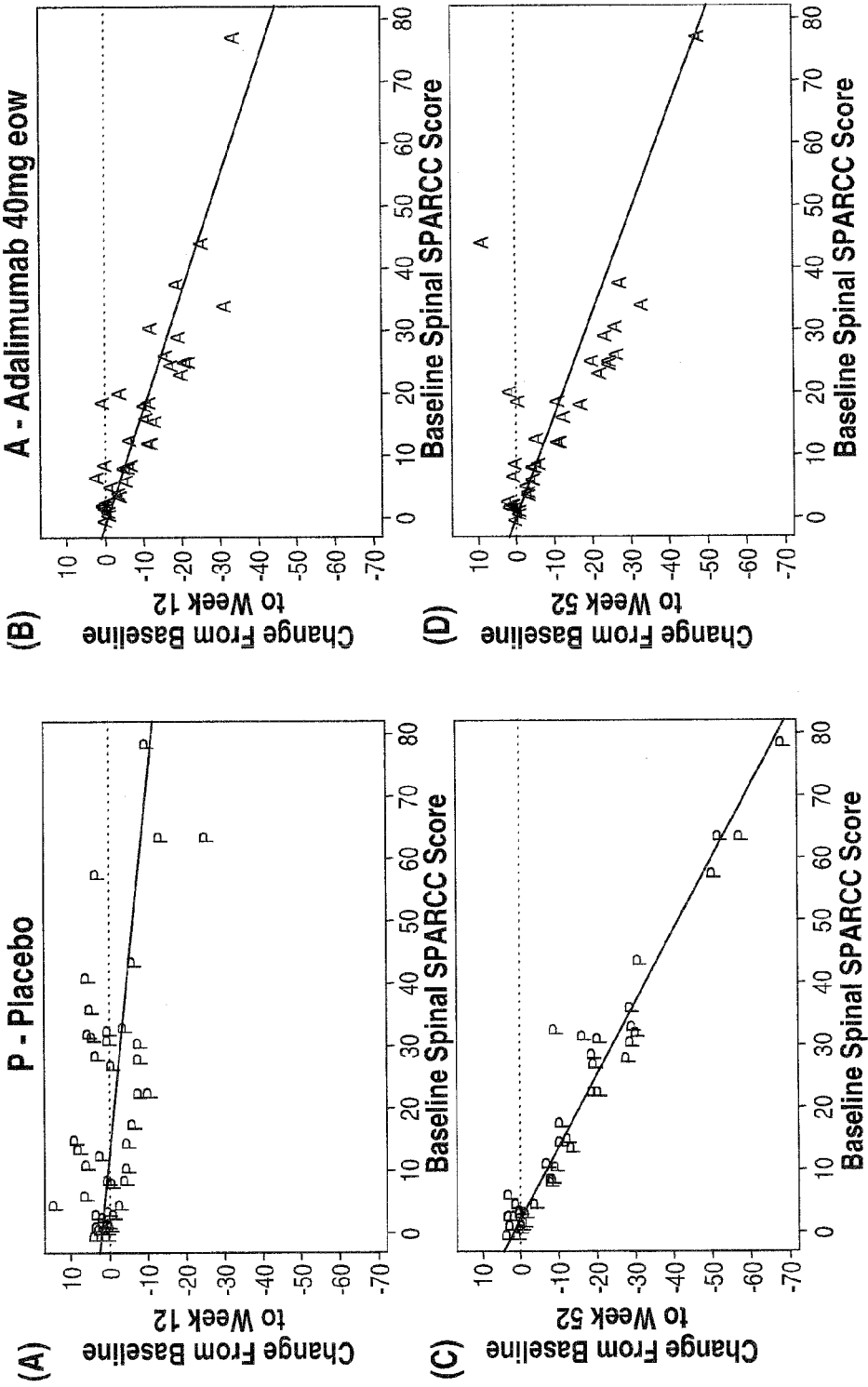
FIG. 19 shows scatter plots of the spinal SPARCC change score versus baseline spinal SPARCC score for patients receiving placebo and adalimumab.

Visual examination of scatter plots of the change in SPARCC scores versus baseline SPARCC scores for each individual patient indicate a consistent treatment effect of adalimumab. A scatter plot of the change in the spinal SPARCC score versus the baseline spinal SPARCC score for each individual patient at Week 12 is shown in FIGS. 19A and 19B and at Week 52, in FIGS. 19C and 19D. FIGS. 19B, 19C, and 19D indicate a consistent treatment effect and no regression to the mean. The scatter plots also indicate that the maximal response to adalimumab in this study was achieved by Week 12 (FIGS. 19B and 19D).

The SPARCC scoring system demonstrated excellent reproducibility between readers in this study. For the change from baseline to Week 12 in spinal and SI joint SPARCC scores, the interreader ICCs were 0.88 and 0.89, respectively. The intrareader reproducibility of change scores was also high. For the 2 MRI readers, the intrareader ICCs for the change from baseline to Week 12 in spinal SPARCC scores were 0.87 and 0.96, respectively. The intrareader ICCs for the change from baseline to Week 12 in the SI joint SPARCC scores were 0.81 and 0.69, respectively.

In the adalimumab-treated patients, mean CRP concentrations were reduced significantly as early as Week 2 and the decrease was maintained at Weeks 4, 8, and 12. A reduced CRP concentration at Week 12 was significantly associated with improvement in spinal SPARCC score (P=0.018) but not SI joint SPARCC score (P=0.590) in the adalimumab group. There were no statistically significant associations between changes in SPARCC index scores at Week 12 and changes in other clinical variables (e.g., BASDAI, BASMI, EDASMI, patient's global assessment, nocturnal pain, and total back pain).

This study demonstrated that adalimumab induces significant, rapid, and almost complete regression of both spinal and SI joint inflammation by 12 weeks in almost all patients as measured by MRI in patients with active AS. Significant reduction of SI joint inflammation has not been previously reported in a randomized controlled trial of an anti-TNF therapy. The maximal reduction in spinal and SI inflammation was achieved by Week 12, and the treatment effect was sustained in both areas for up to 1 year. Patients who were treated with placebo for up to 24 weeks and then switched to adalimumab treatment experienced a similar magnitude of improvement in inflammation at Year 1. Guyatt's effect size for spinal inflammation in our study was 1.4, indicating a very large treatment effect, and the effect size for the SI joint (0.8) also suggests a clinically important benefit of adalimumab for the treatment of active AS.

This study is the largest evaluation of the effect of adalimumab on spinal inflammation as measured by MRI and the only randomized controlled trial to demonstrate significant regression of SI joint inflammation in patients with active AS during TNF antagonist therapy. A reduction in spinal inflammation has been demonstrated for both etanercept and infliximab in patients with AS (Braun et al. Arthritis Rheum 2003; 48:1126-36; Baraliakos et al. Arthritis Rheum 2005; 53:856-63; Baraliakos et al. Arthritis Rheum 2005; 52:1216-23; Rudwaleit et al. Ann Rheum Dis 2005; 64:1305-10. Erratum in: Ann Rheum Dis 2005; 64:1668; Braun et al. Arthritis Rheum 2006; 54:1646-52). However, the largest study that evaluated etanercept included MRI of only the lumbar spine and lower thoracic spine (Baraliakos et al. Arthritis Rheum 2005; 52:1216-23). The ASSERT (Ankylosing Spondylitis Study for the Evaluation of Recombinant Infliximab Therapy) study demonstrated significant reduction in spinal inflammation by MRI at 24 weeks in patients who received infliximab at 5 mg/kg every 6 weeks (Braun et al Arthritis Rheum 2006; 54:1646-52). The current study of adalimumab is the first to show statistically significant reductions, however, in both spinal and SI joint inflammation that were maintained for up to 1 year. Persistent reduction in spinal inflammation as depicted by MRI has previously only been demonstrated in small studies (<30 patients with AS) of etanercept and infliximab, and not with a fully human anti-TNF antibody (Baraliakos et al. Arthritis Rheum 2005; 52:1216-23; Sieper et al. Rheumatology (Oxford) 2005; 44:1525-30).

Another important observation in this study was the finding that significant and comparable reductions in MRI scores for inflammation were evident in ASAS responders and nonresponders who received adalimumab. The SPARCC scoring system demonstrated high reproducibility (interreader ICCs of change scores were 0.88 and 0.89) in this study, showing the validity of this MRI-based method for objectively measuring the presence and extent of inflammation in both the spine and the SI joints of patients with AS in a clinical trial setting. The SPARCC MRI index has many features that may make it particularly advantageous for use in clinical trials of therapeutic agents for the treatment of AS. Because no contrast agent is required, the cost associated with each MRI is reduced, as is the burden on the patient. The scoring system also takes advantage of the ability of MRI to delineate lesions in 3 dimensions by evaluating lesions in consecutive sagittal slices so that it is possible to quantify the extent of each lesion in antero-posterior, cranio-caudal, and left-right directions. This is important because inflammatory lesions are often asymmetrical and may be extensive in 1 dimension only. Scoring of a particular lesion in, for example, a single sagittal slice will only capture information in the cranio-caudal and antero-posterior axes and cannot reliably record the burden of disease or fluctuation of the inflammatory process if such changes were to occur predominantly in the left-right direction. Finally, digitizing and electronically storing MRIs allows MRI readers in diverse locations to access and score scans quickly and efficiently—application of the SPARCC scoring system requires only 15 minutes per case.

In conclusion, adalimumab significantly reduced both spinal and SI joint inflammation in patients with active AS after 12 weeks of treatment, and the reduction in inflammation was maintained for at least 52 weeks. Patients receiving adalimumab showed MRI evidence of significant reduction in spinal inflammation even in those patients who were ASAS nonresponders. The study also demonstrated that the SPARCC MRI scoring method is reliable, feasible, and therefore valid for use in clinical trials of patients with AS.

Example 6

Adalimumab Reduces Pain and Fatigue in Ankylosing Spondylitis (AS) Patients

Pain and fatigue are two of the most prevalent quality of life concerns among patients with ankylosing spondylitis (AS). This study examined the ability of adalimumab to alleviate pain, fatigue and enthesitis in patients with active AS.

Study H was a 24-week, randomized, placebo (PBO)-controlled, double-blind, Phase III study. Patients received either adalimumab (ADA) 40 mg every other week or PBO for 24 weeks. Pain levels were assessed by Total Back Pain (TBP) VAS, Nocturnal Pain (NP) VAS (both at Baseline [BL] and Wks 2, 8, 12, 16, 20, 24), the SF-36 Bodily Pain domain (BL and Wks 12, 24). The BASDAI fatigue item (BL and Wks 2, 8, 12, 16, 20, 24), and the SF-36 Vitality domain (BL, and Wks 12, 24) measured fatigue. Enthesitis was assessed with the BASDAI enthesitis item (BL and Wks 2, 8, 12, 16, 20, 24). See FIG. 1 for a graphical representation of the study design.

Study H measured pain assessments by recording: Total Back Pain visual analog scale (VAS): patient-reported-outcomes (PRO) questionnaire assessing the amount of back pain at any time during the last week, scores range from 0-100, with lower scores reflecting less pain; Nocturnal Pain VAS: PRO questionnaire assessing the amount of back pain at night during the last week, scores range from 0-100, with lower scores reflecting less pain; SF-36 Bodily Pain domain, assessing overall bodily pain during the past 4 weeks. Domain scores range from 0-100, with higher scores reflecting less pain. A 5-10 point change in domain scores is considered clinically meaningful. The SF-36 consists of eight domains: physical functioning, role-physical, social functioning, general health, bodily pain, vitality, role-emotional, mental health.

Fatigue assessments were also measured by recording: The first item of the Bath Ankylosing Spondylitis Disease Activity Index (BASDAI), asking the patient to rate "overall degree of tiredness" during the past 7 days on VAS, with scores range from 0-10, lower scores representing less fatigue; SF-36 Vitality domain, also one of the 8 domains of SF-36, measures energy level and fatigue. Scores range from 0-100, with higher scores reflecting less fatigue. A 5-10 point change in domain scores is considered clinically meaningful.

Enthesitis assessments were measured by the 4th item of the BASDAI, asking the patient to rate overall level of discomfort in any areas tender to touch or pressure during the past 7 days on VAS, with scores range from 0-10, lower scores representing less enthesitis and Maastricht AS Enthesitis Score (MASES), which is a physician's assessment of patient response to firm palpation at 13 specific spinal and sacroiliac joints. Scores range from 0-13, with lower scores indicating less enthesitis.

TABLE 32

Schedule of Assessments

| Outcome Measure | BL | 2 | 8 | 12 | 16 | 20 | 24 |
|---|---|---|---|---|---|---|---|
| Total Back Pain | X | X | X | X | X | X | X |
| Nocturnal Pain | X | X | X | X | X | X | X |
| SF-36 | X |  |  | X |  |  | X |
| BASDAI | X | X | X | X | X | X | X |
| MASES | X |  |  | X |  |  | X |

The study comprised 315 patients (ADA n=208, PBO n=107). At BL, both arms had comparable demographics, disease characteristics, and pain/fatigue measurements. Rapid and significant improvement occurred as early as 2 wks for patients treated with ADA vs. PBO in TBP (−19.5 [95% CI, −23.0 to −16.0] vs. −6.02 [95% CI, −9.8 to −2.2]), NP (−19.2 [95% CI, −22.4 to −16.1] vs. −3.8 [95% CI, −7.4 to −0.2]), BASDAI fatigue (−1.1 vs. −0.3, p<0.001) and BASDAI enthesitis (−1.79 vs. −0.62, p<0.001). At Weeks 12 and 24, this improvement was maintained in all the above measures and appeared in the SF-36 Bodily Pain and Vitality domains (Table 33).

TABLE 33[†]

|  | Baseline | | Week 12 Change from Baseline | | Week 24 Change from Baseline | |
|---|---|---|---|---|---|---|
|  | PBO | ADA | PBO | ADA | PBO | ADA |
| Pain: | | | | | | |
| TBP | 67.2 | 64.6 | −8.4 | −27.3* | −9.0 | −27.7* |
| NP | 64.6 | 60.7 | −8.0 | −26.0* | −8.7 | −27.3* |
| SF-36 Bodily Pain | 29.8 | 31.7 | 6.7 | 19.2* | 7.1 | 20.7* |
| Fatigue: | | | | | | |
| BASDAI Fatigue | 6.7 | 6.5 | −0.7 | −2.2* | −0.7 | −2.3* |
| SF-36 Vitality | 34.0 | 32.6 | 6.4 | 13.1[#] | 5.6 | 14.7* |
| Enthesitis: | | | | | | |
| BASDAI Enthesitis | 5.9 | 5.7 | −0.9 | −2.5* | −0.91 | −2.4* |

[†]All values LOCF.
*P < 0.001, mean change from BL compared with PBO.
[#]P = 0.005.

Baseline demographics and clinical characteristics were comparable between treatment groups (Table 34).

TABLE 34

|  | Placebo (N = 107) | ADA 40 mg eow (N = 208) |
|---|---|---|
| Age, years* | 43.4 | 41.7 |
| Male, n (%) | 79 (73.8) | 157 (75.5) |
| Caucasian, n (%) | 99 (92.5) | 202 (97.1) |
| Weight, kg* | 79.8 | 81.9 |
| HLA-B27 positive, n (%) | 85 (79.4) | 163 (78.4) |
| Disease duration, years* | 10.0 | 11.3 |
| Total Back Pain* | 67.2 | 64.6 |
| Nocturnal Pain* | 64.6 | 60.7 |
| SF-36 Bodily Pain* | 29.8 | 31.7 |
| BASDAI Fatigue* | 6.7 | 6.5 |
| SF-36 Vitality* | 34.0 | 32.6 |
| MASES* | 6.7 | 6.4 |
| BASDAI Enthesiits* | 5.9 | 5.7 |

Patient disposition and completion rates are summarized in Table 35 below.

TABLE 35

Disposition of Patients
315 Randomized

| 107 Randomized to placebo | 208 Randomized to adalimumab |
|---|---|
| 103 patients completed week 12 | 204 patients completed week 12 |
| 4 patients discontinued by week 12 | 4 patients discontinued by week 12 |
| 2 adverse events | 2 adverse events |
| 1 lost to follow up | 2 withdrew consent |
| 2 other reasons | 2 other reasons |
| 101 patients completed week 24 | 195 patients completed week 24 |
| 6 patients total discontinued by week 24 | 13 patients total discontinued by week 24 |
| 2 adverse events | 5 adverse events |
| 1 withdrew consent | 5 withdrew consent |
| 1 lost to follow up | 1 lost to follow up |
| 4 other reasons | 2 other reasons |

Patients can have multiple reasons for discontinuation.

Pain Reduction figures are shown in Tables 36-38 below. They show that by Week 2, significant reductions in Total Back Pain and Nocturnal Pain scores were observed in patients treated with adalimumab compared with placebo. These improvements were maintained for at least 24 weeks. Significant improvements in SF-36 Bodily Pain domain scores were also observed at Weeks 12 and 24.

TABLE 36

Reduction in Total Back Pain

| | Mean Change from Baseline | |
|---|---|---|
| | Placebo | Adalimumab |
| Week 2 | −6.0 | −19.5* |
| Week 12 | −8.4 | −27.3[†] |
| Week 24 | −9.0 | −27.7[†] |

*ADA (95% CI, −23.0 to −16.0) vs. placebo (95% CI, −9.8 to −2.2).
[†]p < 0.001 vs. placebo.

TABLE 37

Reduction in Nocturnal Pain

| | Mean Change from Baseline | |
|---|---|---|
| | Placebo | Adalimumab |
| Week 2 | −3.8 | −19.2* |
| Week 12 | −8.0 | −26.0† |
| Week 24 | −8.7 | −27.3† |

*ADA (95% CI, −22.4 to −16.1) vs. placebo (95% CI, −7.4 to −0.2).
†p < 0.001 vs. placebo.

TABLE 38

Improvement in SF-36 Bodily Pain Domain Score

| | Mean Change from Baseline | |
|---|---|---|
| | Placebo | Adalimumab |
| Week 12 | 6.7 | 19.2* |
| Week 24 | 7.1 | 20.7* |

*p < 0.001 vs. placebo.
MCID = 10; MCID = Minimum clinically important difference. Kosinski M et al. Arthritis Rheum 2000; 7: 1478-1487.

Fatigue Improvement figures are shown in Tables 39 and 40. They show an early significant improvement in BASDAI fatigue scores was observed after 2 weeks, and maintained for at least 24 weeks, in patients receiving adalimumab therapy compared with placebo. Significant improvements in SF-36 Vitality domain scores at Weeks 12 and 24 were also noted.

TABLE 39

Reduction in BASDAI Fatigue Score

| | Mean Change from Baseline | |
|---|---|---|
| | Placebo | Adalimumab |
| Week 2 | −0.3 | −1.1* |
| Week 12 | −0.7 | −2.2* |
| Week 24 | −0.7 | −2.3* |

*p < 0.001 vs. placebo.

TABLE 40

Improvement in SF-36 Vitality Domain Score

| | Mean Change from Baseline | |
|---|---|---|
| | Placebo | Adalimumab |
| Week 12 | 6.4 | 13.1* |
| Week 24 | 5.6 | 14.7† |

*p = 0.005 vs. placebo.
†p < 0.001 vs. placebo.
‡MCID = 10; MCID = Minimum clinically important difference. Kosinski M et al. Arthritis Rheum 2000; 7: 1478-1487.

Figure 20:
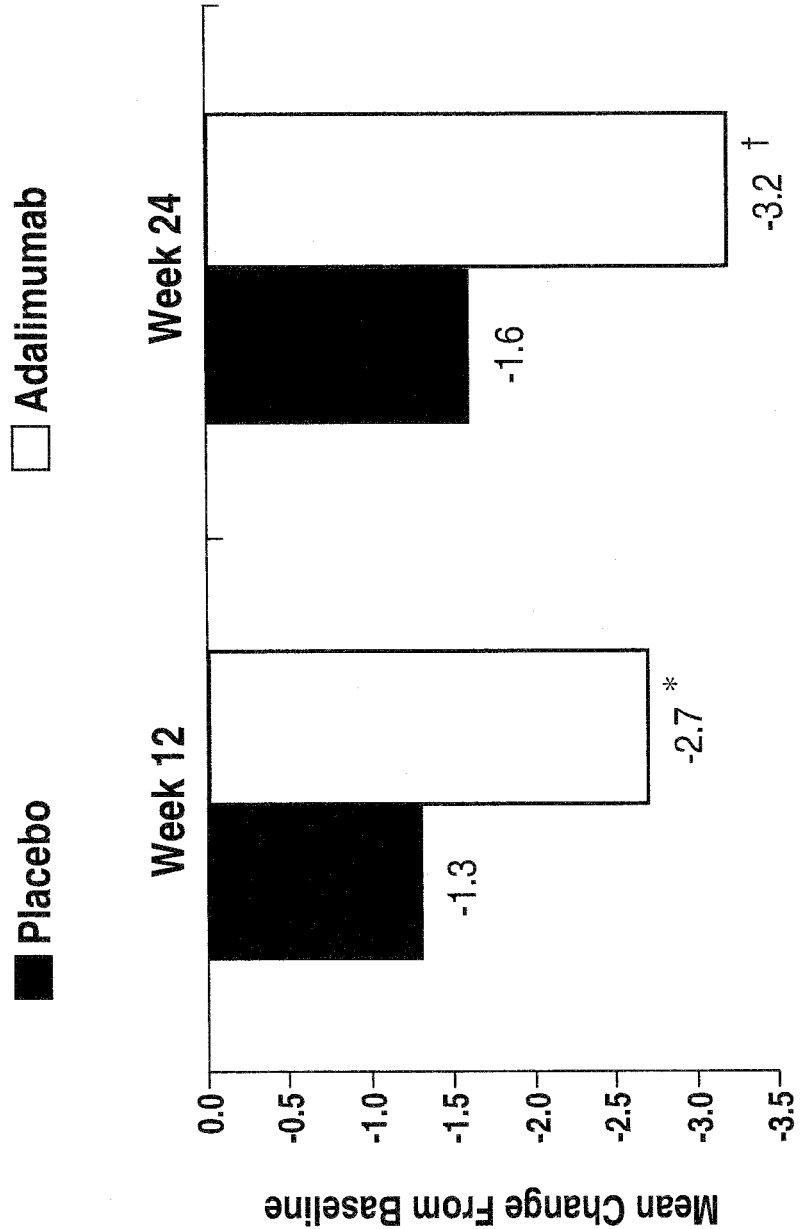
FIG. 20 graphically depicts a reduction in MASES for patients in the study of example 6.

Enthesitis Reduction results are shown in Table 41 and FIG. 20. They show that after 2 weeks of treatment, a significant reduction in BASDAI enthesitis scores and MASES was observed among patients receiving adalimumab therapy. These improvements were maintained for at least 24 weeks.

TABLE 41

Reduction in BASDAI Enthesitis Score

| | Mean Change from Baseline | |
|---|---|---|
| | Placebo | Adalimumab |
| Week 2 | −0.6 | −1.8* |
| Week 12 | −0.9 | −2.5* |
| Week 24 | −0.9 | −2.4* |

*p < 0.001 vs. placebo.

In sum, this study indicated that adalimumab rapidly and significantly reduces pain, fatigue, and enthesitis in patients with AS; this improvement is maintained for at least 24 weeks of treatment.

Example 7

TNF-Antagonist Therapy in Patients with Ankylosing Spondylitis

In Vitro Observations of T-Cell Responsiveness to Recall Antigens During Therapy Reactivation of tuberculosis (TB) and other infectious diseases has been described in AS patients under therapy with anti-TNF therapy. However, T-cell responses to immunodominant T-cell antigens during therapy with TNF antagonists have never been analysed.

To examine the relationships between clinical response and risk for infection activation with the concentrations of antigen-specific T-cells in AS patients treated with TNF-antagonist therapy.

Peripheral blood from 8 AS patients was collected, who received the fully human, anti-tumour-necrosis-factor monoclonal antibody adalimumab 40 mg subcutaneously every other week before therapy and after 12 weeks of therapy. The Bath Ankylosing Spondylitis Disease Activity Index (BASDAI) was measured at both time points as well. Fresh peripheral blood mononuclear cells (PBMNC) were stimulated with Bacille Calmette-Guérin (BCG) vaccine, ESAT-6 proteins from *Mycobacterium tuberculosis*, tetanus toxoid, and cytomegaly virus antigen. Interferon-gamma secretion (IFN-gamma) was analysed after antigen-specific, in vitro stimulation for 6 hours by intracellular cytokine staining and flow cytometry. For control experiments, stimulation with CD28 and staphylococcus enterotoxin B (SEB) was performed.

All AS patients reported a major benefit from anti-TNF therapy with adalimumab. The mean BASDAI decreased from 5.43 before therapy to 1.36 after 12 weeks of therapy. Intracellular IFN-gamma staining after antigen-specific, in vitro stimulation of PBMNC had not changed in 4 AS patients. In 3 AS patients, IFN-gamma production decreased significantly during adalimumab therapy. In another AS patient, IFN-gamma production after antigen-specific stimulation increased, but not significantly. There was no correlation between a decrease in the BASDAI and a decrease in the T-cell response.

In sum, data from 8 AS patients suggest that a deletion of antigen-specific T cells is not necessary to achieve clinical response with anti-TNF therapy, as neutralizing soluble TNF may be sufficient. Patients showing a decrease in specific T-cell responses to antigens, such as *Mycobacterium tuberculosis*, may be at higher risk of reactivation of latent-TB or other intracellular infections.

Example 8

Efficacy of Adalimumab for Treatment of Ankylosing Spondylitis

The efficacy of Humira 40 mg every other week was assessed in 393 patients in two randomised, 24 week double—blind, placebo—controlled studies in patients with active ankylosing spondylitis (mean baseline score of disease activity [Bath Ankylosing Spondylitis Disease Activity Index (BASDAI)] was 6.3 in both the Humira and the placebo groups) who have had an inadequate response to conventional therapy. Glucocorticoids, salicylates, non-steroidal anti-inflammatory drugs, analgesics or disease modifying anti-rheumatic drugs were continued during the study with Humira. The blinded period was followed by an open-label period during which patients received Humira 40 mg every other week subcutaneously for up to an additional 236 weeks.

In the larger study with 315 patients, results showed statistically significant improvement of the signs and symptoms of ankylosing spondylitis in patients treated with Humira compared to placebo. Significant response was first observed at Week 2 and maintained through 24 weeks (Table 42).

Patients with total spinal ankylosis were included in the larger study (n=11). Responses of these patients were similar to those patients without total ankylosis.

TABLE 42

Efficacy Responses in Placebo-Controlled AS Study - Study H Reduction of Signs and Symptoms

| Response* | Placebo N = 107 | Humira N = 208 |
|---|---|---|
| ASAS[a] 20 | | |
| Week 2 | 16% | 42% |
| Week 12 | 21% | 58% |
| Week 24 | 19% | 51% |
| ASAS 50 | | |
| Week 2 | 3% | 16% |
| Week 12 | 10% | 38% |
| Week 24 | 11% | 35% |
| ASAS 70 | | |
| Week 2 | 0% | 7% |
| Week 12 | 5% | 23% |
| Week 24 | 8% | 24% |
| BASDAI[b] 50 | | |
| Week 2 | 4% | 20% |
| Week 12 | 16% | 45% |
| Week 24 | 15% | 42% |

*statistically significant as $p < 0.001$ for all comparisons between Humira and placebo at Weeks 2, 12 and 24
[a]Assessments in Ankylosing Spondylitis
[b]Bath Ankylosing Spondylitis Disease Activity Index Humira treated patients had significantly greater improvement at Week 12 which was maintained through Week 24 in both the SF36 and Ankylosing Spondylitis Quality of Life Questionnaire (ASQoL).

Similar results were seen in the smaller randomised, double-blind, placebo controlled study of 82 adult patients with active ankylosing spondylitis.

Example 9

Cost Effectiveness of Adalimumab Therapy vs. Conventional Care in the United Kingdom (UK) Patients with Active Ankylosing Spondylitis (AS)

Tumor necrosis factor (TNF) antagonists have been demonstrated to significantly reduce the signs and symptoms and improve health-related quality of life (HRQL) in AS patients (pts). The objective of this study was to evaluate the cost effectiveness of adalimumab vs. conventional care in pts with active AS when used according to the British Society of Rheumatology (BSR) Guidelines for Prescribing TNFα Blockers in Adults with Ankylosing Spondylitis The analysis was based on the pooled data from two placebo-controlled, Phase III studies (including Study H) of active AS pts who had an inadequate response to at least one NSAID. Pts were randomized to either adalimumab 40 mg every other week (n=246) or placebo (n=151) for 24 weeks. A microsimulation model was developed based on the International ASAS Consensus Statement and the British Society of Rheumatology Guidelines for the use of TNF antagonists in AS patients to reflect real-world treatment decisions and to project long-term outcomes. Specifically, patients were assumed to stay on therapy as long as they had an adequate therapeutic response (i.e., reduction of BASDAI score to 50% or =>2 units, and reduction of spinal pain VAS by >=2 cm), but were withdrawn from therapy when insufficient response occurred. Discontinuations due to adverse events (AEs) or reasons other than therapeutic failures were also considered. Data from the pooled trials, the Outcome Assessment in AS International Study (OASIS) observational database, and the published literature were used to model the trend of patients' BASDAI and BASFI over time and the costs and HRQL associated with various disease severity levels. Costs of AS, drug, administration, monitoring, hospitalization, and AEs were calculated for each patient from the healthcare perspective of the UK NHS. Time lost due to AS or seeking care was also included in a separate analysis from a societal perspective. All costs were in 2004 British £ Discounting was applied at 3.5%/year for both costs and benefits in the base case as recommended by the NICE methodological reference case for economic evaluations. Uncertainty surrounding outcomes was addressed via bootstrapping and probabilistic sensitivity analyses (PSA).

The study measured the following outcomes: Disease progression; Direct costs affecting the NHS; Quality adjusted life expectancy; and incremental cost per quality adjusted life years (QALY) gained at 1, 5, and 30 years.

A Microsimulation model was used to predict future disease progression, quality of life, survival rates, and costs of individual AS patients, according to BSR treatment guidelines which uses trial data: Up to Week 48, with last observation carried forward analysis as necessary and simulates beyond trial data: Week 49 to Year 30, based on assumptions regarding discontinuation rate, long-term efficacy, and long-term disease progression.

Patients were taken from two adalimumab trials (pooled): The Study H trial: 24-week, randomized, placebo-controlled, double-blind, Phase III studies conducted in the US/Europe and Canada, respectively. Patients in the trials were allowed to continue their baseline NSAIDs or DMARDs; therefore, the placebo arm was assumed to represent conventional care for AS. The model included only those trial patients who met treatment eligibility criteria as defined by the BSR.

Treatment response defined by BSR in term of minimum improvements in BASDAI and pain visual analogue scale (VAS) was measured by a reduction of BASDAI to 50% of the pre-treatment value or a fall of ≥2 units and a reduction of the spinal pain VAS by ≥2 cm.

Figure 21:
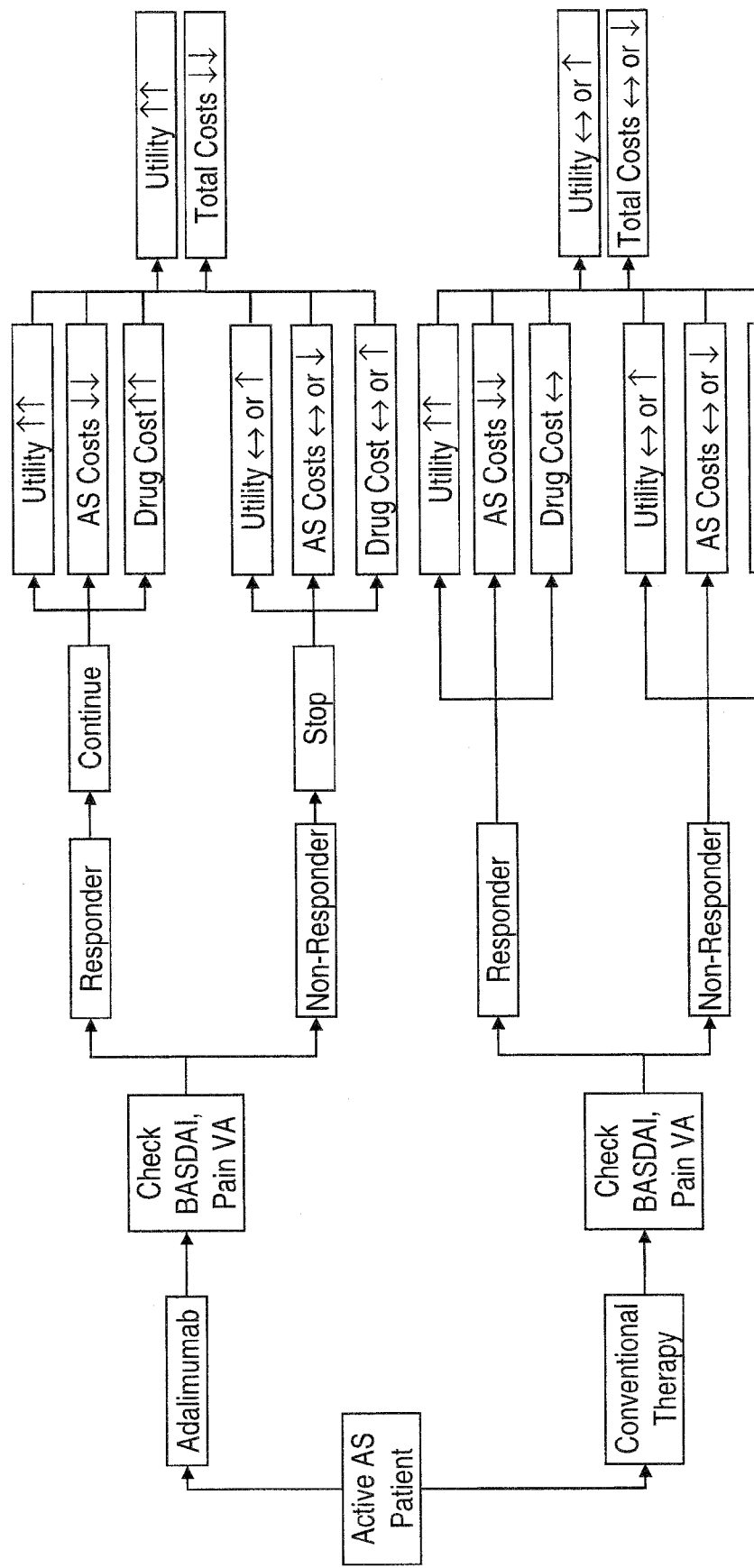
FIG. 21 graphically depicts the conceptual structure of the study.

Follow up clinical management was conducted as described in FIG. 21. Responders were assumed to continue adalimumab therapy and experience better clinical outcomes, lower cost of care, and better quality of life than non-responders.

Non-responders were assumed to stop therapy. Assigned clinical outcomes were consistent with those of conventional care alone.

BASDAI is a six-item measure of disease activity and includes questions on fatigue, spinal pain, peripheral arthritis, enthesitis, and duration and severity of morning stiffness. Items are related to the past 7 days and are answered on a 10 cm visual analogue scale (VAS). The score ranges from 0 to 10, with lower scores reflecting less disease activity.

BASFI is a set of 10 questions designed to determine the degree of functional limitation in those with AS. Items are related to the past 7 days and are answered on a 10 cm visual analogue scale (VAS). The score ranges from 0 to 10, with lower scores reflecting less function limitation.

| Assumed annual disease progression (Year 1-Year 30) | | |
|---|---|---|
| | BASDAI | BASFI |
| Conventional Care | 0 units/year | 0.05 units/year |
| Adalimumab | 0 units/year | 0 units/year |

Pain VAS not included in long-term projection due to lack of data on long-term progression pattern. Assumed treatment discontinuations (Year 1-Year 30). 10% of patients discontinued adalimumab per year. Discontinuers assigned clinical outcomes consistent with those of conventional care alone.

Utility measures were measured in the two adalimumab trials by the Health Utilities Index-3 (HUI-3), which records the patient's preference of different health states on scale of 0 to 1, with a higher score representing better health utility. The relationship between utility and BASDAI or BASFI analyzed using the trial data.

Cost of AS disease was based on 2-year OASIS (Outcomes in Ankylosing Spondylitis International Study) registry of AS patients in the Netherlands, Belgium, and France. OASIS data was used to predict: Resource use by BASDAI, including cost of visits to general practitioner, specialist and physiotherapy, paramedical visits, hospitalization, technical examinations, adaptation and aids, and formal care; Other resources by BASDAI, including private household help, informal care, exercise sessions, time taken off for treatment and sick leave; Prices of resource use obtained from various UK tariffs (e.g., Personal Social Services Research Unit, NHS Trust Reference Cost Index).

Cost related to adalimumab therapy included self-administered adalimumab (£357.50/course); Tuberculosis screening; efficacy monitoring visits with rheumatologists (per BSR guidelines); routine safety monitoring resource use patterns consistent with British recommendations; adverse Events (AEs), including cases of tuberculosis. Uncertainty in economic modeling assessed via univariate sensitivity analyses, bootstrapping and probabilistic sensitivity analyses (PSA), which involved 1,000 model simulations using input values drawn from probability distributions. PSA is a standard requirement by NICE for evaluating uncertainty.

The results show that in the base case, after 30 years, a patient treated with adalimumab was estimated to gain 1.03 quality-adjusted life years (QALY) at a cost of £23,857 relative to patients treated with conventional care. The incremental costs were broken down into additional drug costs at £30,999, screening/monitoring costs at £3,230, and AE related treatment costs at £378, while savings from AS treatment related costs were at £10,750. Incremental cost per QALY gained was estimated for 1 year, 5 year and 30 year time horizons. The incremental cost-effectiveness ratio (ICER) was £23,097 per QALY for adalimumab vs. conventional care in the base case, and was below £30,000 in 70% PSA simulations. When a societal perspective was adopted, the net costs of adalimumab vs. conventional care decreased to £5,260 and the ICER decreased to £5,093 per QALY, which was below £30,000 in 89% of the PSA simulations.

Figure 22:
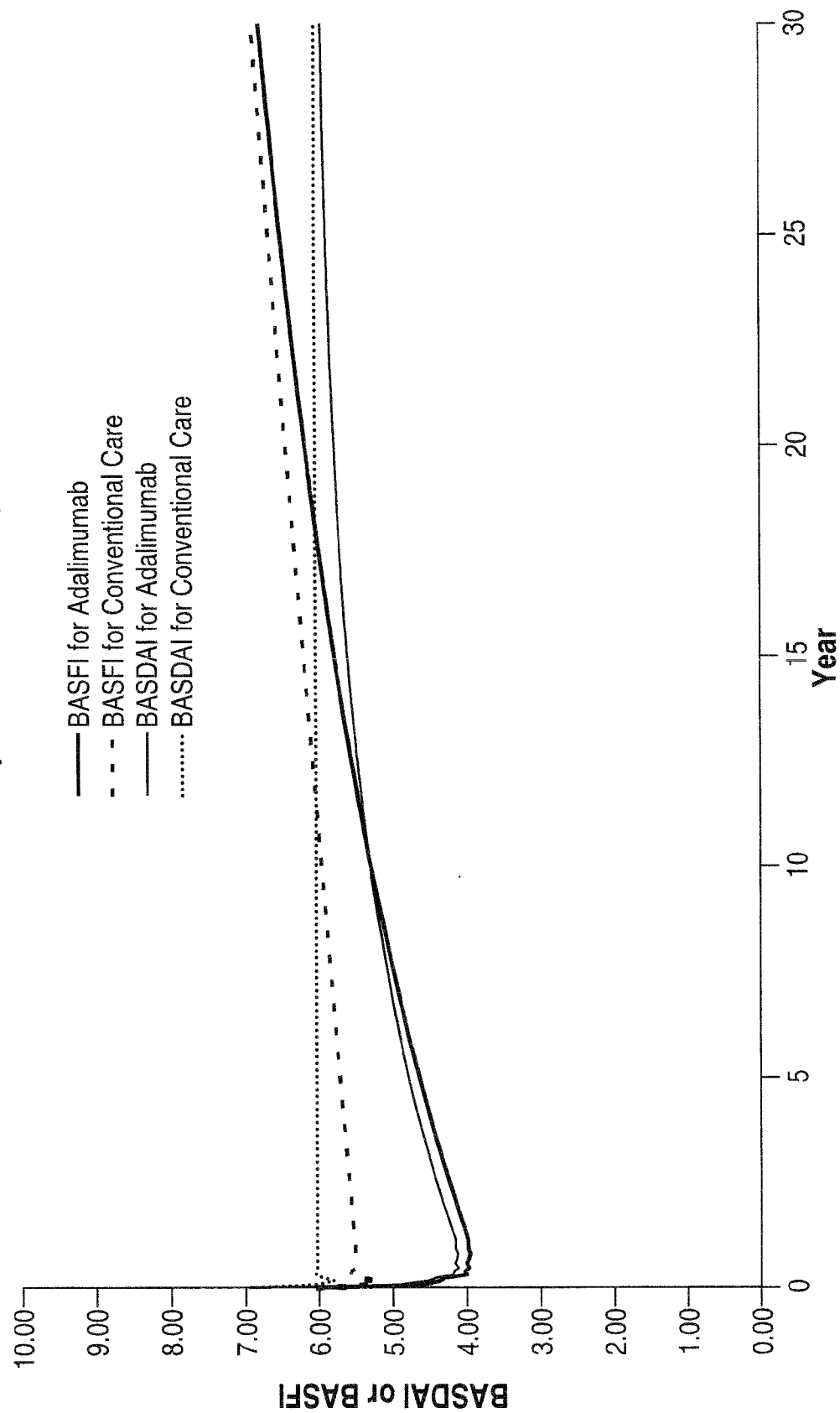
FIG. 22 graphically depicts the Projected Disease Progression.

Patients on adalimumab experienced greater and more sustained improvements in BASDAI and BASFI than patients receiving conventional therapy (FIG. 22). This benefit is very gradually lost over time as it is assumed that (a) 10% of remaining patients on adalimumab discontinue therapy every year and (b) patients discontinuing therapy are assigned clinical outcomes consistent with those of conventional care alone

TABLE 43

Base Case Cost Effectiveness Results

| | 1 year | | | 5 Year | | | 30 Year | | |
|---|---|---|---|---|---|---|---|---|---|
| | Conventional therapy | adalimumab | Difference | Conventional therapy | adalimumab | Difference | Conventional therapy | adalimumab | Difference |
| QALY (per Patient) | 0.4461 | 0.5529 | 0.1067 | 2.1613 | 2.6653 | 0.5041 | 8.1891 | 9.2220 | 1.0329 |
| AS-Specific Costs £ | 4,832 | 3,668 | −1,164 | 23,529 | 18,136 | −5,394 | £92,080 | 81,330 | −10,750 |
| Adalimumab Costs £ | | 6,189 | 6,189 | | 18,666 | 18,666 | | 34,607 | 34,607 |
| Drug Costs £ | | 5,233 | 5,233 | | 16,566 | 16,566 | | 30,999 | 30,999 |
| Monitoring Costs £ | | 905 | 905 | | 1,929 | 1,929 | | 3,230 | 3,230 |
| AE Costs £ | | 51 | 51 | | 171 | 171 | | 378 | 378 |
| Total (per Patient) £ | 4,832 | 9,857 | 5,025 | 23,529 | 36,802 | 13,273 | £92,080 | 115,937 | 23,857 |
| Incremental | | | 47,083 | | | 26,332 | | | 23,097 |

TABLE 43-continued

<table>
<tr><th colspan="10">Base Case Cost Effectiveness Results</th></tr>
<tr><th colspan="3">1 year</th><th colspan="3">5 Year</th><th colspan="3">30 Year</th></tr>
<tr><th>Conventional therapy</th><th>adalimumab</th><th>Difference</th><th>Conventional therapy</th><th>adalimumab</th><th>Difference</th><th>Conventional therapy</th><th>adalimumab</th><th>Difference</th></tr>
<tr><td>Cost per QALY Gained £</td><td></td><td></td><td></td><td></td><td></td><td></td><td></td><td></td></tr>
</table>

Figure 23:
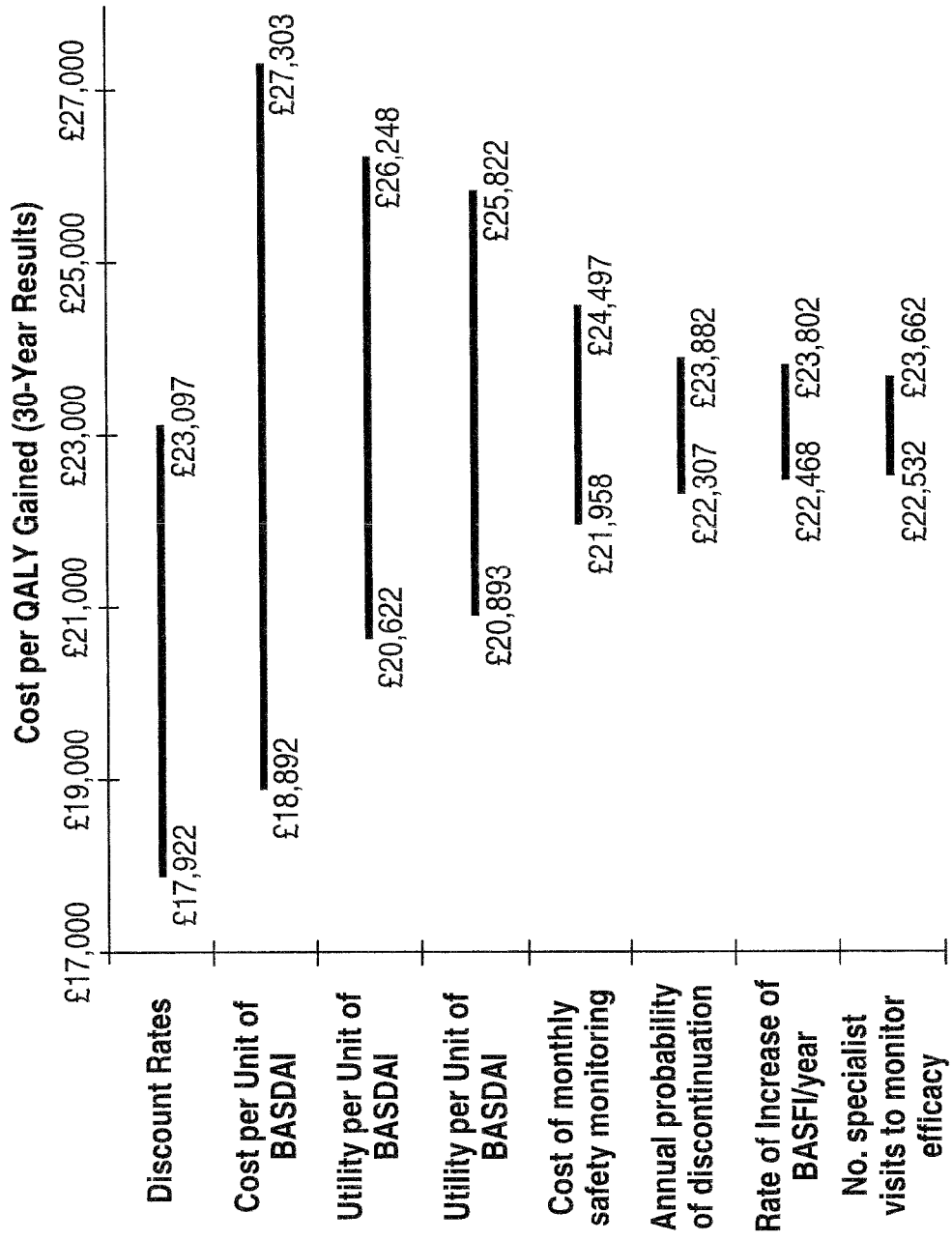
FIG. 23 graphically depicts a Univariate Sensitivity Analysis
Figure 24:
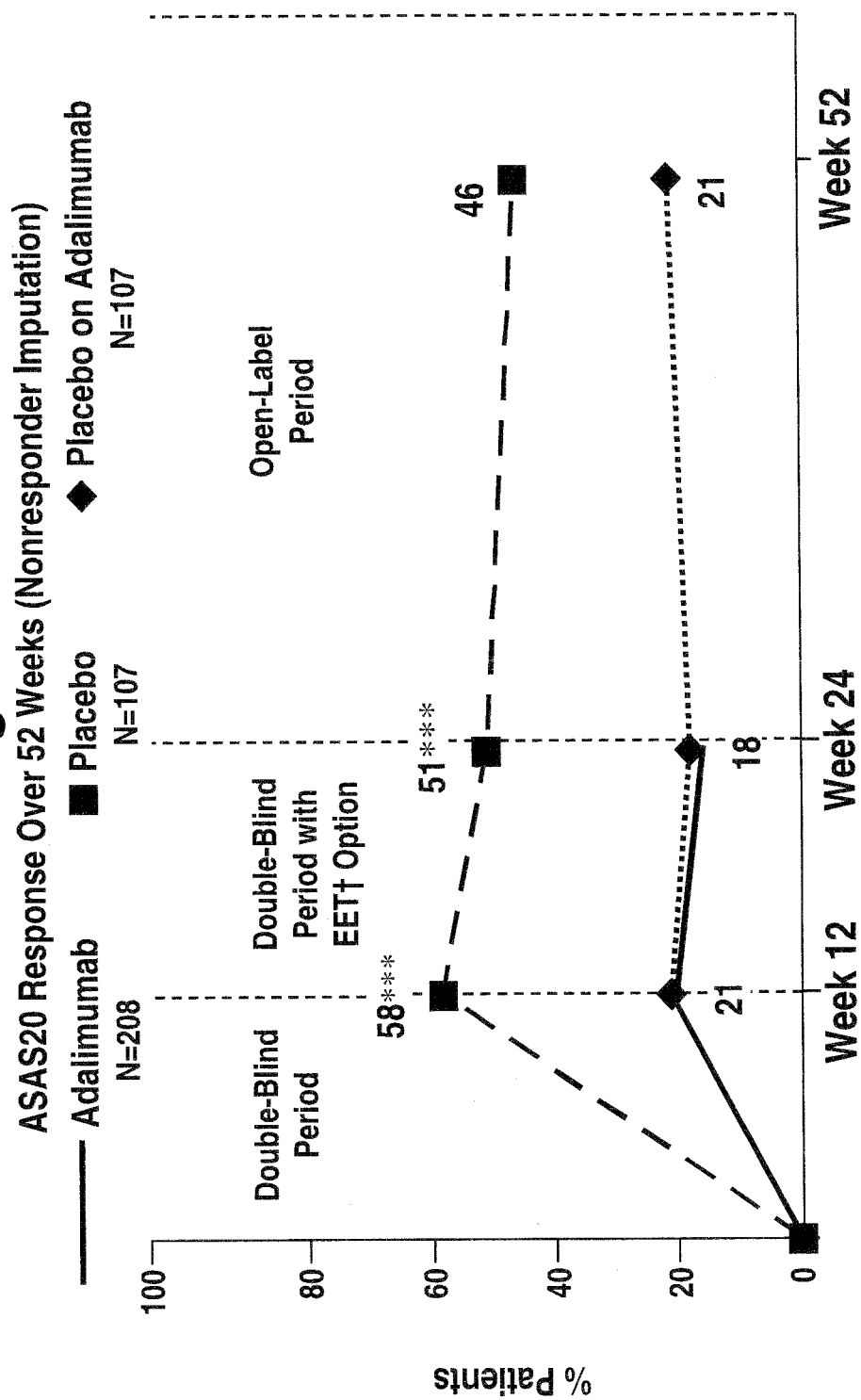
FIG. 24 graphically depicts ASAS20 Response Over 52 Weeks (Nonresponder Imputation).
Figure 25:
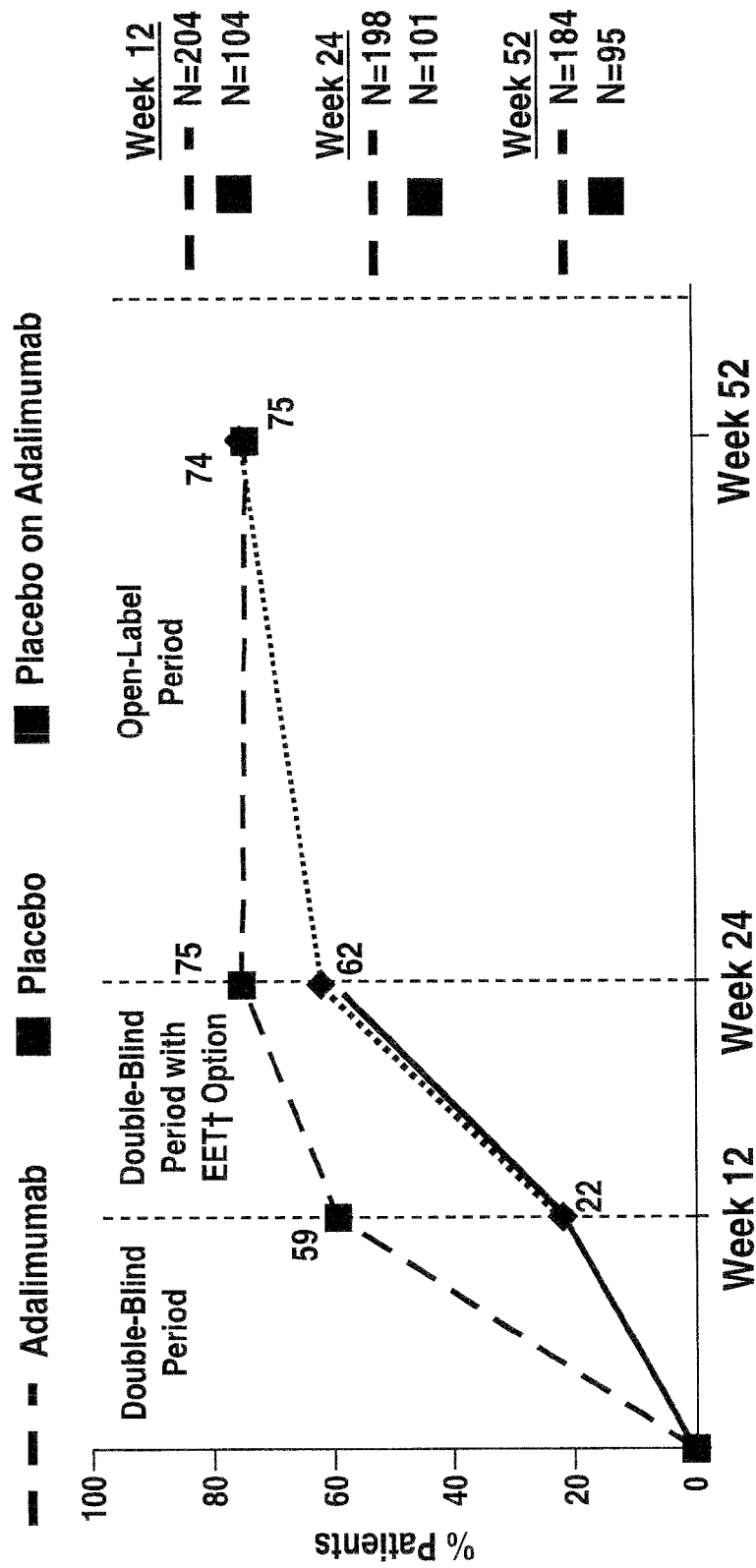
FIG. 25 graphically depicts ASAS20 Response over 52 weeks (Observed).
Figure 26:
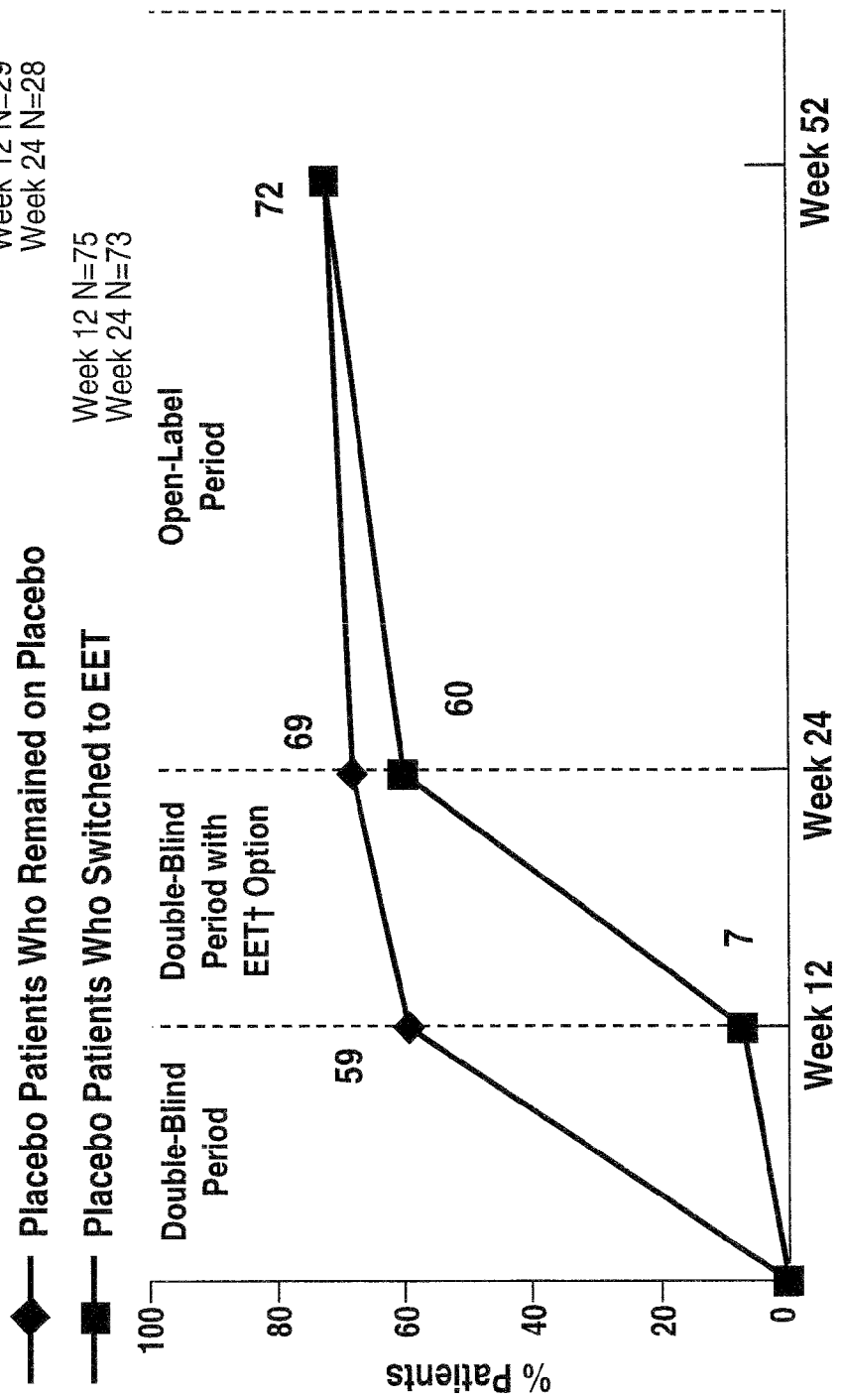
FIG. 26 graphically depicts ASAS20 Response over 52 weeks of placebo patients and early-escape therapy subset (observed).
Figure 27:
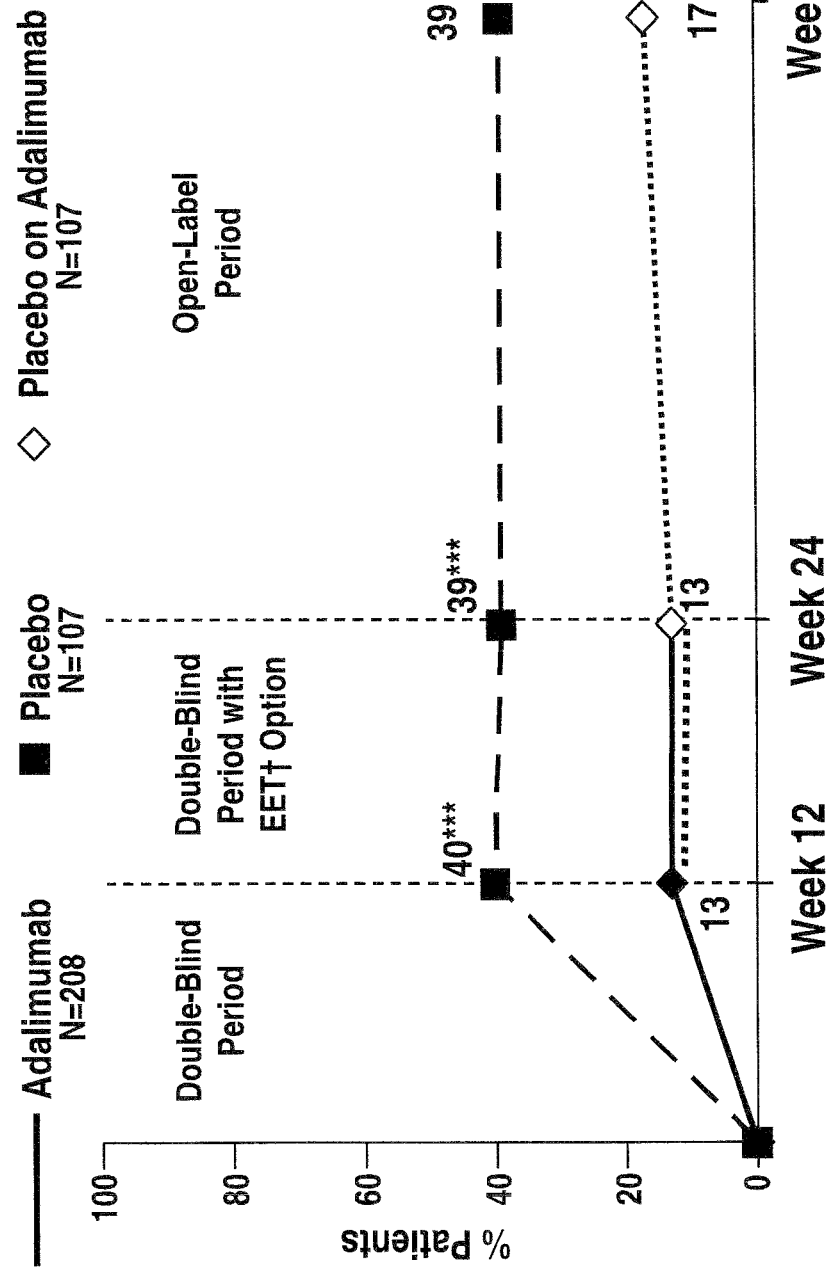
FIG. 27 graphically depicts ASAS40 Response over 52 weeks (Nonresponder Imputation).
Figure 28:
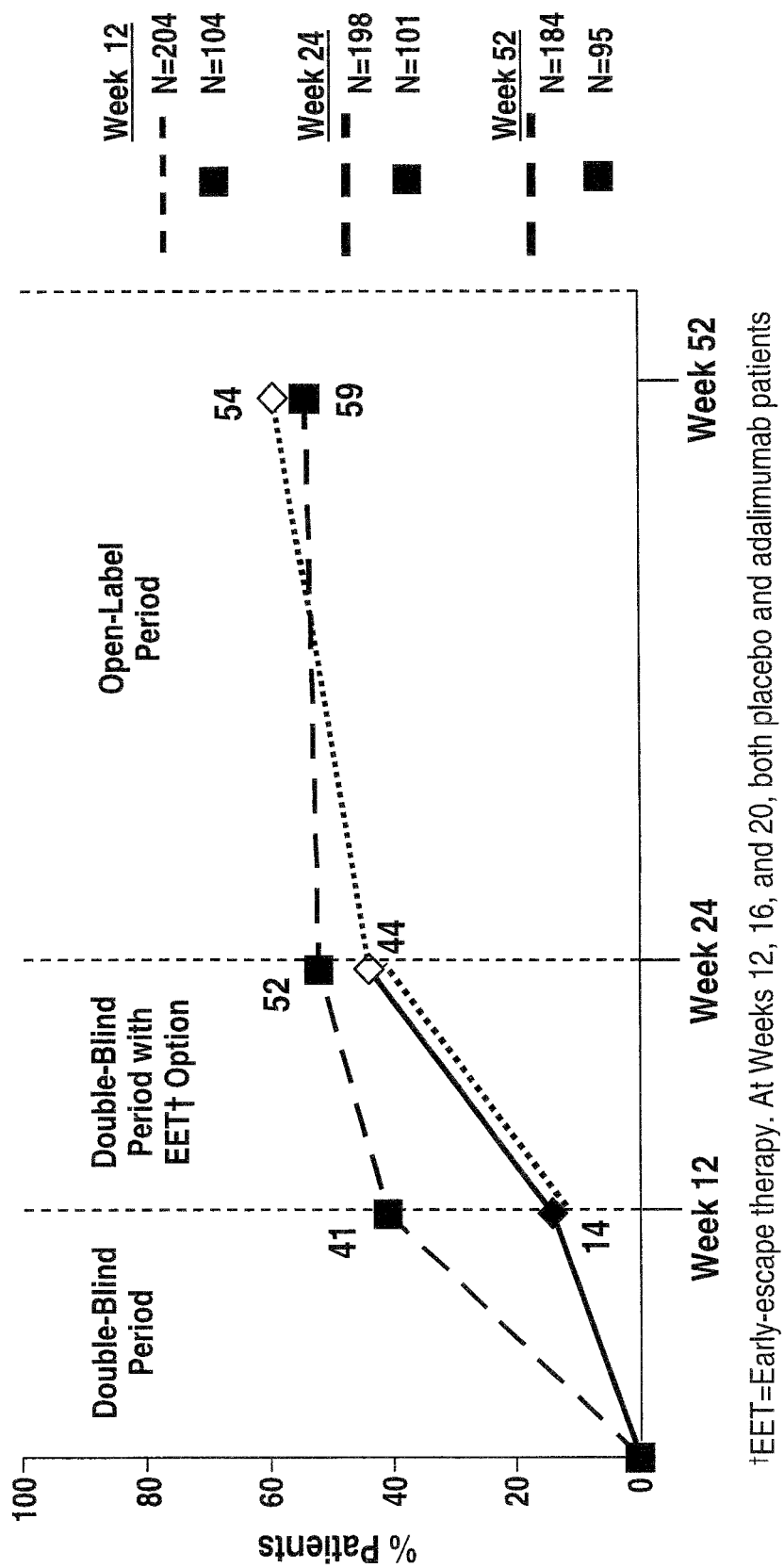
FIG. 28 graphically depicts ASAS40 Response over 52 weeks (Observed).
Figure 29:
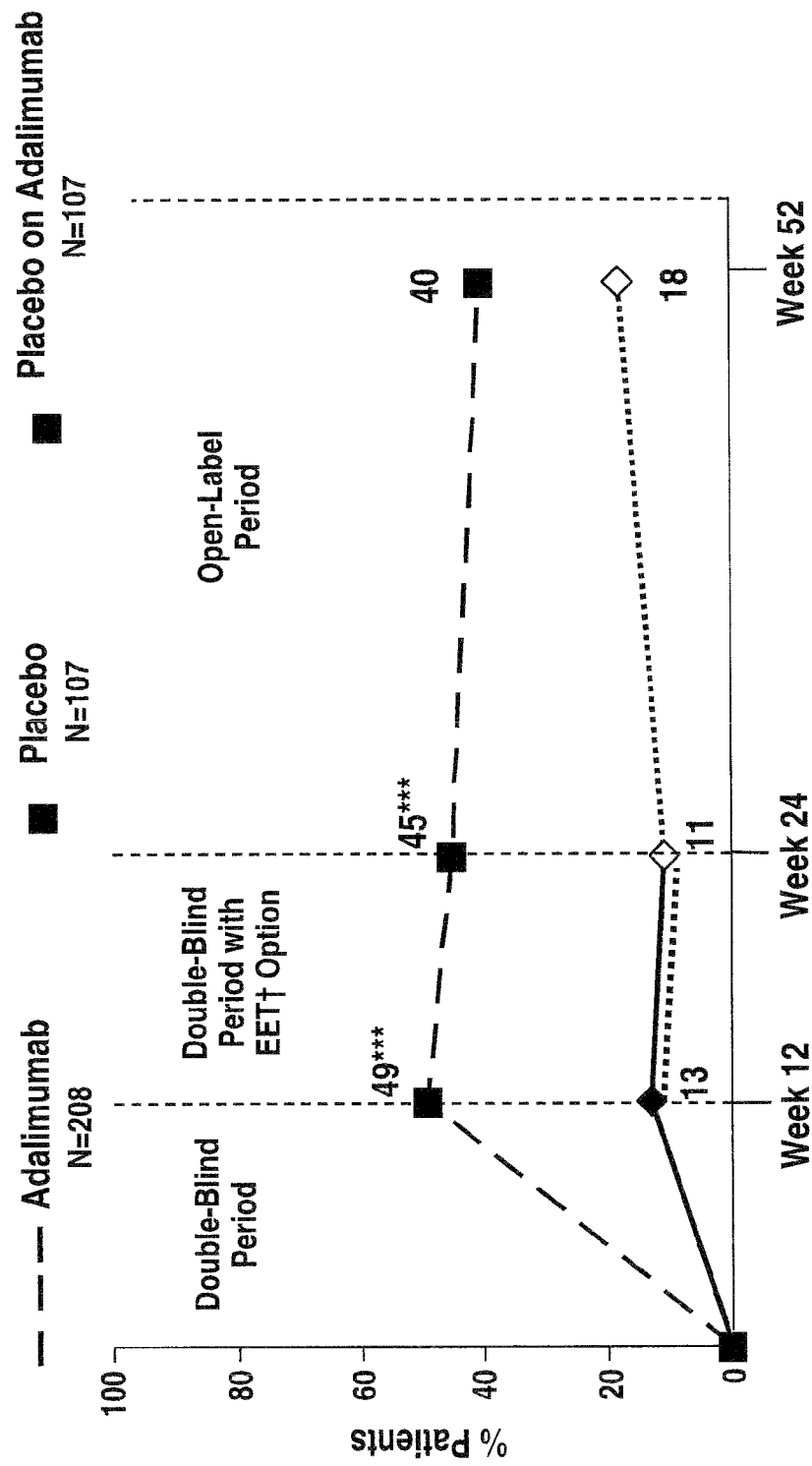
FIG. 29 graphically depicts ASAS 5/6 Response over 52 weeks (Nonresponder Imputation).
Figure 30:
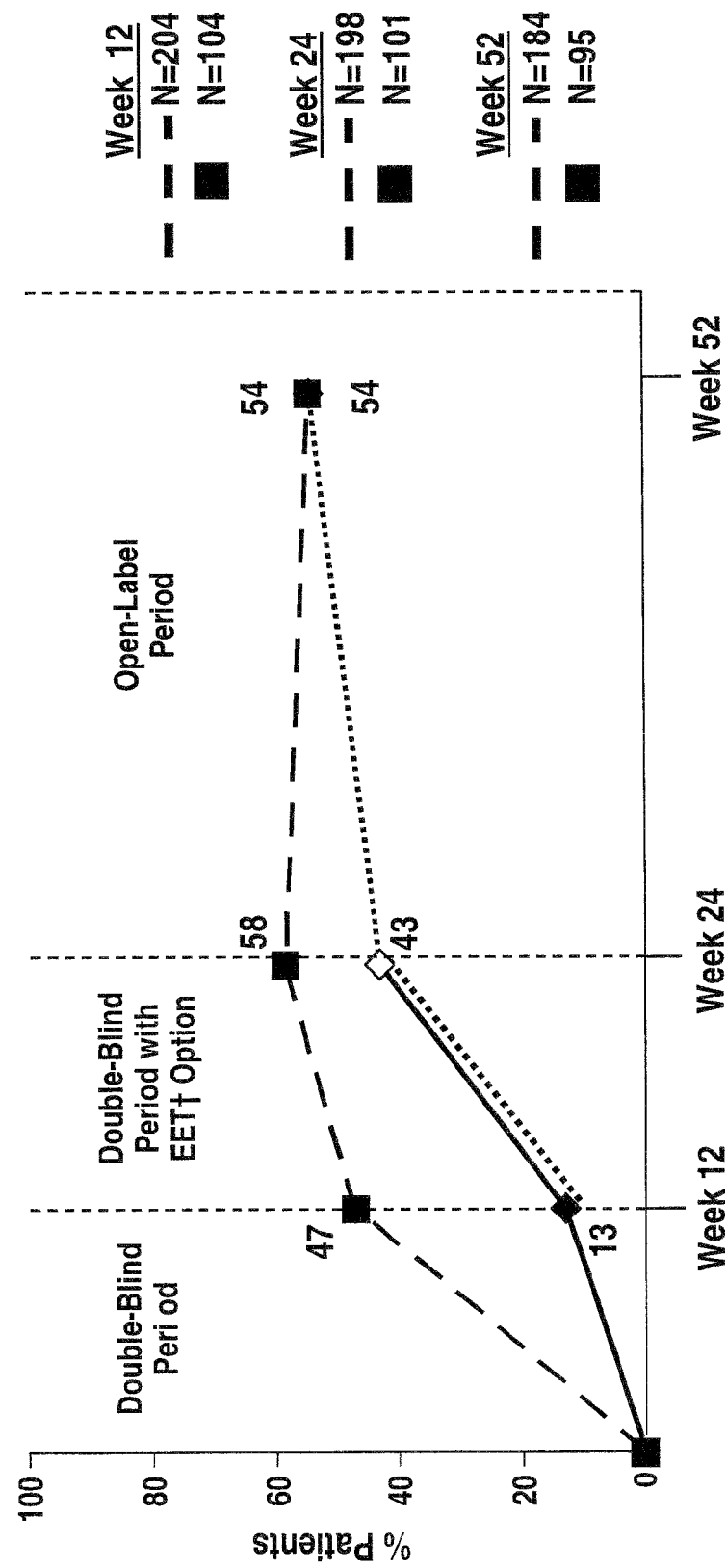
FIG. 30 graphically depicts ASAS 5/6 Response over 52 weeks (Observed).
Figure 31:
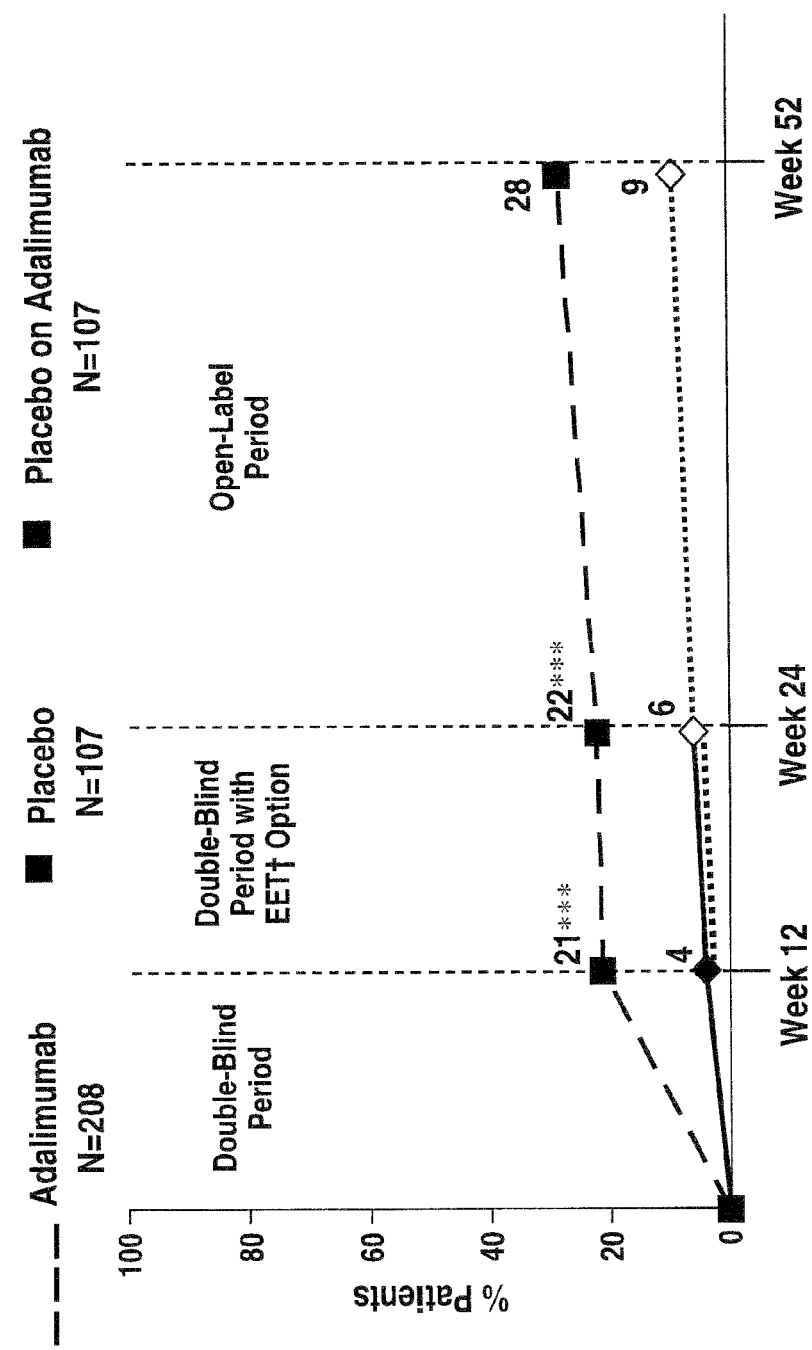
FIG. 31 graphically depicts ASAS partial remission response over 52 weeks (Nonresponder Imputation).
Figure 32:
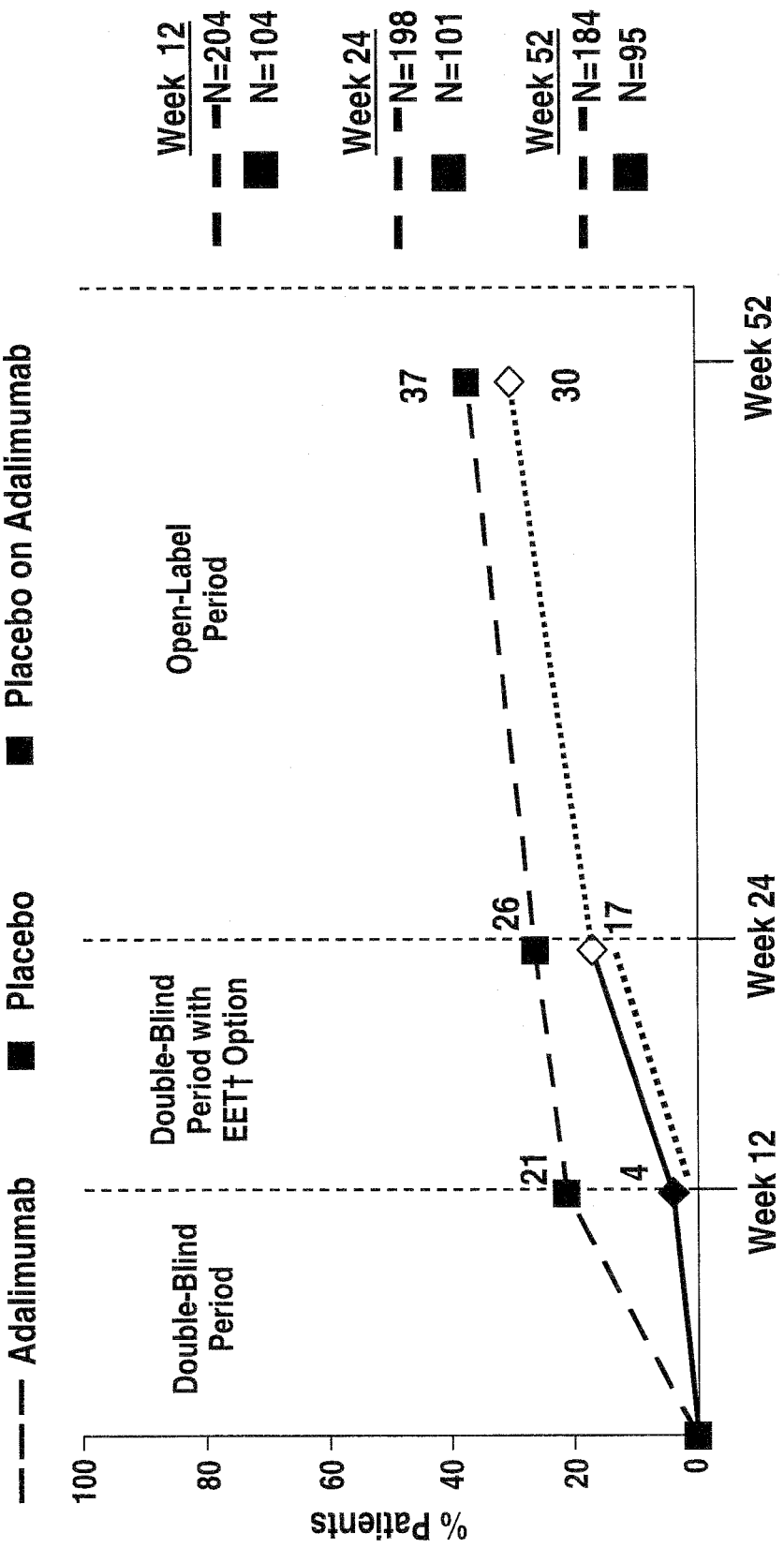
FIG. 32 graphically depicts ASAS Partial Remission Response over 52 weeks (Nonresponder Imputation).

FIG. 23 (known as tornado diagram) presents the effect on the cost per QALY at 30 years of varying key model parameters in the univariate sensitivity analyses. No single parameter dramatically affected the results, indicating that the estimates were robust. When indirect costs were included from a societal perspective, the cost effectiveness ratio decreased from £23,097 per QALY in the base case to £5,093 per QALY.

Probabilistic Sensitivity Analyses confirmed that adalimumab therapy is cost-effective relative to conventional care. When only direct costs were included from the NHS perspective, the cost effectiveness ratio was below £30,000 per QALY in 69.7% of PSA simulations. When all costs including indirect costs were included from the societal perspective, the cost effectiveness ratio was below £30,000 per QALY in 89.4% of the PSA simulations.

In conclusion, the present analysis suggests that adalimumab therapy, when used according to UK treatment guidelines, is cost-effective compared with conventional care for treating patients with active AS.

Example 10

Long-Term Adalimumab Treatment Reduces Signs and Symptoms in Ankylosing Spondylitis (AS) Patients Results from Study H Study H was a trial using adalimumab evaluating long-term efficacy and safety in AS, and was a randomized, placebo-controlled, Phase III study involving patients ≥18 years of age with AS, based on modified New York criteria, who had a inadequate response or intolerance to at least 1 NSAID and might have failed one or more DMARDs. Active AS, was as diagnosed by 2 of the 3 following symptoms: Bath AS Disease Activity Index (BASDAI) score greater than or equal to 4; Visual Analog Scale (VAS) score for total back pain greater than or equal to 4; and morning stiffness ≥1 hour.

Patients were randomized to either subcutaneous adalimumab 40 mg every other week (eow) or placebo for 24 weeks. (FIG. 1). Patients failing to achieve ASAS 20 at Week 12, 16, or 20 were allowed to switch to open-label 40 mg eow (early escape therapy). Any patient receiving EET was treated as a nonresponder at all subsequent visits in the statistical analysis ASAS20 Improvement Criteria was based on an improvement of ≥20% and ≥1 unit in at least 3 domains selected from: 1) patient global, 2) pain, 3) function, and 4) inflammation; while no worsening of ≥20% and ≥1 unit in remaining domain.

ASAS40 Improvement Criteria was based on an improvement of ≥40% and ≥2 units in at least 3 domains selected from: 1) patient global, 2) pain, 3) function, and 4) inflammation; while no worsening at all in remaining domain.

ASAS 5/6 Improvement Criteria was based on improvement of ≥20% in at least 5 domains selected from: 1) patient global, 2) pain, 3) function, 4) inflammation, 5) CRP; and spinal mobility.

ASAS Partial Remission Criteria included a value <2 units all 4 domains including: 1) patient global, 2) pain, 3) function, and 4) inflammation 315 patients enrolled in Study H. Of those 208 received adalimumab and 107 received the placebo. Of the 107 patients to receive the placebo 4 Patients discontinued by Week 12 (2 Adverse events/1 Lost to follow up/2 Other reasons) while 103 completed week 12. 101 patients completed week 24 while a total of 6 patients discontinued by week 24 (2 adverse events/1 withdrew consent/1 Lost to follow up/4 other reasons).

Of the 208 patients to be randomized into the adalimumab group, 204 Patients completed Week 12, while 4 discontinued (2 adverse events/2 withdrew consent/2 other reasons). 195 patients completed Week 24, while 13 patients total discontinued (5 adverse events/5 withdrew consent/2 other reasons/1 lost to follow up). In total 277 patients, between the placebo and adalimumab group completed week 52.

Overall both groups had similar characteristics. See Table 44 for more baseline demographics. See Table 45 for baseline disease values across the two treatment groups. See Table 46 for information regarding patients opting for early escape therapy.

TABLE 44

<table>
<tr><th colspan="3">Baseline Demographics</th></tr>
<tr><th></th><th>Placebo<br>(N = 107)<br>n (%)</th><th>Adalimumab<br>40 mg eow<br>(N = 208)<br>n (%)</th></tr>
<tr><td>Mean age (years)</td><td>43.4</td><td>41.7</td></tr>
<tr><td>Sex (males)</td><td>79 (73.8)</td><td>157 (75.5)</td></tr>
<tr><td>Race (Whites)*</td><td>99 (92.5)</td><td>202 (97.1)</td></tr>
<tr><td>HLA-B27 positive</td><td>85 (79.4)</td><td>163 (78.4)</td></tr>
<tr><td>Mean duration of AS (years)</td><td>10.0</td><td>11.3</td></tr>
<tr><td>History of inflammatory bowel disease†</td><td>6 (5.6)</td><td>21 (10.1)</td></tr>
<tr><td>Peripheral arthritis‡</td><td>44 (44.1)</td><td>75 (36.1)</td></tr>
<tr><td>History of psoriasis*†</td><td>17 (15.9)</td><td>16 (7.7)</td></tr>
<tr><td>History of uveitis†</td><td>27 (25.2)</td><td>68 (32.7)</td></tr>
</table>

*No significant differences between groups except for race and psoriasis
†Stable for at least four weeks prior to Baseline
‡At least one SJC at Baseline

TABLE 45

Baseline Disease Activity

| | | Placebo (N = 107) | Adalimumab 40 mg eow (N = 208) |
|---|---|---|---|
| BASDAI score† | | 6.3 | 6.3 |
| BASDAI categories‡ | <4 | 12 (11.2) | 25 (12.0) |
| | 4-6 | 30 (28.0) | 62 (29.8) |
| | >6 | 65 (60.7) | 121 (58.2) |
| Total Back Pain VAS† | | 6.7 | 6.4 |
| Morning Stiffness†,§ | | 6.7 | 6.7 |
| BASFI† | | 5.6 | 5.2 |
| CRP (mg/dL)† | | 2.2 | 1.8 |
| Patients with elevated CRP‡** | | 75 (70.1) | 138 (66.3) |

*No significant differences between groups in all parameters
†Mean
‡n (%)
§Mean of BASDAI questions 5 and 6
**Normal CRP range: 0.07-0.494 mg/dl

TABLE 46

Patients Receiving Early-escape Open-label Therapy

| Visit | Placebo (N = 107) n (%) | Adalimumab 40 mg eow (N = 208) n (%) |
|---|---|---|
| Total | 74 (69.2) | 81 (38.9) |
| Week 12 | 55 (51.4) | 54 (26.0) |
| Week 14 | 11 (10.3) | 5 (2.4) |
| Week 16 | 6 (5.6) | 10 (4.8) |
| Week 18 | 0 (0.0) | 1 (0.5) |
| Week 20 | 2 (1.9) | 8 (3.8) |
| Week 22 | 0 (0.0) | 3 (1.4) |

Figure 33:
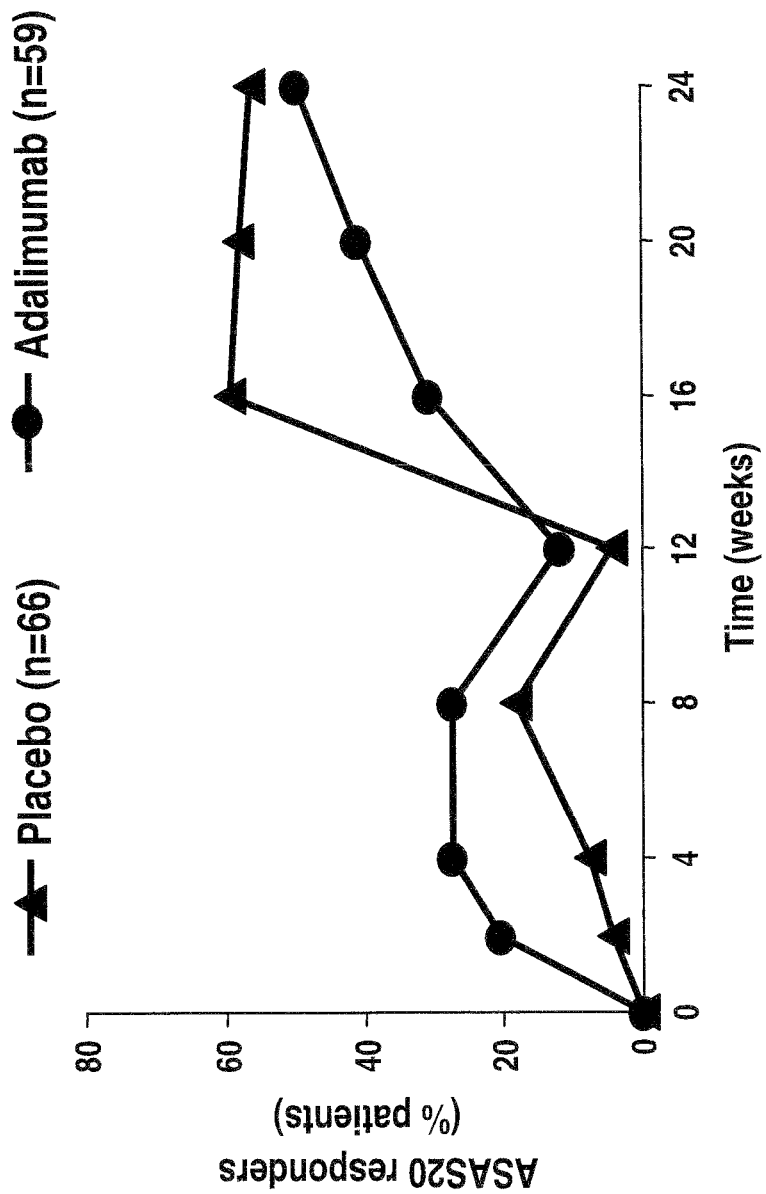
FIG. 33 shows a summary of ASAS20 response for those patients who switched to EEOL at week 12 and week 14.

FIGS. 24-32 demonstrate the efficacy of adalimumab as measured by ASAS 20, 40, & 5/6 over a period of 52 weeks. All figures show a higher percentage of patients reporting ASAS value while on adalimumab than those patients treated with placebo. FIG. 33 shows the percentage of patients reporting ASAS 20 values before and after beginning early escape therapy.

Adalimumab was safe as well as efficacious. 87.9% of patients were still enrolled in the trial at Week 52. Through Week 24, no patients on adalimumab developed serious infections; from Week 24 to Week 52, one patient on adalimumab developed a serious infection (appendicitis). Through Week 52, one patient on adalimumab developed Non-Hodgkin's lymphoma. There were no cases of tuberculosis, lupus-like reactions, demyelinating disease, congestive heart failure, or death through Week 52. Table 47 shows adverse events, nasopharyngitis, injection site reactions, and headache to have occurred at greater than 5% through week 24.

Through Week 24, significantly more adalimumab patients had elevated liver enzymes and total bilirubin compare with placebo, but the changes were small; from Week 24 to Week 52, there were no clinically meaningful elevations in these parameters. No patient had clinically meaningful trends in other laboratory values from Week 24 to Week 52

TABLE 47

Adverse Events ≥5% Through Week 24 - Follow-up Through Week 52†

| | Day 1-168 | | Day 169-364 |
|---|---|---|---|
| MedDRA preferred term: | Placebo (N = 107) n (%) | Adalimumab 40 mg eow (N = 208) n (%) | Open-Label Adalimumab (N = 255) n (%) |
| Nasopharyngitis | 8 (7.5) | 26 (12.5) | 15 (6.8) |
| Injection site reaction | 3 (2.8) | 22 (10.6)* | 3 (1.2) |
| Headache | 9 (8.4) | 20 (9.6) | 5 (2.2) |

Of all treatment-emergent AEs with a start data on or after the first dose of adalimumab through Feb. 28, 2005. If patient drops out, AEs are counted up to 70 days after the last dose of study medication or less up to Feb. 28, 2005. If a patient had more than one event of the same MedDRA term, only the first occurrence was included.
†During administration of blinded study medication.
*Statistically significant at p ≤ 0.05 level.

In conclusion, Adalimumab demonstrated a significant ability to reduce signs and symptoms in AS patients at Week 12; this efficacy was sustained for up to 52 weeks of treatment. Adalimumab is generally well-tolerated in patients with active AS. The safety profile of adalimumab is consistent with that observed in RA and PsA trials

Example 11

Translation and Validation of New Language Versions of the Anklyosing Spondylitis Quality of Life (ASQoL) Questionnaire The Ankylosing Spondylitis Quality of Life (ASQoL) questionnaire is a unidimensional, disease-specific measure of needs-based QoL developed in the UK and the Netherlands. This study describes the adaptation of the scale into several additional country languages.

The ASQoL was translated into US-English, Canadian-French and English, French, German, Italian, Spanish and Swedish by dual-panel methods. Cognitive debriefing interviews were conducted with AS patients. Psychometric/scaling properties were assessed using blinded data from two randomized, double-blind, Phase III studies of adalimumab. Baseline and Week-2 data assessed test-retest reliability. Validity was determined by correlation of ASQoL with SF-36 and with Bath AS Functional Index (BASFI) and by discriminative ability of ASQoL based on disease severity. Item response theory (Rasch model) tested the ASQoL's scaling properties.

Cognitive debriefing showed the new language versions of ASQoL to be clear, relevant and comprehensive. Clinical study sample sizes varied by country. They were sufficient for psychometric/scaling assessment in US-English (n=148; 75% M; mean age 44.7/SD: 12.5) and Canadian-English (n=66; 77.3% M; mean age 39.8/SD: 10.5), sufficient for psychometric but not scaling analyses for German (n=37; 70.3% M; mean age 41.9/SD: 11.8) and sufficient for preliminary evidence of these properties for the remaining languages. Test-retest reliability and Cronbach's alpha coefficients were high: US-English (0.85, 0.85), Canadian-English (0.87, 0.86), and German (0.77, 0.79). Correlations of ASQoL with SF-36 and with BASFI in these three languages were moderate. US-English, Canadian-English, and German measures were able to discriminate between patients based on their perceived disease severity (p<0.01). Comparable results were obtained for the additional languages. US-English and Canadian-English exhibited fit to the Rasch model as indicated by non-significant $\chi^2$ p-values (US=0.54, Canadian-English=0.68), confirming unidimensionality.

In conclusion, the ASQoL was successfully translated into all languages and was subsequently acceptable to local patients. Psychometric properties are excellent for US-English, Canadian-English, and German and extremely promising for other languages.

Example 12

Adalimumab Improves Patient Acceptable Symptom State (PASS) in Ankylosing Spondylitis (AS)

Patient reported outcomes (PRO), such as pain and function, are considered key elements in the evaluation of anti-rheumatic therapies. Most outcome measures are continuous and results are reported in terms of mean change, e.g., BASDAI and BASFI scores.

Patient Acceptable Symptom State (PASS) is a new method for assessing whether the patient (pt) considers his/her overall disease state satisfactory, and provides a method which considers the individual patient response. The PASS concept requires only that the clinician asks the patient a single question requiring a yes or no answer: "Considering all the different ways your disease is affecting you, if you would stay in this state for the next months, do you consider that your current state is satisfactory?" Achievement of PASS indicates that a patient feels well, and assessment of PASS, therefore, is a simple measure to determine whether a patient has achieved therapeutic success, including in a clinical trial or in clinical practice. Use of the PASS concept in addition to other patient-reported outcome measures has been described in a few chronic rheumatic conditions (Tubach et al. Ann Rheum Dis 2005; 64:29-33; Dougados et al. Arthritis Res Ther 2007; 9:R11) and acute pain conditions (Tubach et al. Arthritis Rheum 2006; 55:526-30; Dougados et al. PLoS Clin Trials 2007; 2:e9).

The purpose of this study was to provide clinical relevance of AS treatment at an individual patient level, as it is important to assess whether the patient considers his/her current disease state satisfactory (referred to as the Patient Acceptable Symptom State or PASS). This study evaluated the treatment effect of adalimumab in improving AS patients to PASS. The study also applied data from Study H to evaluate the feasibility, validity, reliability, and discriminant capacity of PASS to AS patients.

The study design of Study H (phase III study) is shown in FIG. 1. At baseline, both arms (ADA n=208, PBO n=107) had comparable demographic/disease characteristics. Inclusion criteria is described Example 10 above, and baseline demographics are described above in Table 44. Baseline disease activity is described above in Table 45. Concomitant treatment at baseline of Study H is shown below in Table 48.

TABLE 48

| Concomitant Treatment at Baseline (%) | | |
|---|---|---|
| | Placebo (N = 107) | Adalimumab 40 mg eow (N = 208) |
| Baseline DMARD use | 22 (20.6) | 40 (19.2) |
| Methotrexate | 8 (7.5) | 20 (9.6) |
| Sulfasalazine | 15 (14.0) | 26 (12.5) |
| Leflunomide | 1 (0.9) | 0 |
| Hydroxychloroquine | 3 (2.8) | 0 |

TABLE 48-continued

| Concomitant Treatment at Baseline (%) | | |
|---|---|---|
| | Placebo (N = 107) | Adalimumab 40 mg eow (N = 208) |
| Oral corticosteroids | 6 (5.6) | 25 (12.0) |
| NSAIDs | 84 (78.5) | 166 (79.8) |

Patients (pts) with active AS and an inadequate response to at least one NSAID were randomized to either adalimumab (ADA) 40 mg every other week or placebo (PBO) for 24 weeks. After the Week 12 assessment, pts not achieving an ASAS20 response were eligible for early escape therapy (EET) with ADA. All EET pts were treated as PASS nonresponders at all subsequent visits.

The percentage of patients who were ASAS20 responders at Week 12 was the primary efficacy endpoint for Study H. Major secondary endpoints included ASAS20 at week 24; ASAS50; ASAS70; ASAS20 components (including total back pain, BASFI score, inflammation, and Patient's Global Assessment of Disease Activity); BASDAI; BASDAI 20; BASDAI 50; BASDAI 70; BASMI; MASES; and CRP.

An ASAS20 responder was defined as achieving improvement of at least 20% and absolute improvement of at last 1 unit as compared with baseline in at least 3 of the 4 following domains, with no deterioration (defined as a worsening of at least 20% or an absolute increase of at least 1 unit) in the remaining domains (Anderson et al. Arthritis Rheum 2001; 44:1876-86): patient's global assessment of disease activity based on a 0-10-cm VAS, patient's assessment of pain based on a 0-10-cm VAS for total back pain, function according to the BASFI score assessed with a 0-10-cm VAS (Calin et al. J Rheumatol 1994; 21:2281-5), and inflammation based on the mean of the severity and duration of morning stiffness (i.e., questions 5 and 6 of the BASDAI (Garrett et al. J Rheumatol 1994; 21:2286-91) as measured by a 0-10-cm VAS. An ASAS40 response was defined as at least 40% improvement and 2 units of absolute change in 3 of the 4 domains of the ASAS20 criteria, with no worsening in the fourth domain. An ASAS 5/6 response was defined as 20% improvement in 5 of 6 domains, consisting of the 4 domains of the ASAS20 criteria plus spinal mobility (as measured by the Bath AS Metrology Index [BASMI] (Jenkinson et al. J Rheumatol 1994; 21:1694-8) and acute-phase reactants (C-reactive protein [CRP]). An ASAS partial-remission response was defined as a value of <2 on a 0-10-point scale in each of the 4 ASAS20 domains (van der Heijde et al. Arthritis Rheum 2005; 52:386-94). A BASDAI50 response was defined as at least 50% improvement in the BASDAI score as compared with baseline. Additional efficacy evaluations included the Short Form-36 Health Survey Physical Component Summary (SF-36 PCS) (Kosinski et al. Med Care 1999; 37(5 Suppl):MS10-22) and the AS Quality of Life (ASQoL) questionnaire (Helliwell et al. Arthritis Rheum 1999; 42(suppl):S72).

The PASS was assessed with a patient-reported question with Yes/No answers for "Considering all the different ways your disease is affecting you, if you would stay in this state for the next month, do you consider that your current state is satisfactory?" at Weeks 2, 4, 8, 12, 16, 20 and 24. Survival analysis examined the time to the first yes response to the PASS question, and time to the start of sustained PASS (defined as beginning of a continuous sequence with at least both Week 20 and Week 24 in PASS). Log-rank tests assessed treatment differences in time to response.

Statistical Analyses and Evaluation of Metrologic Properties of PASS

Evaluation of efficacy analyses and metrologic properties of PASS were based on an intention-to-treat analysis that included all patients who received at least 1 injection of study medication; no patients were excluded from data analyses. Patients who switched to the early escape, open-label treatment option at Week 12 and patients with missing PASS responses were categorized as having answered no to PASS at all subsequent clinic visits.

The feasibility of using PASS to assess patients with active AS in a clinical trial was assessed by the patients' acceptability to answer the question. Specifically, feasibility/acceptability was assessed by determining the response rate (i.e., the overall percentage of patients who responded either yes or no to the question) at each clinic visit.

The test-retest reliability of PASS was determined in patients who were clinically stable (defined as a change in the BASDAI of <1 unit on a 0-10-unit scale) by correlating Week-8 and Week-12 responses to the PASS question using the kappa coefficient. The kappa coefficient was calculated as the ratio of the observed excess over chance agreement to the maximum possible excess over chance agreement; values of 1 indicate perfect agreement and values of 0 indicate that observed agreement between measures is equal to chance alone. The strength of agreement between 2 responses based on kappa coefficient values of 0.21 to 0.4 is considered fair, 0.41 to 0.6 is moderate, 0.61 to 0.80 is substantial, and 0.81 to 1.0 is perfect. The correlation between Week-8 and Week-12 PASS responses was chosen because these 2 visits occurred during the double-blind period (i.e., before patients could switch to early escape, open-label treatment after Week 12, 16, or 20 visits), thus minimizing the likelihood of a subjective response while receiving open-label treatment.

The external validity of PASS for use in patients with AS was evaluated by comparing the relationship of PASS responses (yes vs no) to the change from baseline in the following clinical efficacy and patient-reported outcomes measures at Week 12: BASDAI, BASFI, CRP concentration, BASMI, SF-36 PCS, and the ASQoL questionnaire. For each of these assessments, the mean changes at Week 12 for the PASS yes and PASS no groups were compared using a Student t test. Also, the percentage of patients who were BASDAI50 responders at Week 12 were compared between those who answered yes to PASS and those who answered no to PASS using the chi-square test. Similar tests were performed for ASAS20, ASAS40, and ASAS partial remission responders at Week 12.

The discriminant capacity is the capacity to demonstrate a difference between groups in the outcome measure after effective therapy in comparison with no treatment. The discriminant capacity of PASS over time was assessed by comparing the percentage of patients in the active (adalimumab) group to the percentage of patients in the inactive (placebo) group who achieved PASS at each clinic visit using the chi-square test. To evaluate the clinical relevance of this psychometric property, the discriminant capacity of PASS in active verus placebo treatment groups at Week 12 were compared with conventional measures of clinical response at Week 12, specifically, the ASAS20, ASAS40, ASAS 5/6, ASAS partial remission, and BASDAI50 response criteria, using the chi-square test.

The time to the first achievement of PASS (defined as a yes response to the question) and the time to the start of sustained PASS (defined as the beginning of a continuous sequence with at least Weeks 20 and 24 in PASS) were analyzed using Kaplan-Meier survival methods. Log-rank tests were used to compare the differences in the Kaplan-Meier estimates of time to first PASS and time to sustained PASS between adalimumab and placebo treatment groups.

Results

As described in Example 10, adalimumab was effective at improving the ASAS response in patients with AS. ASAS improvements in the adalimumab patient population vs. placebo are described in Table 49 below.

TABLE 49

| | | ASAS 20/50/70 (imputed*) | | | |
|---|---|---|---|---|---|
| | | Week 12 | | Week 24 | |
| | | Adalimumab (n = 208) | Placebo (n = 107) | Adalimumab (n = 208) | Placebo (n = 107) |
| % of patients | ASAS20 | 58.2*** | 20.6 | 50.5*** | 18.7 |
| | ASAS50 | 38.0*** | 10.3 | 35.1*** | 11.2 |
| | ASAS70 | 23.1*** | 4.7 | 24.0*** | 8.4 |

*Patients who received early escape therapy or discontinued are counted as non-responders at Weeks 12 and 24

In addition, patients with missing data at Week 12 or 24 also are counted as non-responders at the respective visit

***Statistically significant at p = 0.001 level (Pearson's Chi-Square test)

The response rate to the PASS question exceeded 98% at all scheduled visits (Week 2 through Week 24), demonstrating the feasibility/acceptability of applying the PASS concept in patients with AS.

The test-retest reliability of PASS in patients with AS was very high (kappa coefficient=0.86). Of 202 patients with a stable BASDAI between Week-8 and Week-12 clinic visits, only 14 patients had discordant answers to the PASS question at the 2 visits (Table 50).

TABLE 50

| Correlation of PASS responses (yes vs no) for patients with stable disease between Week 8 and Week 12* | | |
|---|---|---|
| PASS response | Yes at Week 12, N | No at Week 12, N |
| Yes at Week 8, N | 75 | 10 |
| No at Week 8, N | 4 | 113 |

*Stable disease was defined as a change of <1 unit on the Bath Ankylosing Spondylitis Disease Activity Index.

Patients responding yes versus no to the PASS question at Week 12 corresponded with statistically significant improvements in clinical, laboratory (including CRP concentration), and patient-reported outcome measures (Table 51). In addition, the percentages of patients who achieved PASS and who were ASAS20, ASAS40, or ASAS partial remission, and BASDAI50 responders were statistically significantly greater compared with the percentages of patients who did not achieve PASS(P<0.001 for all comparisons; see Table 52). These data, based on both objective and subjective measures, show that the PASS concept is valid for use in patients with AS.

TABLE 51

Relationship of PASS Responses to Clinical/PRO Measures

| Measures (Change from Baseline at Week 12) | PASS Response Status at Week 12 | | | | |
|---|---|---|---|---|---|
| | Yes | | No | | |
| | N | Mean (SD) | N | Mean (SD) | P Value |
| BASDAI | 112 | −3.5 (2.3) | 196 | −1.2 (2.2) | <0.0001 |
| BASFI | 112 | −23.5 (19.9) | 196 | −7.7 (17.6) | <0.0001 |
| SF-36 PCS | 111 | 9.1 (8.5) | 189 | 3.0 (8.0) | <0.0001 |
| ASQoL | 112 | −4.5 (4.2) | 196 | −1.3 (3.3) | <0.0001 |
| CRP (mg/dL) | 111 | −1.3 (2.4) | 191 | −0.6 (1.5) | 0.0134 |
| BASMI | 111 | −0.6 (1.3) | 196 | −0.1 (1.4) | 0.0033 |

Note:
BASDAI = BathAS Disease Activity Index; BASFI = BathAS Functional Index; SF-36 PCS = SF-36 Physical Component Summary, ASQoL = AS Quality of Life Questionnaire, CRP = C-reactive protein.

TABLE 52

External validity of PASS

| | | ASAS20 | ASAS40 | ASAS Partial remission | BASDAI 50 |
|---|---|---|---|---|---|
| % responders | PASS Yes | 75 | 61 | 37 | 65 |
| | PASS No | 29 | 16 | 3 | 19 |

Use of the PASS concept statistically differentiated adalimumab-treated patients from placebo-treated patients, demonstrating the discriminant capacity of the PASS question for use in patients with AS. At Week 2, 29.8% of the adalimumab group achieved PASS (i.e., responded yes) compared with 17.8% of the placebo group (P=0.021). The difference between the percentages of patients achieving PASS in each group was greater at Week 12 (42.3% of adalimumab-treated patients vs 22.4% of placebo-treated patients, P<0.001). At Week 24, 38.0% of adalimumab-treated patients achieved PASS compared with 13.1% of placebo-treated patients (P<0.001).

The discriminant capacity of PASS in patients with AS was demonstrated by evaluating the percentages of patients who achieved PASS in active versus placebo treatment groups compared with the percentages of patients in each group who achieved conventional definitions of clinical response criteria in AS at Week 12, including ASAS20, ASAS40, ASAS 5/6, and ASAS partial remission (Table 53). Overall, the simple PASS question was able to discriminate between treatment groups (adalimumab vs placebo) approximately as well as other more complex traditional measures, such as the ASAS20, ASAS40, ASAS 5/6, and ASAS partial remission.

TABLE 53

Percentage of patients in the active and placebo treatment groups who achieved PASS and conventional measures of clinical response at Week 12

| Clinical response measure | Patients (%) achieving response criterion | | | |
|---|---|---|---|---|
| | Placebo (N = 107) | Adalimumab (N = 208) | $\chi^2$ value | P value* |
| PASS† | 22.4 | 42.3 | 12.18 | <0.001 |
| ASAS20‡ | 20.6 | 58.2 | 26.59 | <0.001 |
| ASAS40§ | 13.1 | 39.9 | 23.5 | <0.001 |
| ASAS 5/6‖ | 13.1 | 48.6 | 38.36 | <0.001 |
| ASAS partial remission¶ | 3.7 | 20.7 | 15.96 | <0.001 |
| BASDAI50# | 15.9 | 45.2 | 40.32 | <0.001 |

*P values were based on chi-square tests.
ASAS = ASsessment in Ankylosing Spondylitis International Working Group criteria; BASDAI = Bath Ankylosing Spondylitis Disease Activity Index; PASS = Patient Acceptable Symptom State.
†Achievement of PASS defined as a yes response to the question "Considering all the different ways your disease is affecting you, if you would stay in this state for the next months, do you consider that your current state is satisfactory?"
‡An ASAS20 response defined as improvement of at least 20% and absolute improvement of at least 1 unit as compared with baseline in at least 3 of the following 4 domains, with no deterioration (defined as a worsening of at least 20% or an absolute increase of at least 1 unit) in the remaining domain: patient's global assessment of disease activity based on a 0-10-cm visual analog scale (VAS), patient's assessment of pain based on a 0-10-cm VAS for total back pain, function according to the Bath Ankylosing Spondylitis Functional Index (BASFI) score assessed with a 0-10-cm VAS, and inflammation based on the mean of the severity and duration of morning stiffness (ie, questions 5 and 6 of the BASDAI) as measured by a 0-10-cm VAS.
§An ASAS40 response defined as at least 40% improvement and 2 units of absolute change in 3 of the 4 domains of the ASAS20 criteria, with no worsening in the fourth domain.
‖An ASAS 5/6 response defined as 20% improvement in 5 of 6 domains, consisting of the 4 domains of the ASAS20 criteria plus spinal mobility (as measured by BASMI) and acute-phase reactants (C-reactive protein).
¶An ASAS partial remission response defined as a value of <2 on a 0-10 scale in each of the 4 ASAS20 domains.

Figure 34:
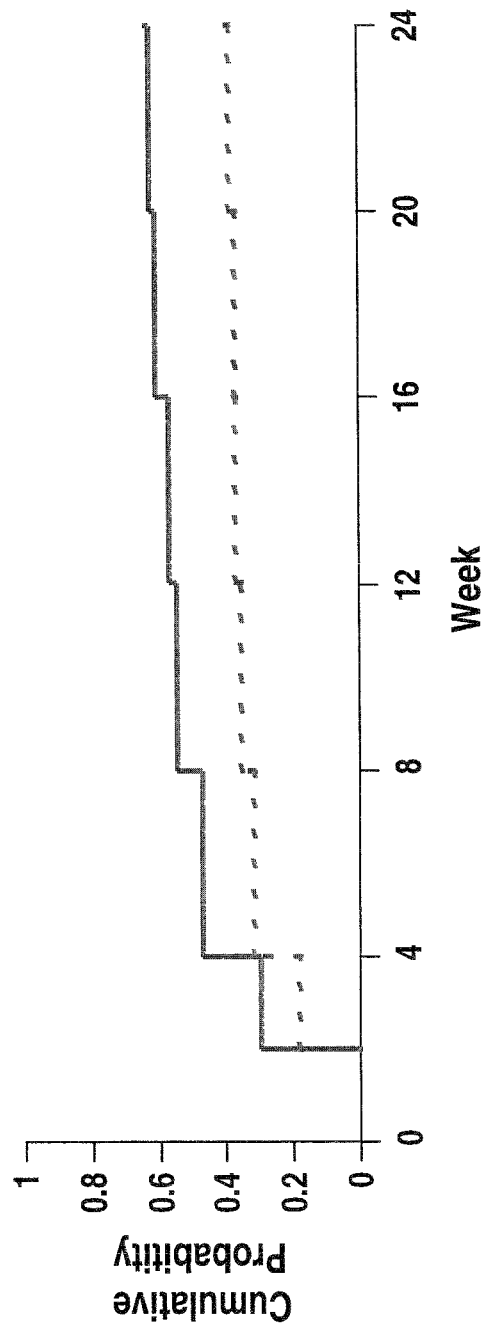
FIG. 34 shows the Kaplan-Meier Estimates of Time to First PASS.

Achievement of the first PASS occurred significantly more rapidly in adalimumab-treated patients compared with placebo-treated patients (P<0.001) as illustrated using the Kaplan-Meier survival curve. The Kaplan-Meier estimate of the time for 50% of patients to initially achieve PASS was 8 weeks for patients receiving adalimumab versus more than 24 weeks for patients receiving placebo. At Week 12, the Kaplan-Meier estimate of the percentage of patients who achieved first PASS was 56.7% (95% confidence interval [CI], 50.1-63.5%) for adalimumab-treated patients compared with 36.9% (95% CI, 28.5-46.8%) for placebo-treated patients (P=0.001). At Week 24, the Kaplan-Meier estimate of the percentage of the adalimumab group achieving first PASS increased to 63.7% (95% CI, 57.2-70.3%) compared with the placebo group estimate of 38.9% (95% CI, 30.3-48.9%; P<0.001). More adalimumab-treated patients achieved sustained PASS by Week 20 compared with placebo-treated patients (34.6% [95% CI, 28.5-41.6%] vs 12.3% [95% CI, 7.4-20.3%]; P<0.001). FIG. 34 shows time to first PASS. ADA pts took less time to reach their first PASS than PBO pts (Log-rank test p<0.001). More ADA pts achieved sustained PASS through Wk 24 than PBO pts (34.6% vs. 12.3%, Log-rank test p<0.001).

Overall, after Week 2, more ADA pts reported being in PASS than PBO pts (29.8% vs. 17.8%, p=0.021). The difference in the proportion of ADA vs. PBO pts achieving PASS was increased at Wk 12 (42.3% vs. 22.4%, p<0.001) and maintained to Week 24 (38.0% vs. 13.1%, p<0.001).

This study indicated that the PASS question provides a feasible, reliable, and valid evaluation reflecting a patient's assessment of achieving a satisfactory health state during treatment for AS. The excellent discriminant capacity of PASS was demonstrated by the differentiation between patients' response to active medication versus placebo as early as Week 2. Adalimumab-treated patients rapidly achieved PASS and maintained this state through at least 24 weeks of treatment. Application of PASS provides a clinically relevant interpretation of various outcome measures typically used to assess patients with AS.

The simplicity of the PASS question undoubtedly contributes to the feasibility and patient acceptability of this instrument. Asking and receiving a response to only 1 question requires less than 1 minute of the clinician's time, which would facilitate use of the PASS concept in clinical practice. The feasibility/acceptability and simplicity of the PASS concept also makes it a useful tool in clinical studies of patients with AS.

The PASS concept has strong face validity because it allows patients to directly assess the acceptability of their disease state. The above study demonstrates external validity using 2 methods. First, the relationship between achievement of PASS and the mean change from baseline in continuous variables was determined, including variables that are valid measures of the change in signs and symptoms of AS and also patient-reported outcome variables. The improvements in clinical signs and symptoms and patient-reported outcomes for patients who achieved PASS were statistically significantly greater than for patients who did not achieve PASS for all measures. Second, the correlation of PASS responses with several stringent AS response criteria was analyzed; a statistically significantly greater percentage of patients who achieved PASS were also ASAS40, ASAS partial remission, and BASDAI50 responders compared with patients who did not achieve PASS.

The clinical relevance of the discriminant capacity of PASS was evaluated by comparing it to the discriminant capacity of conventional response measures. The simple PASS question was able to discriminate between the adalimumab- and placebo-treated patients within the range demonstrated for other more complex measures of clinical response, including ASAS20, ASAS40, ASAS 5/6, ASAS partial remission, and BASDAI50 response. The PASS concept is unique because it offers a simple patient-reported assessment of overall well-being, unlike the ASAS and BASDAI response measures that may have multiple questions or domains for score calculations.

This study indicated that adalimumab rapidly and significantly improved AS patients to the PASS and maintained PASS through at least 24 wks of treatment. Applying the PASS results in clinical studies may provide clinical relevant interpretation for outcomes measures. Furthermore, this study indicated that the PASS question evaluates a valid and reliable concept reflecting the patient's assessment of achieving a satisfactory health state in AS. PASS also demonstrated good discriminant capacity in separating the superior response of adalimumab treatment from placebo in treating AS patients.

Example 13

Treatment with Adalimumab Reduces Signs and Symptoms and Induces Partial Remission in Patients with Ankylosing Spondylitis (AS)

1-Year Results from Study

This study examined long-term efficacy and safety in AS in patients using adalimumab. The study was a randomized, placebo (PBO)-controlled, double-blind, Phase III study, and assessed the ability of the anti-TNF agent adalimumab to reduce signs and symptoms and induce partial remission over 52 weeks.

Patients (pts) with active AS who had an inadequate response to at least one NSAID were eligible for enrollment. Randomized pts received either double-blind adalimumab (ADA) 40 mg every other week (eow) or PBO for 24 weeks (wks). At Wk 24, all pts were switched to open label ADA 40 mg eow for an additional 28 wks. Efficacy was evaluated in signs and symptoms by ASsessment in AS (ASAS) 20 International Working Group Criteria (Inflammation, Total Back Pain, Function, and Patient's Global Assessment of disease activity) and by ASAS partial remission criteria (value of <20 on a 0-100 scale in all 4 ASAS20 domains). The primary endpoint was ASAS20 at Wk 12. Starting at Wk 12, pts were eligible for early-escape therapy (EET) of open-label ADA 40 mg eow. Three analyses to evaluate the 1-year efficacy of ADA were conducted: 1) a non-responder imputation to Wk 52 (EET pts and dropouts were considered as non-responders), 2) observed data for all pts from Baseline, and 3) observed data for EET pts only.

During the first 12 wks, ADA pts showed a reduction in signs and symptoms and achieved partial remission, which was sustained through 52 wks of treatment (see Tables 54 and 55 below). The numbers of PBO pts who switched to EET were: 66 at Week 12, 7 at Week 16, and 2 at Week 20. By Week 52, 88.6% of all pts remained in the study.

TABLE 54

ASAS20 Response for Study H

| | Week 12 N/Total (%) | Week 24 N/Total (%) | Week 52[‡] N/Total (%) |
|---|---|---|---|
| Non-responder imputation | | | |
| Placebo (N = 107) | 22/107 (20.6) | 19/107 (17.8) | 22/107 (20.6) |
| Adalimumab (N = 208) | 121/208 (58.2) | 105/208 (50.5) | 96/208 (46.6) |
| Observed Data for all patients | | | |
| Placebo (N = 107) | 22/104 (21.2) | 63/101 (62.4)[†] | 71/95 (74.7) |
| Adalimumab (N = 208) | 121/204 (59.3) | 148/198 (74.7) | 136/184 (73.9) |
| Observed Data for EET patients | | | |
| Placebo (N = 75) | 5/75 (6.7) | 44/73 (60.3) | 49/68 (72.1) |

TABLE 37

Partial Remission Response for Study H

| | Week 12 N/Total (%) | Week 24 N/Total (%) | Week 52[‡] N/Total (%) |
|---|---|---|---|
| Non-responder imputation | | | |
| Placebo (N = 107) | 4/107 (3.7) | 6/107 (5.6) | 10/107 (9.3) |
| Adalimumab (N = 208) | 43/208 (20.7) | 46/208 (22.1) | 58/208 (27.9) |
| Observed Data for all patients | | | |
| Placebo (N = 107) | 4/104 (3.8) | 17/102 (16.7)[†] | 28/95 (29.5) |
| Adalimumab (N = 208) | 43/204 (21.1) | 52/198 (26.3) | 68/184 (37.0) |
| Observed Data for EET patients | | | |
| Placebo (N = 75) | 0/75 (0) | 11/74 (14.9) | 18/68 (26.5) |

[†]Includes EET pts: 26 pts were on PBO and 75 pts on ADA at Week 24.
[‡]All pts were on unblinded ADA at Week 52.

In conclusion, adalimumab was efficacious in reducing signs and symptoms and inducing partial remission in AS patients at Week 12. Efficacy was sustained for up to 52 weeks of treatment and patients switching from placebo to adalimumab experienced similar efficacy.

Example 14

Adalimumab Improves Physical Functioning and Work Productivity in Ankylosing Spondylitis (AS) Patients Ankylosing spondylitis (AS) is a chronic, progressive, inflammatory disease primarily affecting the axial skeleton, peripheral joints, and entheses, which results in functional limitation and impairment in quality of life. Pain, fatigue, and progression of AS can lead to work disability, entailing substantial absence from paid work and decrease in productivity (Boonen et al. Ann Rheum Dis. 2002; 61:429-437). Adalimumab is a fully human monoclonal antibody targeting TNF that has been shown to reduce the signs and symptoms of AS and improve quality of life in AS patients (see van der Heijde, et al. Arthritis Rheum. 2006; 54:2136-46 and van der Heijde et al. Arthritis Rheum. 2005; 52(9)(Suppl):S211).

Ankylosing spondylitis (AS) could significantly impact a patient's physical functioning, leading to limitations in one's ability to work. The following analysis evaluated the treatment effect of adalimumab on physical functioning (PF) and work productivity (WP) in AS patients with active disease.

Patients from the Adalimumab Trial evaluating Long-term efficacy and safety in AS study, a Phase III study involving patients with active AS who had an inadequate response to at least one NSAID, were randomized to either adalimumab 40 mg every other week or placebo (PBO) for 24 weeks. The study design is shown in FIG. 1. At Week 12, patients not achieving an ASAS20 response (a 20% response according to the ASsessment in Ankylosing Spondylitis International Working Group criteria for improvement) at Weeks 12, 16, or 20 were eligible to receive early-escape open-label treatment (EET) with adalimumab 40 mg eow Functionality Measures PF was assessed by both the Bath AS Functional Index (BASFI) score at Baseline (BL), Wks 2, 8, 12, 16, 20, 24, and the SF-36 Physical Component Summary (PCS) score at BL, Wks 12, and 24.

Bath AS Functional Index (BASFI)
The BASFI is a set of 10 questions designed to determine the degree of functional limitation in patients with AS
Items are related to the past 7 days and are answered on a 100 mm visual analogue scale (VAS)
The BASFI score ranges from 0 to 100, with lower scores reflecting less function limitation
Instrument was administered at Baseline, and at Weeks 2, 4, 8, 12, 16, 20, and 24

SF-36 Health Survey
SF-36 is a widely applied instrument that measures health status in 8 distinct domains
SF-36 also contains 2 summary scores: the physical component summary (PCS) and the mental component summary (MCS). PCS scores were used to evaluate overall physical function in this study, with higher scores reflecting better physical function.
SF-36 has a recall period of 4 weeks, and was administered at Baseline, and at Weeks 12 and 24

Work Productivity Measures

Work productivity (WP) was measured using the Work Productivity and Activity Impairment Questionnaire—Specific Health Problem (WPAI-SHP). The WPAI-SHP is a set of 6 questions designed to determine the impact of a specific health problem on work productivity within the past 7 days. WPAI-SHP work productivity loss scores are expressed as overall work impairment percentages (0-100) due to work time missed and reduced on-the-job effectiveness, with higher numbers indicating greater impairment and less productivity. The instrument was administered at Baseline and Week 24. WP was measured by the Work Productivity and Activity Impairment-Specific Health Problem (WPAI-SHP) questionnaire only at BL and Wk 24; therefore, a direct intention-to-treat analysis comparing the treatment groups was not applicable. Instead, two alternative approaches were used. Pearson correlation analysis assessed the association between PF and WP. Multiple stepwise regression analysis examined the factors associated with improvement of overall WP loss at Week 24 from BL, using selected BL demographic and disease characteristics and the duration of exposure to adalimumab. This statistical analysis is described in more detail below:

Statistical Analysis Plan
ANCOVA with Baseline value as a covariate was used to compare therapies at Week 12 and Week 24 for BASFI and SF-36 PCS scores
Since WPAI-SHP was administered only at Baseline and Wk 24, a direct intention-to-treat analysis comparing the treatment groups was not applicable. Instead, two alternative approaches were used:
Pearson correlation analysis assessed the association between functionality and work productivity loss scores
Multiple stepwise regression analysis examined the factors associated with change of overall work productivity loss at Week 24 from Baseline, using selected Baseline demographic and disease characteristics and the duration of exposure to adalimumab
First, the duration of exposure to adalimumab was included in the model. Then, one by one, other specified baseline variables (age, gender, weight, baseline BASDAI, duration of disease) were selected for addition to the model if significant at the 0.20 level.
After each variable was added, any baseline variable that did not produce an F statistic significant at the 0.05 level was deleted from the list of selected variables The study comprised 315 pts (adalimumab n=208, PBO n=107). At BL, both arms had comparable demographics and disease characteristics. Baseline demographics and clinical characteristics were comparable between treatment groups (Table 56)

TABLE 56

Baseline Demographics and Clinical Characteristics*

|  | Placebo (N = 107) | Adalimumab 40 mg eow (N = 208) |
|---|---|---|
| Age, years | 43.4 | 41.7 |
| Male, n (%) | 79 (73.8) | 157 (75.5) |
| Caucasian, n (%) | 99 (92.5) | 202 (97.1) |
| Disease duration, years | 10.0 | 11.3 |
| BASDAI | 6.3 | 6.2 |
| BASFI | 56.4 | 52.4 |
| SF-36 PCS | 31.8 | 32.9 |
| WPAI-SHP | 40.0 | 43.5 |

*Mean values, unless otherwise indicated.

Patient disposition and completion rates are summarized in Table 43. Functionality Improvement is shown in Tables 57 and 58. At Weeks 12 and 24, adalimumab patients had statistically significantly greater improvement from baseline in BASFI and SF-36 PCS scores compared with placebo patients.

TABLE 57

BASFI Scores at 12 and 24 Weeks[†]

| | Mean Change from Baseline | |
| --- | --- | --- |
| | Placebo | Adalimumab |
| Week 12 | −5.1 | −17.5*** |
| Week 24 | −5.2 | −18.7*** |

[†]Last observation carried forward (LOCF).

***Statistically significant at the P ≤ 0.001 vs. placebo. P value difference between therapies from an ANCOVA with therapy and baseline value as a covariate.

TABLE 58

SF-36 PCS Scores at 12 and 24 Weeks[†]

| | Mean Change from Baseline | |
| --- | --- | --- |
| | Placebo | Adalimumab |
| Week 12 | 1.6 | 6.9*** |
| Week 24 | 1.9 | 7.4*** |

[†]Last observation carried forward (LOCF).

MID = 3; MID = Minimum Important Difference. Kosinski M et al. Arthritis Rheum 2000; 7: 1478-1487.

***Statistically significant at the P = 0.001 vs. placebo. P value difference between therapies from ANCOVA.

It was determined whether there was a correlation between functionality and work productivity loss scores. Functionality scores, as measured by both BASFI and SF-36 PCS, were significantly correlated with the WPAI-SHP work productivity loss scores at Baseline and at Week 24.

Factors Associated with Change in WPAI-SHP Work Productivity Loss Scores

In an attempt to explore the factors associated with improvement of overall work productivity loss at Week 24 from Baseline, multiple stepwise regression analysis was conducted using predetermined baseline demographics, baseline disease characteristics, and the duration of exposure to ADA. Regression analysis results indicated that two factors, duration of exposure to adalimumab and baseline BASDAI scores, were significant predictors of improvement in overall work productivity loss at Week 24 from Baseline (Table 59).

After 24 weeks, adalimumab patients reported more improvement vs. PBO in BASFI (−18.7 vs. −5.2, p<0.001) and SF-36 PCS scores (7.4 vs. 1.9, p<0.001). These two scores significantly correlate with the WPAI overall WP loss scores at BL and Week 24 (Table 60). Duration of exposure to adalimumab and BL disease activity BASDAI score were significant predictors of improvement of overall WP loss at Wk 24 from BL (Table 59).

TABLE 59

Factors Associated with Change from Baseline to Week 24 in WPAI-SHP Scores

| | Parameter estimate | P value |
| --- | --- | --- |
| Duration of Exposure to Adalimumab | −0.07 | 0.0499 |
| Baseline BASDAI | −3.25 | 0.0119 |

Note:
Age, gender, weight and duration of disease were not selected by the stepwise regression analysis.

TABLE 60

The Pearson correlation between WPAI-SHP and PF Measures

| | WPAI-SHP with BASFI | | WPAI-SHP with SF-36 PCS | |
| --- | --- | --- | --- | --- |
| | Coefficient | P value | Coefficient | P value |
| Baseline | 0.44 | <0.0001 | −0.50 | <0.0001 |
| Week 24 | 0.63 | <0.0001 | −0.63 | <0.0001 |

In conclusion, adalimumab-treated AS patients showed significant improvement in physical functioning that is associated with better work productivity.

Example 15

Effectiveness and Safety of Adalimumab (HUMIRA®) Therapy after Failure of Prior TNF-Antagonists in Patients Ankylosing Spondylitis (AS)

Some patients (pts) with active ankylosing spondylitis (AS) do not respond optimally or are intolerant to initial infliximab (IFX) or etanercept (ETN) therapy. Subsequent therapy with another anti-TNF agent has rarely been studied in large pt groups.

The following AS study examined the effectiveness and safety of adalimumab in a large number of patients with active AS—including patients with advanced ankylosis, patients who had been treated unsuccessfully with other TNF antagonists, and/or patients who were receiving various concomitant DMARDs—in real-life clinical practices. The objective of this study was to investigate the effectiveness and safety of switching to adalimumab (ADA) in treating pts with AS who had failed prior IFX or ETN therapy.

Patients enrolled in this following AS study received ADA 40 mg sc eow for 12 weeks in addition to their current anti-rheumatic therapies. The study was a large, open clinical trial designed to reflect normal clinical practice. Main general inclusion criteria included adults who were 18 years of age or older. To qualify for the study, patients had to have had an unsatisfactory response (or intolerance) to standard antirheumatic treatment, i.e., ≥1 NSAID. Patients also had to have active disease, defined as BASDAI ≥4 (AS). Inclusion criteria for patients with prior TNF antagonists included a history of etanercept (ETN) and/or infliximab (IFX), which was allowed if the time since last dosage of prior ETN/IFX was less than or equal to 3 weeks etanercept or greater than or equal to 2 months for infliximab (AS or PsA). Thus, patients with active disease who were previously treated with IFX or ETN were allowed to enroll in the studies provided IFX had been discontinued (dc) ≥2 months before enrollment in any study and ETN had been dc ≥3 weeks before enrollment.

Adverse event (AE) reports were routinely collected. In addition, patients participating in the study exhibited the following baseline AS characteristics (multifold occurrence included): advanced ankylosis of the spine; peripheral arthritis; enthesitis; psoriasis; uveitis; and history of inflammatory bowel disease.

The mean exposure in days of prior TNF antagonists was 543 days (477 median), and the mean interval since the last TNF antagonist was 187 days (82 median). At the time point of this analysis, 1,186 patients had enrolled in the AS study. Of those enrolled, 309 had prior exposure to a TNF inhibitor (154 infliximab; 82 etanercept; and 73 to both infliximab and etanercept). Reasons for stopping the prior TNF antagonist were as follows (n=309 at time point of analysis): 27% never achieved a response, 41% had an initial response which was lost over time, 22% were intolerant, and 10% had other reasons for stopping. Baseline characteristics are provided in Table 61:

TABLE 61

Baseline characteristics

| Patients | No prior ETN/IFX (n = 877) | Prior ETN and/or IFX (n = 309) |
|---|---|---|
| Gender (% male) | 72 | 72 |
| Age (years)* | 44 | 43 |
| AS duration (years)* | 11 | 11 |
| Advanced** AS, yes (%) | 33 | 41 |
| BASDAI score* | 6.2 | 6.5 |
| BASFI (0-10)* | 5.2 | 5.7 |

*Means.
**Inflammatory signs in radiograph in >50% of the spine.

ADA led to marked improvements across in AS patients, including those who had failed prior therapy with a TNF antagonist (see Table 62).

TABLE 62

ADA Effectiveness at Week 12 (% of patients)

| | Parameter | |
|---|---|---|
| | No prior etn/ifx n = 877 | Prior ETN/IFX n = 309 |
| ASAS20 | 80% | 64% |
| ASAS40 | 67% | 47% |
| ASAS5/6 | 63% | 42% |
| BASDAI20 | 84% | 67% |
| BASDIA50 | 64% | 41% |
| BASDAI70 | 44% | 24% |
| ΔBASDAI* | -3.5 | -2.7 |
| ΔBASFI* | -2.5 | -1.7 |

Through Week 12 of ADA therapy, safety data were comparable in pts with/without prior anti-TNF therapy, with 0.0/1.7% of pts with AS experiencing a serious AE. No changes in the known patterns of AEs were observed.

In conclusion, adalimumab was effective and well-tolerated in patients with active and longstanding ankylosing spondylitis in a real-life clinical setting. Switching from a failed anti-TNF therapy to adalimumab was effective and well-tolerated in patients with AS. Furthermore, the benefit-risk ratio of switching to adalimumab was good in patients with prior anti-TNF therapy considering the fact that these patients were more severely ill and more difficult to treat Example 16

Efficacy of Adalimumab in the Treatment of Preradiographic Axial Spondylarthritis Results of a 20-Week, Randomized Controlled Trial with an Open-Label Extension Phase While adalimumab has proven efficacious in the treatment of active ankylosing spondylitis (AS), there are no placebo-controlled study data on the efficacy of TNF antagonists in the treatment of early axial spondylarthritis (SpA) before the occurrence of radiographic sacroiliitis. Therefore, the objective of this analysis was to evaluate the therapeutic effects of adalimumab in patients with NSAID-refractory preradiographic axial SpA (early AS).

The following study was a placebo-controlled trial conducted at 2 centers, where 46 patients with NSAID-refractory preradiographic axial SpA were randomized to placebo or adalimumab 40 mg subcutaneously every other week (eow) for 12 weeks, followed by an open-label extension. Participants had to have had chronic low back pain (duration >3 months, <50 years). A diagnosis of preradiographic axial SpA required at least 2 of the following 3 parameters: inflammatory back pain, HLA-B27 positivity, and an MRI showing acute inflammation of spine or sacroiliac joints. In addition, participants had to have at least 3 of the following 6 criteria: The 3 criteria must include at least 2 of criteria 1-3
  1. Inflammatory back pain
  2. HLA-B27 positive
  3. Positive MRI showing acute inflammatory lesions in spine or sacroiliac joints
  4. Good response to NSAIDs
  5. One or more of the following extra spinal manifestations (uveitis peripheral arthritis, enthesitis)
  6. Positive family history
Participants further had to have a BASDAI ≥4 despite NSAIDs.

The study design was 48 weeks long. Weeks 0-12 consisted of the double-blind, placebo-controlled portion of the trial. 24 participants were included in the placebo arm, and 22 patients were in the adalimumab 40 mg eow arm. From weeks 12 to 28 (36 weeks), all patients were switched to the open-label phase including ada 40 mg eow. Patient characteristics are described below in Table 63:

TABLE 63

Patient characteristics

| | Adalimumab | Placebo |
|---|---|---|
| Number of patients, n | 22 | 24 |
| Mean age, years (range) | 38 (25-64) | 37 (26-54) |
| Mean disease duration, years (range) | 7 (2-16) | 8 (1-24) |
| Percentage of females, % | 59 | 50 |
| HLA-B27 positive, % | 59 | 75 |
| MRI positive, % | 55 | 75 |
| HLA-B27 positive/MRI positive, % | 14 | 54 |
| Inflammatory back pain, % | 100 | 100 |
| Good response to NSAID's, % | 82 | 75 |
| Extraspinal manifestations, %: | 68 | 75 |
| History of uveitis, % | 18 | 4 |
| peripheral arthritis, % | 32 | 29 |
| Enthesitis (MASES-Score), % | 82 | 54 |
| Mean baseline BASDAI (range) | 6.7 (4.2-7.9) | 6.3 (4.2-8.9) |

Efficacy of the study was determined as follows. The primary endpoint was a 40% improvement in the ASessments in Ankylosing Spondylitis criteria (ASAS40). Other clinical outcome assessments included ASAS20, ASAS criteria for partial remission, disease activity (BASDAI), function (BASFI), patient's global assessment of disease activity (numerical rating system), and C-reactive protein (CRP) concentration.

A total of 22 patients (mean age 38 years, 59% female, mean disease duration 7 years, 61% HLA-B27 positive) received adalimumab 40 mg eow, and 24 patients (mean age 37 years, 50% female, mean disease duration 8 years, 75% BLA-B27 positive) received placebo. All patients completed the 12-week trial, and 43 patients completed Week 20.

After 12 weeks, 21% of patients who received placebo reached an ASAS 20 response, 13% achieved an ASAS40, and no patients achieved the ASAS criteria for partial remission. Of patients receiving adalimumab, 68% achieved an ASAS20 (p=0.003 vs. placebo), 55% achieved an ASAS40 (p=0.004), and 23% achieved partial remission (p=0.019). At week 20, 68% of patients receiving ada achieved and ASAS20, 46% achieved an ASAS40, and 23% achieved partial remission. For patients who had switched from placebo and had been on ada for 8 weeks at the week 20 mark, 71% achieved ASAS20, 58% achieved an ASAS40, and 42% achieved partial remission.

After 8 weeks of adalimumab treatment, the percentages of patients who originally received placebo and achieved ASAS20, ASAS40, and ASAS partial remission at Week 20 were 70.8%, 58.3%, and 41.7%, respectively. The substantial efficacy achieved in the adalimumab group remained stable through Week 20: ASAS20 was reached in 68.2%, ASAS40 in 45.5%, and ASAS partial remission were reached in 22.7% of patients.

Figure 35:
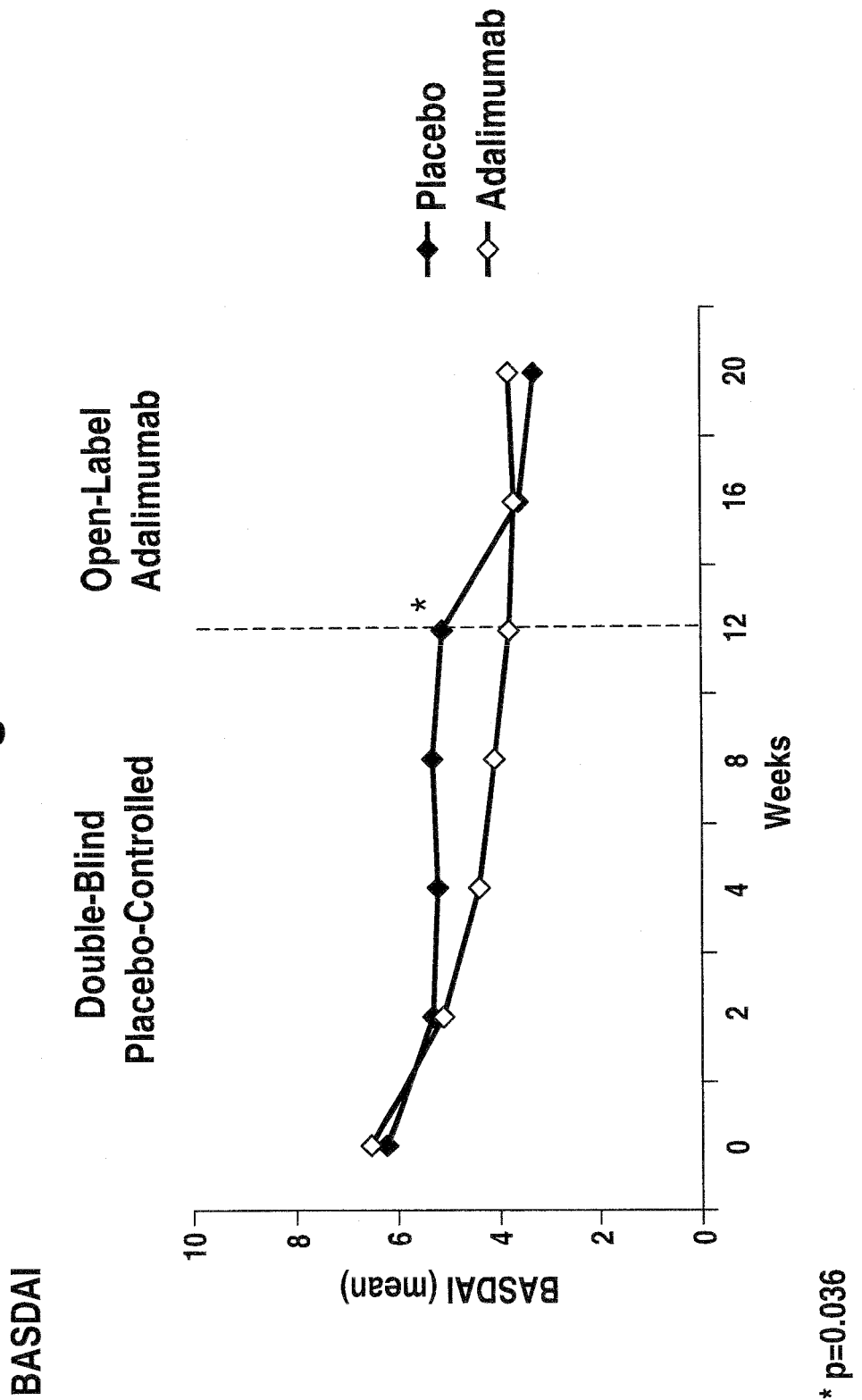

In addition, the BASFI, patient's global assessment, general assessment of pain (NRS), and morning stiffness (BASDAI Questions 5 and 6) all showed significant improvements from baseline (as shown in FIGS. 35 and 36). At week 12, 77% of ada patients achieved BASDAI 20, 50% ada patients achieved BASDAI 50, and 27% ada patients achieved BASDAI 70 (compared to 46% BASDAI 20 for placebo, 21% BASDAI 50 placebo, and 13% BASDAI 70 placebo at week 12). At week 20, 73% of ada patients achieved BASDAI 20, 36% ada patients achieved BASDAI 50, and 27% ada patients achieved BASDAI 70. For patients who were switched from placebo and were on ada for 8 weeks at the week 20 mark, 79% achieved BASDAI20, 50% achieved BASDAI 50, and 42% achieved BASDAI 70.

Subgroup analysis based on HLA-B27 positive and MRI positive status of participants indicated that the subgroup of HLA-B27 positive, MRI positive patients were especially good responders During the 20-week study period, serious adverse events were observed in two patients: one operation of the nose with laryngo-tracheotomy, and one hospitalization because of pain of preknown ovarial adhesion.

In conclusion, adalimumab was the first TNF antagonist to demonstrate clinical efficacy in a controlled study in patients with early preradiographic axial SpA (early AS). In this patient group, adalimumab had a good safety profile. All key outcome parameters (ASAS, BASDAI, BASFI, CRP) showed significant improvements in favour of adalimumab at Weeks 12 and 20

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents, patent applications, and published patent applications cited throughout this application are incorporated herein by reference.

What is claimed is:

1. A method of treating a subject having early axial spondyloarthritis (SpA), comprising administering to the subject an isolated human anti-TNFα antibody, or an antigen-binding portion thereof, to the subject, such that early axial spondyloarthritis is treated.

2. The method of claim 1, wherein the human anti-TNFα antibody, or antigen-binding portion thereof, comprises a light chain variable region (LCVR) comprising the amino acid sequence of SEQ ID NO: 1 and comprises a heavy chain variable region (HCVR) comprising the amino acid sequence of SEQ ID NO: 2.

3. The method of claim 1, wherein a 40 mg dose of the human anti-TNFα antibody, or antigen-binding portion thereof, is subcutaneously administered biweekly to the subject.

4. The method of claim 1, wherein the human anti-TNFα antibody, or an antigen-binding portion thereof, comprises a light chain variable region (LCVR) having a CDR3 domain comprising the amino acid sequence of SEQ ID NO: 3, a CDR2 domain comprising the amino acid sequence of SEQ ID NO: 5, and a CDR1 domain comprising the amino acid sequence of SEQ ID NO: 7; and comprises a heavy chain variable region (HCVR) comprising a CDR3 domain comprising the amino acid sequence of SEQ ID NO: 4, a CDR2 domain comprising the amino acid sequence of SEQ ID NO: 6, and a CDR1 domain comprising the amino acid sequence of SEQ ID NO: 8.

5. The method of claim 1, wherein the human anti-TNFα antibody, or antigen-binding portion thereof, is adalimumab.

6. The method of claim 5, wherein a 40 mg dose of adalimumab is subcutaneously administered biweekly to the subject.

7. A method of treating a subject having early axial spondyloarthritis (SpA), comprising selecting a subject having early axial SpA and administering to the subject an isolated human anti-TNFα antibody, or an antigen-binding portion thereof, to the subject, such that early axial spondyloarthritis is treated, wherein the human anti-TNFα antibody, or an antigen-binding portion thereof, comprises a light chain variable region (LCVR) having a CDR3 domain comprising the amino acid sequence of SEQ ID NO: 3, a CDR2 domain comprising the amino acid sequence of SEQ ID NO: 5, and a CDR1 domain comprising the amino acid sequence of SEQ ID NO: 7; and comprises a heavy chain variable region (HCVR) comprising a CDR3 domain comprising the amino acid sequence of SEQ ID NO: 4, a CDR2 domain comprising the amino acid sequence of SEQ ID NO: 6, and a CDR1 domain comprising the amino acid sequence of SEQ ID NO: 8.

8. The method of claim 7, wherein the subject is selected before occurrence of radiographic sacroiliitis.

9. The method of claim 7, wherein the human anti-TNFα antibody, or an antigen-binding portion thereof, comprises a light chain variable region (LCVR) comprising the amino acid sequence of SEQ ID NO: 1 and comprises a heavy chain variable region (HCVR) comprising the amino acid sequence of SEQ ID NO: 2.

10. The method of claim 7, wherein the human anti-TNFα antibody, or an antigen-binding portion thereof, is adalimumab.

\* \* \* \* \*

SEQUENCE LISTING

```
<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105
```

```
<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
 1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
 1               5
```

```
<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
 1               5                  10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
 1               5

<210> SEQ ID NO 9
<211> LENGTH: 107
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region
```

```
<400> SEQUENCE: 10

Gln Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
1               5

<210> SEQ ID NO 12
<211> LENGTH: 9
<212> TYPE: PRT
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
1               5
```

```
<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
 1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
 1               5

<210> SEQ ID NO 17
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
 1               5

<210> SEQ ID NO 18
<211> LENGTH: 9
<212> TYPE: PRT
<213> ORGANISM: Artificial Sequence
<220> FEATURE:
<223> OTHER INFORMATION: VLL0G7 light chain variable region CDR3

<400> SEQUENCE: 18

Gln Lys Tyr Asn Ser Ala Pro Tyr Asn
 1               5

<210> SEQ ID NO 19
<211> LENGTH: 9
<212> TYPE: PRT
<213> ORGANISM: Artificial Sequence
<220> FEATURE:
<223> OTHER INFORMATION: VLL0G9 light chain variable region CDR3

<400> SEQUENCE: 19

Gln Lys Tyr Thr Ser Ala Pro Tyr Thr
 1               5

<210> SEQ ID NO 20
<211> LENGTH: 9
<212> TYPE: PRT
<213> ORGANISM: Artificial Sequence
<220> FEATURE:
<223> OTHER INFORMATION: VLL0H1 light chain variable region CDR3

<400> SEQUENCE: 20

Gln Lys Tyr Asn Arg Ala Pro Tyr Asn
 1               5

<210> SEQ ID NO 21
```

```
<211> LENGTH: 9
<212> TYPE: PRT
<213> ORGANISM: Artificial Sequence
<220> FEATURE:
<223> OTHER INFORMATION: VL1OH10 light chain variable region CDR3

<400> SEQUENCE: 21

Gln Lys Tyr Asn Ser Ala Ala Tyr Ser
  1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
  1               5

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
  1               5

<210> SEQ ID NO 24
<211> LENGTH: 9
<212> TYPE: PRT
<213> ORGANISM: Artificial Sequence
<220> FEATURE:
<223> OTHER INFORMATION: VL0.1F4 light chain variable region CDR3

<400> SEQUENCE: 24

Gln Lys Tyr Ile Ser Ala Pro Tyr Thr
  1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
  1               5

<210> SEQ ID NO 26
<211> LENGTH: 9
<212> TYPE: PRT
<213> ORGANISM: Artificial Sequence
<220> FEATURE:
<223> OTHER INFORMATION: LOE7.A light chain variable region CDR3

<400> SEQUENCE: 26

Gln Arg Tyr Asn Arg Ala Pro Tyr Ala
  1               5

<210> SEQ ID NO 27
<211> LENGTH: 12
```

```
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
 1               5                  10

<210> SEQ ID NO 33
<211> LENGTH: 12
<212> TYPE: PRT
```

```
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
 1               5                  10

<210> SEQ ID NO 36
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                               321

<210> SEQ ID NO 37
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg gtctcagct atcacttgga atagtggtca catagactat     180
gcggactctg tgagggccg attcaccatc tccagagaca cgccaagaa ctccctgtat     240
```

```
ctgcaaatga acagtctgag agctgaggat acggccgtat attactgtgc gaaagtctcg      300
taccttagca ccgcgtcctc ccttgactat tggggccaag gtaccctggt caccgtctcg      360
agt                                                                    363
```